United States Patent
Tanaka et al.

(10) Patent No.: US 8,021,357 B2
(45) Date of Patent: Sep. 20, 2011

(54) BODY-INSERTABLE APPARATUS

(75) Inventors: Shinsuke Tanaka, Hachioji (JP); Hironao Kawano, Hino (JP); Hironobu Takizawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 329 days.

(21) Appl. No.: 11/658,509

(22) PCT Filed: May 25, 2006

(86) PCT No.: PCT/JP2006/310494
§ 371 (c)(1),
(2), (4) Date: Jan. 25, 2007

(87) PCT Pub. No.: WO2006/126653
PCT Pub. Date: Nov. 30, 2006

(65) Prior Publication Data
US 2009/0043278 A1 Feb. 12, 2009

(30) Foreign Application Priority Data

May 27, 2005 (JP) ................................. 2005-156430
Jun. 20, 2005 (JP) ................................. 2005-179706

(51) Int. Cl.
*A61K 9/22* (2006.01)

(52) U.S. Cl. .................. 604/890.1; 604/891.1; 604/131; 604/132; 604/156; 604/134; 604/135; 604/140; 604/145

(58) Field of Classification Search ............... 604/93.01, 604/95.03, 117, 118, 131, 132, 133, 138, 604/141, 144, 156, 157, 502, 506, 890.1, 604/891.1; 128/897–899
See application file for complete search history.

(56) References Cited

U.S. PATENT DOCUMENTS

| | | | | |
|---|---|---|---|---|
| 4,507,115 A * | 3/1985 | Kambara et al. | ............. | 604/135 |
| 5,217,449 A | 6/1993 | Yuda et al. | | |
| 6,699,218 B2 * | 3/2004 | Flaherty et al. | ............... | 604/131 |
| 7,338,468 B2 * | 3/2008 | Freyman | .................. | 604/103.01 |
| 7,429,258 B2 * | 9/2008 | Angel et al. | .................. | 604/173 |
| 2001/0025168 A1 * | 9/2001 | Gross et al. | .................. | 604/506 |
| 2003/0171734 A1 * | 9/2003 | Seward et al. | ................ | 604/506 |

(Continued)

FOREIGN PATENT DOCUMENTS

JP S57-39776 B2 8/1982

(Continued)

OTHER PUBLICATIONS

Extended European Search Report dated Feb. 28, 2011.

*Primary Examiner* — Theodore Stigell
*Assistant Examiner* — Kami A Bosworth
(74) *Attorney, Agent, or Firm* — Scully, Scott, Murphy & Presser, P.C.

(57) ABSTRACT

A body-insertable apparatus including a balloon for storing a medical fluid in a capsule-like casing, and an injection needle including an elastic membrane. The body-insertable apparatus discharges the medical fluid due to contraction of the balloon, applies a discharge pressure of the medical fluid to the elastic membrane to expand the elastic membrane, and projects the injection needle from the casing due to the expansion of the elastic membrane. Further, the body-insertable apparatus has a channel forming unit for forming a channel connecting to the balloon and a channel connecting to the injection needle, and a communication adjusting mechanism. The communication adjusting mechanism adjusts a communicated state between the channels and, thereby controlling the start of medical-fluid discharge operation by the balloon.

26 Claims, 42 Drawing Sheets

U.S. PATENT DOCUMENTS

| | | |
|---|---|---|
| 2004/0111011 A1 | 6/2004 | Uchiyama et al. |
| 2004/0143213 A1* | 7/2004 | Hunter et al. ............. 604/93.01 |
| 2005/0124875 A1 | 6/2005 | Kawano et al. |
| 2006/0200083 A1* | 9/2006 | Freyman et al. ............. 604/181 |

FOREIGN PATENT DOCUMENTS

| | | |
|---|---|---|
| JP | 2002-516723 A | 6/2002 |
| JP | 2003-093332 A | 4/2003 |
| JP | 2003-325438 A | 11/2003 |
| JP | 2003-325440 A | 11/2003 |
| JP | 2004-041709 A | 2/2004 |
| JP | 2004-222998 | 8/2004 |
| JP | 2005-052358 A | 3/2005 |
| JP | 2005-124708 | 5/2005 |
| WO | WO 99/62576 | 12/1999 |
| WO | WO 2004/066903 A2 | 8/2004 |

* cited by examiner

FIG.16
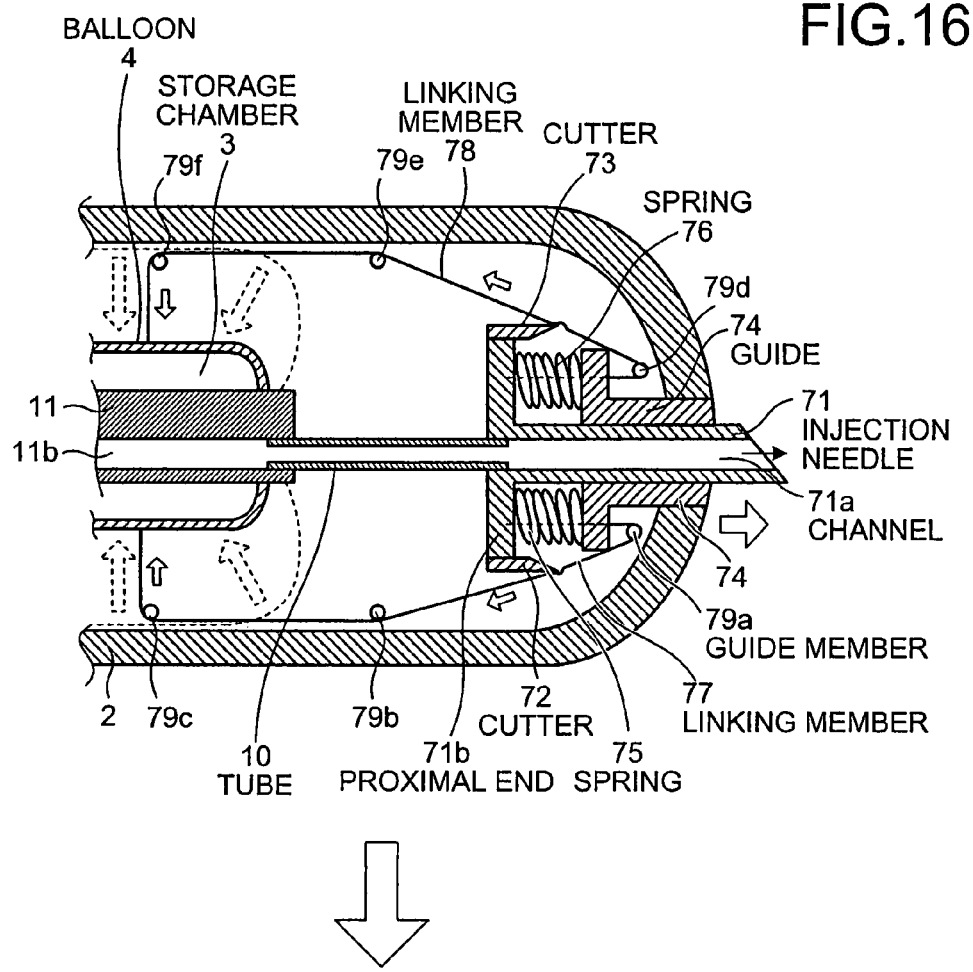
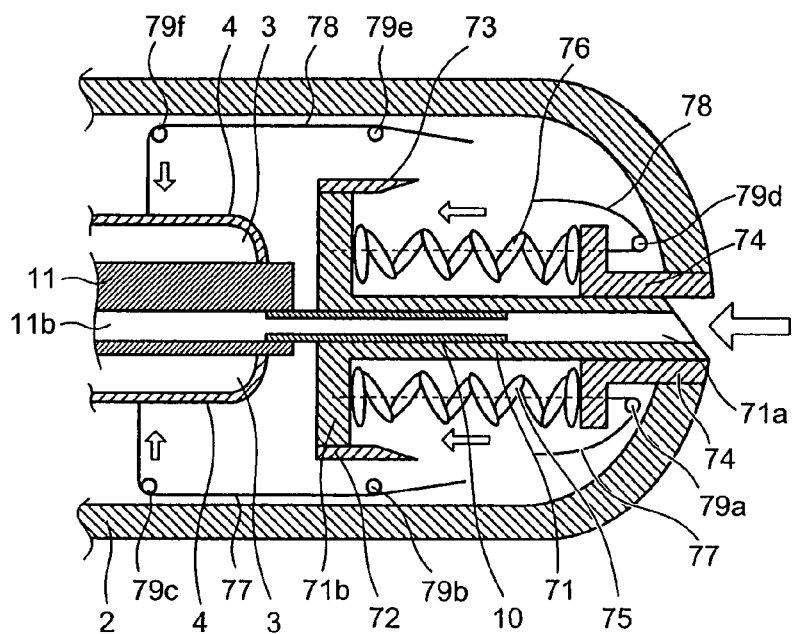

FIG. 36
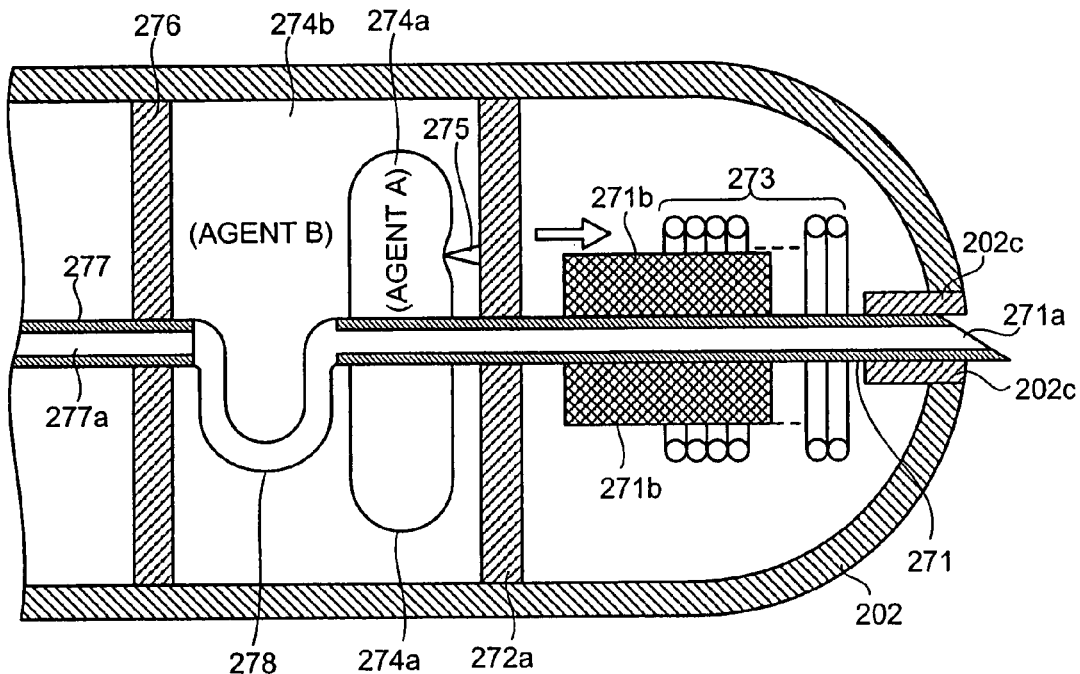
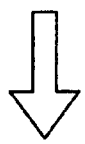
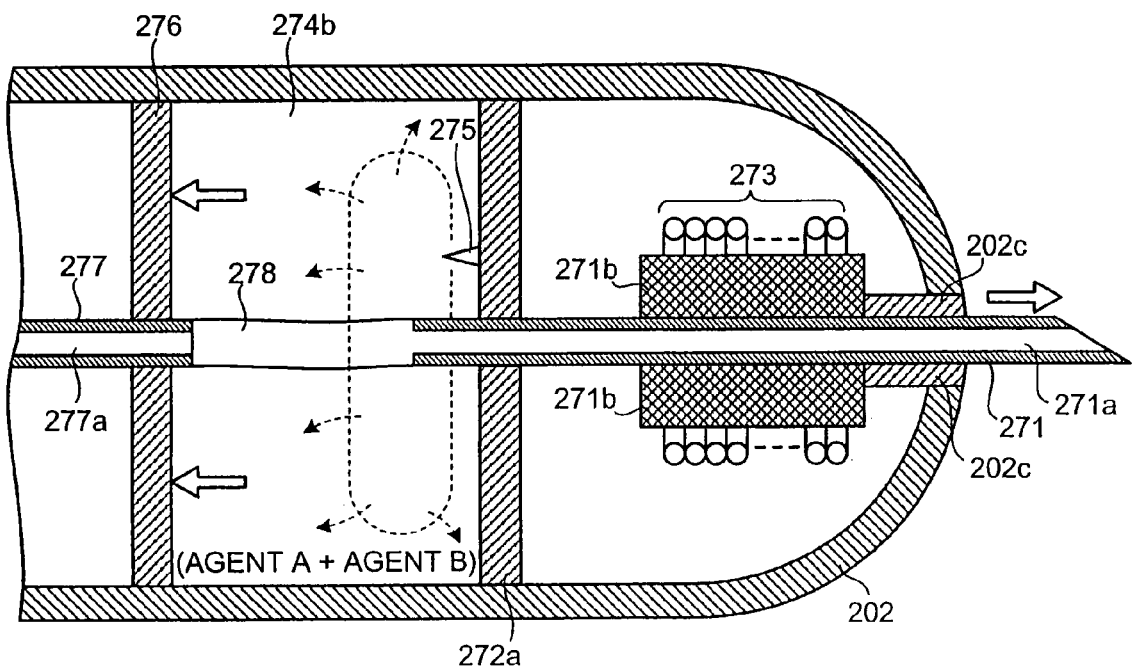

BODY-INSERTABLE APPARATUS

CROSS-REFERENCE TO RELATED APPLICATIONS

This application claims benefit to PCT Application JP 2006/310494 filed on May 25, 2006, which claims benefit to Japanese Patent Application 2005-179706 filed on Jun. 20, 2005.

TECHNICAL FIELD

The present invention relates to a body-insertable apparatus introduced into a subject, and having a local injection function for injecting a medical fluid to a desired region in the subject.

BACKGROUND ART

Conventionally, a body-insertable apparatus for collecting a body fluid or the like of a patient has been proposed. Specifically, the body-insertable apparatus has a configuration including a capsule exterior case, a storage chamber arranged in the exterior case for leading to the outside of the body-insertable apparatus and storing the body fluid or the like, and an input control mechanism for controlling an input of the body fluid or the like to the storage chamber. In this body-insertable apparatus, the input control mechanism collects the body fluid or the like by performing predetermined control when the body-insertable apparatus reaches the desired region in the subject such as the patient, and stores the collected body fluid or the like in the storage chamber.

As a specific example of such a conventional body-insertable apparatus, there has been proposed one apparatus having a collecting needle with a collecting unit having water absorptivity being provided at the end, a drive mechanism for putting in and out the collecting needle from the exterior case, and an input/output control mechanism that controls projection operation and storing operation of the collecting needle by the drive mechanism by an electromagnetic force (for example, see Patent Document 1). In such a body-insertable apparatus, the drive mechanism projects the collecting needle from the exterior case based on the control of the input/output control mechanism, so that the body fluid or the like adheres to the collecting unit at the end. Thereafter, the drive mechanism stores the collecting needle in the exterior case together with the collecting unit to which the body fluid or the like adheres, based on the control of the input/output control mechanism. The body-insertable apparatus collects the body fluid or the like in the desired region in the subject by using the collecting unit.

Further, by applying the above mechanism, a body-insertable apparatus that directly supplies the medical fluid to an affected part in the subject has been also proposed. This body-insertable apparatus has an injection needle instead of the collecting needle of the body-insertable apparatus, for example, described in the Patent Document 1, and the injection needle is projected from the exterior case so as to inject the medical fluid to the affected part. In this case, the body-insertable apparatus includes a projecting drive mechanism for performing projection operation of the injection needle, and a discharge mechanism for discharging the medical fluid to the injection needle, and by operating the projecting drive mechanism and the discharge mechanism, respectively, to inject the medical fluid to the affected part.

Patent Document 1: Japanese Utility Model Application No. S57-39776

DISCLOSURE OF INVENTION

Problem to be Solved by the Invention

However, in the conventional body-insertable apparatus, since power is consumed for performing the projection of the injection needle and the medical-fluid discharge operation, respectively, there is a problem in that power consumption is large at the time of injecting the medical fluid to the affected part in the subject.

The projecting drive mechanism generally requires many components such as an electromagnet, a permanent magnet, and a spring required for performing the projection of the injection needle. Therefore, in many cases, the exterior case including such a projecting drive mechanism and the discharge mechanism therein becomes large, thereby making it difficult to make the apparatus small.

The present invention has been achieved to solve the above problems, and it is an object of the present invention to provide a body-insertable apparatus that can have a small size and perform the projection of the injection needle while reducing the power consumption.

Means for Solving Problem

A body-insertable apparatus according to one aspect of the present invention has a storage chamber for storing a medical fluid in a capsule-like casing and introduced into a subject to inject the medical fluid to a desired region in the subject, wherein the body-insertable apparatus includes an injection needle that projects from the casing by using a predetermined drive source for discharge of the medical fluid to inject the medical fluid into the desired region in the subject.

In the body-insertable apparatus, the predetermined drive source may be a medical-fluid discharger that discharges the medical fluid by changing the volume of the storage chamber and projects the injection needle from the casing by using a physical force for the discharge of the medical fluid.

The body-insertable apparatus may include a discharge controller that controls the start of volume change of the storage chamber by the medical-fluid discharger to start the discharge of the medical fluid.

In the body-insertable apparatus, the physical force for the discharge of the medical fluid may be a discharge pressure of the medical fluid.

In the body-insertable apparatus, the physical force for the discharge of the medical fluid may be a pressurizing force for pressurizing the medical fluid by reducing the volume of the storage chamber.

In the body-insertable apparatus, the medical-fluid discharger may include a medical fluid pressurizing unit that pressurizes the medical fluid by reducing the volume of the storage chamber, an elastic membrane that holds the injection needle, and a medical fluid channel for allowing the medical fluid pressurized by the medical fluid pressurizing unit to flow toward the elastic membrane side, wherein the elastic membrane may expand by using the discharge pressure of the medical fluid flowing via the medical fluid channel, and the injection needle may be projected from the casing due to the expansion.

In the body-insertable apparatus, the elastic membrane may use the discharge pressure of the medical fluid to expand and generate an elastic force, and when the discharge pressure of the medical fluid decreases to equal to or less than the elastic force, the elastic membrane may bring the injection needle back to the casing by using the elastic force.

In the body-insertable apparatus, the medical-fluid discharger may include a medical fluid pressurizing unit that pressurizes the medical fluid by reducing the volume of the storage chamber, and a medical fluid channel for allowing the medical fluid pressurized by the medical fluid pressurizing unit to flow to an end of the injection needle, wherein the medical fluid pressurizing unit may push out the injection needle by applying the discharge pressure of the medical fluid to the end of the injection needle.

In the body-insertable apparatus, one end of the medical fluid channel may be connected to the end of the injection needle, and the vicinity of the one end of the medical fluid channel can freely extend in a projecting direction of the injection needle.

The body-insertable apparatus may further include an elastic member that projects the injection needle by the medical-fluid discharger and generates an elastic force, and when the discharge pressure of the medical fluid decreases to equal to or less than the elastic force, uses the elastic force to bring the injection needle back to the casing.

In the body-insertable apparatus, the medical-fluid discharger may include a medical fluid pressurizing unit that pressurizes the medical fluid by reducing the volume of the storage chamber, a medical fluid channel for allowing the medical fluid pressurized by the medical fluid pressurizing unit to flow to the injection needle, and a linking unit that links the medical fluid pressurizing unit to the injection needle and uses the pressurizing force by the medical fluid pressurizing unit to project the injection needle, in conjunction with the volume reduction of the storage chamber.

The body-insertable apparatus may further include an elastic member that generates an elastic force in a direction returning the injection needle into the casing, upon projection of the injection needle, and a cutting unit that cuts the linking unit when the injection needle projects to a predetermined position, wherein the elastic member may use the elastic force to bring the injection needle back to the casing, when the cutting unit cuts the linking unit.

In the body-insertable apparatus, the medical-fluid discharger may include a medical fluid pressurizing unit which includes the injection needle, pressurizes the medical fluid by reducing the volume of the storage chamber and projects the injection needle from the casing, and a medical fluid channel for allowing the medical fluid pressurized by the medical fluid pressurizing unit to flow to the injection needle.

In the body-insertable apparatus, the medical fluid pressurizing unit may include a pressurizing force source that generates the pressurizing force, and a piston which includes the injection needle, uses the pressurizing force of the pressurizing force source to slide in the storage chamber, pressurizes the medical fluid, and projects the injection needle from the casing.

In the body-insertable apparatus, the storage chamber may be formed of a deformable medical fluid bag including the medical fluid channel, and the medical fluid pressurizing unit may include a belt wound around the medical fluid bag, a shape memory member that deforms to generate the pressurizing force, upon reaching predetermined temperature, and an associating unit which is fitted with one end of the belt, the injection needle, and the shape memory member, uses the pressurizing force by the shape memory member to shift the one end of the belt in a direction fastening the medical fluid bag, and projects the injection needle from the casing.

In the body-insertable apparatus, the shape memory member may return to an original shape to lose the pressurizing force when the temperature thereof decreases to lower than the predetermined temperature, and may bring the injection needle back to the casing.

In the body-insertable apparatus, the discharge controller may control to raise the temperature of the shape memory member to higher than the predetermined temperature to start discharge of the medical fluid, or to drop the temperature of the shape memory member to lower than the predetermined temperature to stop the discharge of the medical fluid.

In the body-insertable apparatus, the discharge controller may control so as to stop volume reduction of the storage chamber by the medical-fluid discharger, to stop the discharge of the medical fluid.

In the body-insertable apparatus, the medical fluid channel may include a first channel connecting to the storage chamber, and a second channel connecting to the injection needle side, the discharge controller may control a connection state of the first channel and the second channel, and the medical-fluid discharger may start volume reduction of the storage chamber when the first channel and the second channel are connected to each other, and may stop volume reduction of the storage chamber when the first channel and the second channel are closed.

The body-insertable apparatus may include a medical-fluid discharger that discharges the medical fluid by changing the volume of the storage chamber, and a discharge starting unit that projects the injection needle from the casing by using the predetermined drive source and starts a discharge operation of the medical-fluid discharger.

In the body-insertable apparatus, the medical-fluid discharger may discharge the medical fluid by compressing the storage chamber.

In the body-insertable apparatus, the medical-fluid discharger may include a medical fluid channel that connects the storage chamber to the injection needle, and the discharge starting unit may be a communication adjusting unit that applies a pressing force to a part of the medical fluid channel to cut off a communicated state of the medical fluid channel, projects the injection needle by using the predetermined drive source, and reduces the pressing force to adjust the medical fluid channel to the communicated state, thereby starting the discharge operation of the medical-fluid discharger.

In the body-insertable apparatus, the communication adjusting unit may include a pressing unit that applies a pressing force to a part of the medical fluid channel to cut off the communicated state of the medical fluid channel, a projecting unit that holds the injection needle and uses the predetermined drive source to project the injection needle from the casing, and an associating unit that associates the projection operation by the projecting unit to project the injection needle with the communication adjusting operation by the pressing unit to reduce the pressing force to adjust the medical fluid channel to the communicated state.

In the body-insertable apparatus, the medical fluid channel may be formed of a first channel connecting to the storage chamber and a second channel connecting to the injection needle, and the communication adjusting unit may cut off the communicated state of the medical fluid channel by applying a pressing force to a region between the first channel and the second channel, use the predetermined drive source to project the injection needle, and adjust the medical fluid channel to the communicated state by reducing the pressing force, thereby starting the discharge operation of the medical-fluid discharger.

In the body-insertable apparatus, the predetermined drive source may be a shape memory member, and the communication adjusting unit may use a driving force generated by a shape change of the shape memory member to project the injection needle, and adjust the medical fluid channel to the communicated state.

In the body-insertable apparatus, the communication adjusting unit may include an elastic member that generates the pressing force, and when the shape memory member loses the driving force, may use the pressing force to store at least the injection needle in the casing.

In the body-insertable apparatus, the discharge starting unit may include a projecting unit that projects the injection needle by using the predetermined drive source, and an energy generator that contains a first agent and a second agent, mixes the first agent and the second agent, in conjunction with the projection operation of the projecting unit to project the injection needle, and chemically generates a driving energy to transmit the driving energy to the medical-fluid discharger, and the medical-fluid discharger may discharge the medical fluid by using the driving energy.

In the body-insertable apparatus, the discharge starting unit may include an energy generator that contains a first agent and a second agent, mixes the first agent and the second agent by using the predetermined drive source, and chemically generates a driving energy to transmit the driving energy to the medical-fluid discharger, and a projecting unit that projects the injection needle by using the driving energy.

In the body-insertable apparatus, the driving energy may be thermal energy, and the projecting unit may have a shape memory member that extends by using the thermal energy to generate a driving force for projecting the injection needle.

In the body-insertable apparatus, the driving energy may be thermal energy, and the medical-fluid discharger may have a shape memory member that extends by using the thermal energy to generate a pressurizing force for compressing the storage chamber.

The body-insertable apparatus according to another aspect of the present invention has a medical fluid and an injection needle in a capsule-like casing, and introduced into a subject to inject the medical fluid to a desired region in the subject, the body-insertable apparatus includes a medical-fluid discharger that pressurizes and discharges the medical fluid, and projects the injection needle from the casing, and an elastic member that generates an elastic force in a direction returning the injection needle into the casing, upon projection of the injection needle, and when a physical force for projecting the injection needle decreases to equal to or less than the elastic force, uses the elastic force to bring the injection needle back to the casing.

In the body-insertable apparatus, the physical force for projecting the injection needle may be a discharge pressure of the medical fluid, and may decrease to equal to or less than the elastic force when the medical-fluid discharger finishes discharge of a desired amount of the medical fluid.

The body-insertable apparatus may include a discharge controller that controls to stop discharge of the medical fluid, so that the physical force for projecting the injection needle decreases to equal to or less than the elastic force.

In the body-insertable apparatus, the physical force for projecting the injection needle may be a pressurizing force for pressurizing the medical fluid, and the medical-fluid discharger may include a linking unit that links the injection needle to the medical-fluid discharger and uses the pressurizing force to project the injection needle, and a cutting unit that cuts the linking unit when the injection needle projects to a predetermined position, to reduce the physical force for projecting the injection needle to equal to or less than the elastic force.

The body-insertable apparatus according to still another aspect of the present invention has a storage chamber for storing a medical fluid in a capsule-like casing and an injection needle, and is introduced into a subject to inject the medical fluid to a desired region in the subject, wherein the body-insertable apparatus includes a shape memory member that changes its shape under a predetermined temperature condition to generate a driving force, an elastic member that generates an elastic force which is against the driving force and less than the driving force, and a storing unit that projects the injection needle from the casing by using the driving force, and when the shape memory member loses the driving force, stores the injection needle in the casing by using the elastic force.

The body-insertable apparatus may include a medical-fluid discharger that has a medical fluid channel connecting the storage chamber and the injection needle, and may discharge the medical fluid via the medical fluid channel, wherein the storing unit may apply the elastic force to a part of the medical fluid channel to cut off the communicated state of the medical fluid channel, thereby stopping the discharge operation of the medical-fluid discharger.

According to still another aspect of the present invention, a method of injecting a medical fluid into a desired region in a subject, includes a step of introducing a body-insertable apparatus into the subject, a step of projecting an injection needle at the desired region in the subject using a predetermined drive source provided in the body-insertable apparatus; and a step of starting discharge of the medical fluid simultaneously with the step of projecting the injection needle using the predetermined drive source.

Effect of the Invention

According to the present invention, a drive mechanism for executing the projection of the injection needle can be simplified, and the projection of the injection needle can be executed without consuming driving power, thereby realizing power saving of the body-insertable apparatus that performs the projection of the injection needle and downsizing of the apparatus.

BRIEF DESCRIPTION OF DRAWINGS

FIG. 16 is a schematic diagram schematically exemplifying a state where the injection needle is stored by cutting linking members;

FIG. 36 is a schematic diagram schematically exemplifying a state where the injection needle is projected, and medicines are mixed, to chemically generate dynamic energy;

EXPLANATIONS OF LETTERS OR NUMERALS

Figure 1:
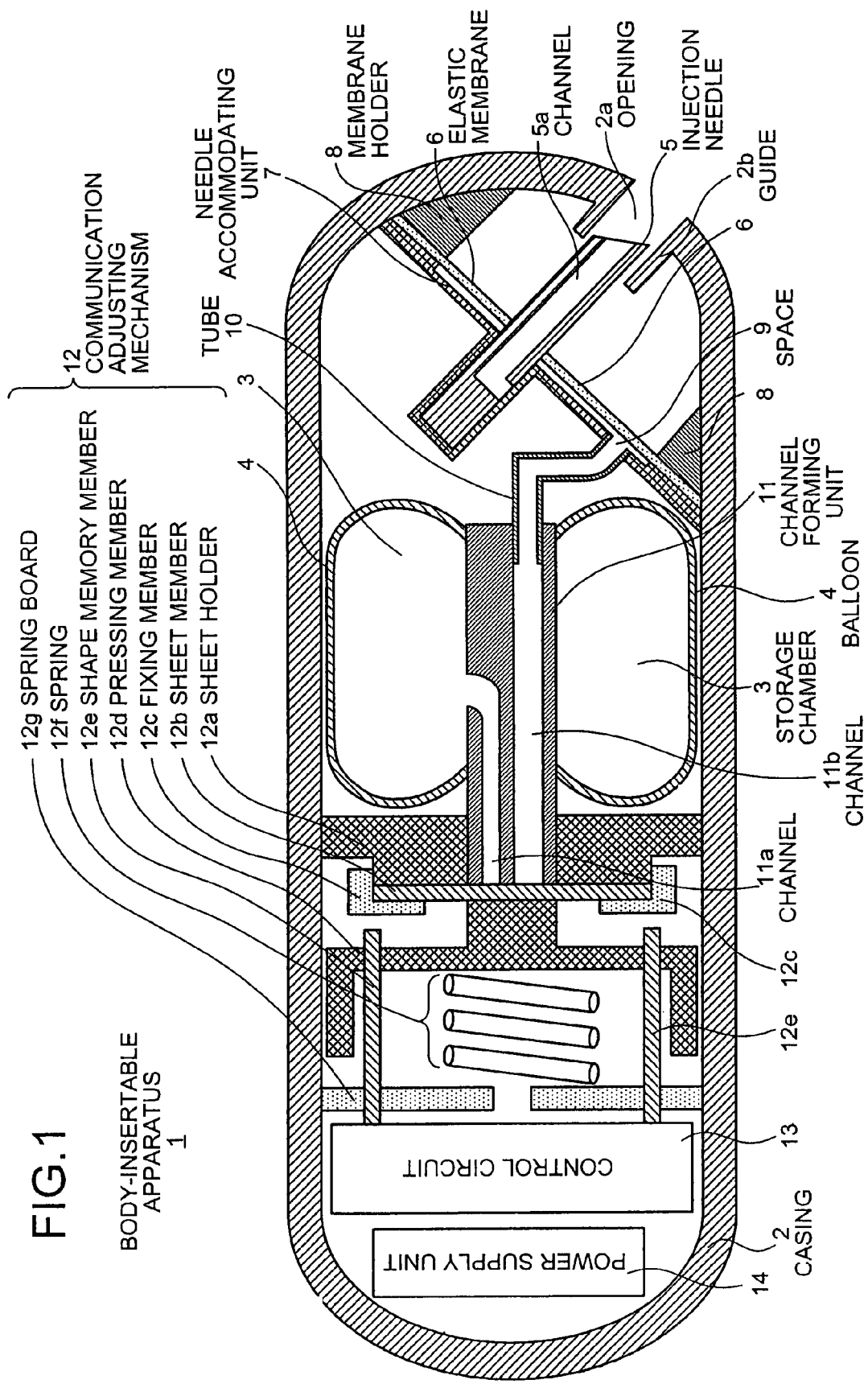
FIG. 1 is a schematic sectional view schematically showing one configuration example of a body-insertable apparatus according to a first embodiment of the present invention.

1 Body-insertable apparatus
2 Casing
2a Opening
2b Guide
3 Storage chamber
4 Balloon
5 Injection needle
5a Channel
6 Elastic membrane
7 Needle accommodating unit

| Column 1 | Column 2 |
|---|---|
| 8 Membrane holder | 110 Body-insertable apparatus |
| 9 Space | 111 Storage bag |
| 10 Tube | 111a Storage chamber |
| 11 Channel forming unit | 112 Belt |
| 11a, 11b Channel | 113 Belt holding member |
| 12 Communication adjusting mechanism | 114 Injection needle |
| 12a Sheet holder | 114a Channel |
| 12b Sheet member | 115 Associating member |
| 12c Fixing member | 116 Guide |
| 12d Pressing member | 117 Tube |
| 12e Shape memory member | 118a to 118e Shape memory member |
| 12f Spring | 201, 220 Body-insertable apparatus |
| 12g Spring board | 202 Casing |
| 13 Control circuit | 202a, 202b, 202c Guide |
| 14 Power supply unit | 203 Storage chamber |
| 20 Body-insertable apparatus | 204 Balloon |
| 21 Piston | 205 Injection needle |
| 22 Spring | 205a Channel |
| 23 Spring board | 206 Tube |
| 24 Channel forming unit | 207 Channel forming unit |
| 24a Channel | 207a, 207b Channel |
| 25 Storage chamber | 208 Communication adjusting mechanism |
| 30 Body-insertable apparatus | 208a Sheet holder |
| 31a, 31b Shape memory member | 208b Sheet member |
| 32 Tube holding unit | 208c Fixing member |
| 40 Body-insertable apparatus | 208d Pressing member |
| 41 Injection needle | 208e Holding board |
| 41a Channel | 208f, 208g Associating member |
| 41b Proximal end | 208h Spring |
| 42 Guide | 208i Spring board |
| 42a Spring board | 208j, 208k Shape memory member |
| 43 Spring | 211a to 211f Guide member |
| 44 O-ring | 212 O-ring |
| 50 Body-insertable apparatus | 213 Control circuit |
| 51 Bellows tube | 214 Power supply unit |
| 52 Guide | 240 Body-insertable apparatus |
| 60, 70 Body-insertable apparatus | 241 Piston mechanism |
| 71 Injection needle | 241a Cylinder |
| 71a Channel | 241b Piston |
| 71b Proximal end | 241c Spring |
| 72, 73 Cutter | 242 Storage chamber |
| 74 Guide | 243 Channel forming unit |
| 75, 76 Spring | 243a Channel |
| 77, 78 Linking member | 250 Body-insertable apparatus |
| 79a to 79f Guide member | 251 Injection needle |
| 80 Body-insertable apparatus | 251a Channel |
| 81 Piston | 252 Tube |
| 82 Injection needle | 253 Communication adjusting mechanism |
| 82a Channel | 253a Sheet holder |
| 83 Guide | 254a, 254b Channel |
| 83a Channel | 250a Body-insertable apparatus |
| 84 O-ring | 255 Injection needle |
| 85 Communication adjusting mechanism | 255a Channel |
| 85a Sheet holder | 256 Channel forming unit |
| 86a, 86b Channel | 256a Channel |
| 87 Storage chamber | 257a, 257b O-ring |
| 88 Spring | 258 Communication adjusting mechanism |
| 90 Body-insertable apparatus | 258a Pressing member |
| 91, 94 Holding board | 258b Cylinder |
| 92 Piston drive mechanism | 258c Holding board |
| 92a Pressing member | 259 Tube |
| 92b Rotation shaft | 259a Channel |
| 92c Guide | 260 Body-insertable apparatus |
| 92d Motor | 261 Injection needle |
| 95 Storage chamber | 261a Channel |
| 96 Control circuit | 262 Tube |
| 100 Affected part | 262a Variable area |

263 Holding board
264 Communication adjusting mechanism
264a Pressing member
264b Associating member
264c Holding board
264d Spring
264e Spring board
264f Spring
264g Shape memory member
265 Rotation shaft
270 Body-insertable apparatus
271 Injection needle
271a Channel
271b Magnetic member
272a, 272b Holding board
273 Solenoid
274a Balloon
274b, 274c Storage chamber
275 Needle
276 Piston
277 Channel forming unit
277a Channel
278 Tube
279 Control circuit
280 Body-insertable apparatus
281 Injection needle
281a Channel
282 Piston mechanism
282a Cylinder
282b Piston
282c Shape memory member
282d Heat conducting member
283 Storage chamber
284 Heat generator
284b, 284c Storage chamber
284c Partition
285 Associating member
285a Pressing unit
286 Linear actuator
287 Holding board
288 Control circuit
290 Body-insertable apparatus
291 Injection needle
291a Channel
291b Proximal end
292 Needle projecting mechanism
292a Cylinder
292b Shape memory member
292c Heat conducting member
293 Piston mechanism
293a Cylinder
293b Piston
293c Shape memory member
293d Heat conducting member
294 Heat generator
294a, 294b Storage chamber
294c Partition
295 Heater
296 Control circuit
297 Tube
298 Storage chamber

BEST MODE(S) FOR CARRYING OUT THE INVENTION

Exemplary embodiments of a body-insertable apparatus according to the present invention will be explained below in detail with reference to the accompanying drawings. Note that the present invention is not limited to the embodiments.

First Embodiment

FIG. 1 is a schematic sectional view schematically showing one configuration example of a body-insertable apparatus according to a first embodiment of the present invention. A body-insertable apparatus 1 is introduced into a subject, and a medical fluid pre-stored in a storage chamber is injected to a desired region in the subject. As shown in FIG. 1, the body-insertable apparatus 1 includes a capsule-like casing 2 having a size easily swallowable by the subject such as a patient. The body-insertable apparatus 1 includes, in the casing 2, a balloon 4 that forms a storage chamber 3 for storing the medical fluid, an injection needle 5 for injecting the medical fluid to the desired region in the subject, and a tube 10 and a channel forming unit 11 for forming a first channel connecting to the storage chamber 3 and a second channel connecting to the injection needle 5. The body-insertable apparatus 1 includes a communication adjusting mechanism 12 for adjusting a communicated state between the first channel and the second channel, an elastic membrane 6 that pushes the injection needle 5 out of the casing 2 by using a discharge pressure of the medical fluid, a control circuit 13 that controls a driving state of the communication adjusting mechanism 12, and a power supply unit 14 that supplies driving power to the control circuit.

The storage chamber 3 stores beforehand the medical fluid to be injected to the desired region in the subject. Specifically, in the first embodiment, the storage chamber 3 is formed in an area covered with an inner surface of the balloon 4 and a surface of the channel forming unit 11, and the medical fluid is stored in the area. The balloon 4 forms the most part of an external wall of the storage chamber 3, and is realized by using an elastic member such as rubber. The balloon 4 expands due to injection of the medical fluid in a predetermined amount and stores the medical fluid, while maintaining the expanding state, that is, a state where the storage chamber 3 is expanded. When the storage chamber 3 and the injection needle 5 communicate with each other due to operations of the communication adjusting mechanism 12 and the elastic membrane 6, the balloon 4 reduces a volume of the storage chamber 2 accompanying with contraction thereof to pressurize the medical fluid, and discharges the medical fluid via the injection needle 5. That is, the balloon 4 functions as a medical fluid pressurizing unit that pressurizes the medical fluid by reducing the volume of the storage chamber 3 to discharge the medical fluid.

The injection needle 5 projects from the casing 2 by using a predetermined drive source for the discharge of the medical fluid to inject the medical fluid stored in the storage chamber 3 to the desired region in the subject. The injection needle 5 has a channel 5a formed therein for connecting a distal end side (a side forming a sharp point) for puncturing the subject and a side near a proximal end, and is provided in the casing 2 so as to be freely put in and out. Specifically, the proximal end side of the injection needle 5 is accommodated in a needle accommodating unit 7 in a state of being held by the elastic membrane 6. The injection needle 5 projects outside of the casing 2 due to the expansion of the elastic membrane 6, and is stored in the casing 2 due to the contraction of the elastic membrane 6. In this manner, the injection needle 5 slides along a guide 2b provided in the casing 2, and is put in and out via an opening 2a of the casing 2.

The elastic membrane 6 is an elastic member such as rubber or silicone resin, and for projecting the injection needle 5 by the discharge pressure of the medical fluid, or storing the projected injection needle 5 in the casing 2 by the elastic force. Specifically, the elastic membrane 6 holds the injection needle 5 substantially near the center in such a manner that the elastic membrane 6 is penetrated by the injection needle 5, and a rim thereof is held by a membrane holder 8. In this case, an area of the elastic membrane 6 put between the injection needle 5 and the membrane holder 8 is free, and can expand upon application of the discharge pressure of the medical fluid (one example of the physical force for the discharge of the medical fluid) to this area.

The medical-fluid discharger realized by including the elastic membrane 6, the balloon 4, the tube 10, and the channel forming unit 11 discharges the medical fluid in the storage chamber 3 by reducing the volume of the storage chamber 3, and projects the injection needle 5 from the casing 2 by using the physical force for the discharge of the medical fluid (for example, the discharge pressure of the medical fluid). In other words, the medical-fluid discharger functions as a drive source (drive source for the discharge of the medical fluid) that discharges the medical fluid in the storage chamber 3, and generates a driving force (physical force for the discharge of the medical fluid) for projecting the injection needle 5 from the casing 2.

The needle accommodating unit 7 accommodates the proximal end side of the injection needle 5. The membrane holder 8 holds the elastic membrane 6. Specifically, the membrane holder 8 is provided on the inner wall of the casing 2 near the opening 2a, and holds the rim of the elastic membrane 6 that holds the injection needle 5. The needle accommodating unit 7 is set on the inner side of the casing 2 in such a manner that the rim of the elastic membrane 6 is pushed against the membrane holder 8. In this case, a space 9 for temporarily storing the medical fluid to be discharged outside via the injection needle 5 is formed in an area surrounded by the elastic membrane 6 and the needle accommodating unit 7.

Since the needle accommodating unit 7 and the membrane holder 8 fix the rim portion of the elastic membrane 6 in such a manner, it is prevented that the medical fluid discharged to the space 9 leaks to an area in the casing 2 where a component other than the injection needle 5 and the tube 10, for example, the balloon 4 or the membrane holder 8 is arranged.

The tube 10 and the channel forming unit 11 are for forming the first channel and the second channel. Specifically, channels 11a and 11b are formed inside of the channel forming unit 11, and the tube 10 is fitted to the channel forming unit 11 in such a manner that the channel 11b and the space 9 are communicated with each other. In this case, the channel 11a communicates with the inside of the balloon 4, that is, the storage chamber 3, and the channel 11b and the tube 10 communicate with the space 9, which is the injection needle 5 side relative to the storage chamber 3. That is, the channel 11a forms the first channel, and the channel 11b and the tube 10 form the second channel. The tube 10 and the channel forming unit 11 circulate the medical fluid in the storage chamber 3, when the channels 11a and 11b communicate with each other due to an operation of the communication adjusting mechanism 12.

It is desired that the channels 11a and 11b are formed parallel with each other along the longitudinal direction of the casing 2. The size of the channel forming unit 11 can be downsized as much as possible by forming the channels 11a and 11b in this manner, thereby promoting downsizing of the body-insertable apparatus 1.

The communication adjusting mechanism 12 adjusts the communicated state of the channels 11a and 11b under control of the control circuit 13. The communication adjusting mechanism 12 has a function of pressurizing the medical fluid by the contraction of the balloon 4, that is, by reducing the volume of the storage chamber 3 by performing the adjustment operation, and controlling start and stop of the discharge operation for discharging the medical fluid. Specifically, the communication adjusting mechanism 12 includes a sheet holder 12a into which the channel forming unit 11 is inserted, a sheet member 12b arranged on the sheet holder 12a so as to cover the end of the channel forming unit 11 exposed on the sheet holder 12a, and a fixing member 12c that fixes a rim portion of the sheet member 12b in a state closely adhering to the sheet holder 12a. The communication adjusting mechanism 12 further includes a pressing member 12d that applies a predetermined pressing force to the sheet member 12b, a spring 12f that generates the pressing force applied by the pressing member 12d, a spring board 12g that holds the spring 12f, and a shape memory member 12e that changes a position of the pressing member 12d relative to the sheet member 12b.

The sheet holder 12a is a plate member for holding the sheet member 12b. Specifically, the sheet holder 12a is fixed on, for example, the inner wall of the casing 2, to hold the channel forming unit 11, with the channel forming unit 11 penetrating the sheet holder 12a, and also holds the sheet member 12b so as to cover an area in which the end of the channel forming unit 11 is exposed. It is desired to form a breather (not shown) in the sheet holder 12a or the spring board 12g so that a space where the balloon 4 and the like are arranged, a space where the pressing member 12d and the like are arranged, and a space where the control circuit 13 and the like are arranged do not interrupt each other. Formation of the breather suppresses that a negative pressure is generated with the contraction of the balloon 4 in the space in the casing 2 where the balloon 4 is arranged, and it can prevent the contraction of the balloon 4 from being interrupted.

The sheet member 12b physically controls the communicated state between the first channel and the second channel, that is, between the channels 11a and 11b. Specifically, the sheet member 12b is formed of a watertight and flexible material such as a silicon sheet. The sheet member 12b is arranged on the sheet holding member 12a so as to cover the end of the channel forming unit 11 exposed on the sheet holder 12a, and fixed in a state with the rim portion being stuck to the sheet holder 12a by the fixing member 12c. When the predetermined pressing force is applied by the pressing member 12d, the sheet member 12b is maintained in the state of adhering to the end of the channel forming unit 11, thereby closing the opening of the channels 11a and 11b and cutting off the communicated state between the channels 11a and 11b. On the other hand, when the pressing force by the pressing member 12d decreases, the sheet member 12b is away from the end of the channel forming unit 11 by the discharge pressure of the medical fluid discharged from the channel 11a, thereby connecting the channels 11a and 11b with each other.

The fixing member 12c fixes the rim portion of the sheet member 12b to the sheet holder 12a. Specifically, the fixing member 12c applies the pressing force to the rim portion of the sheet member 12b toward the sheet holder 12a so that the rim portion of the sheet member 12b adheres and is fixed to the sheet holder 12a. Since the fixing member 12c fixes the sheet member 12b in this manner, the central portion of the sheet member 12b, that is, the vicinity of the end of the channel forming unit 11 freely deforms the shape thereof corresponding to the pressing force of the pressing member 12d. At the same time, the sheet member 12b arranged in this manner prevents the medical fluid circulating between the channels 11a and 11b from leaking to the area in the casing 2 where components other than the channels 11a and 11b, for example, the pressing member 12d or the control circuit 7 is arranged.

The spring 12f generates the pressing force to be applied to the sheet member 12b by the pressing member 12d. Specifically, one end of the spring 12f is fixed to the spring board 12g, and the other end is fixed to the pressing member 12d, with the spring length being maintained shorter than a natural length. The thus arranged spring 12f functions so as to energize the elastic force (spring force) in a direction in which the sheet member 12b is positioned relative to the pressing member 12d.

The shape memory member 12e changes the position of the pressing member 12d relative to the sheet member 12b. Specifically, the shape memory member 12e has a cylindrical or coiled (for example, SMA coil) structure, and is formed of a shape memory alloy having a predetermined shape memory characteristic and a predetermined electrical resistivity. The shape memory member 12e is fixed to the spring board 12g at one end, and to the pressing member 12d at the other end, and has a sufficient length so that the pressing member 12d can abut against the sheet member 12b under a temperature condition, for example, same as the temperature in the subject. On the other hand, the shape memory member 12e changes its shape at a predetermined temperature, for example, under a temperature condition sufficiently higher than the temperature in the subject, so that the pressing member 12d is away from the sheet member 12b.

The control circuit 13 functions so as to control the shape change of the shape memory member 12e according to the presence of power supply to the shape memory member 12e, and control discharge start and discharge stop of the medical fluid in the storage chamber 3 through the control of the shape change. Specifically, the control circuit 13 functions so as to supply the current to the shape memory member 12e when the body-insertable apparatus 1 introduced into the subject reaches a desired region in the subject, for example, the affected part. Joule heat is generated in the shape memory member 12e due to the flow of the current in the shape memory member 12e, and the temperature of the shape memory member 12e rises higher than the predetermined temperature resulting from the Joule heat. The shape of the shape memory member 12e changes as described above due to the temperature rise. In this case, the medical fluid in the storage chamber 3 is discharged (injected) to the desired region in the subject via the channels 11a and 11b, the tube 10, the space 9, and the channel 5a of the injection needle 5. On the other hand, the control circuit 13 reduces the temperature of the shape memory member 12e to lower than the predetermined temperature (for example, about the same temperature as that in the subject) by stopping the current supply to the shape memory member 12e. The shape memory member 12e changes the shape so as to press the pressing member 12d against the sheet member 12b, due to the temperature drop. In this case, the balloon 4 stops the operation for reducing the volume of the storage chamber 3 to stop the medical-fluid discharge operation.

As the configuration for specifying the current supply timing by the control circuit 13, for example, a timer mechanism can be provided, or a radio reception mechanism is incorporated therein and a control signal can be supplied from the outside.

Figure 2:
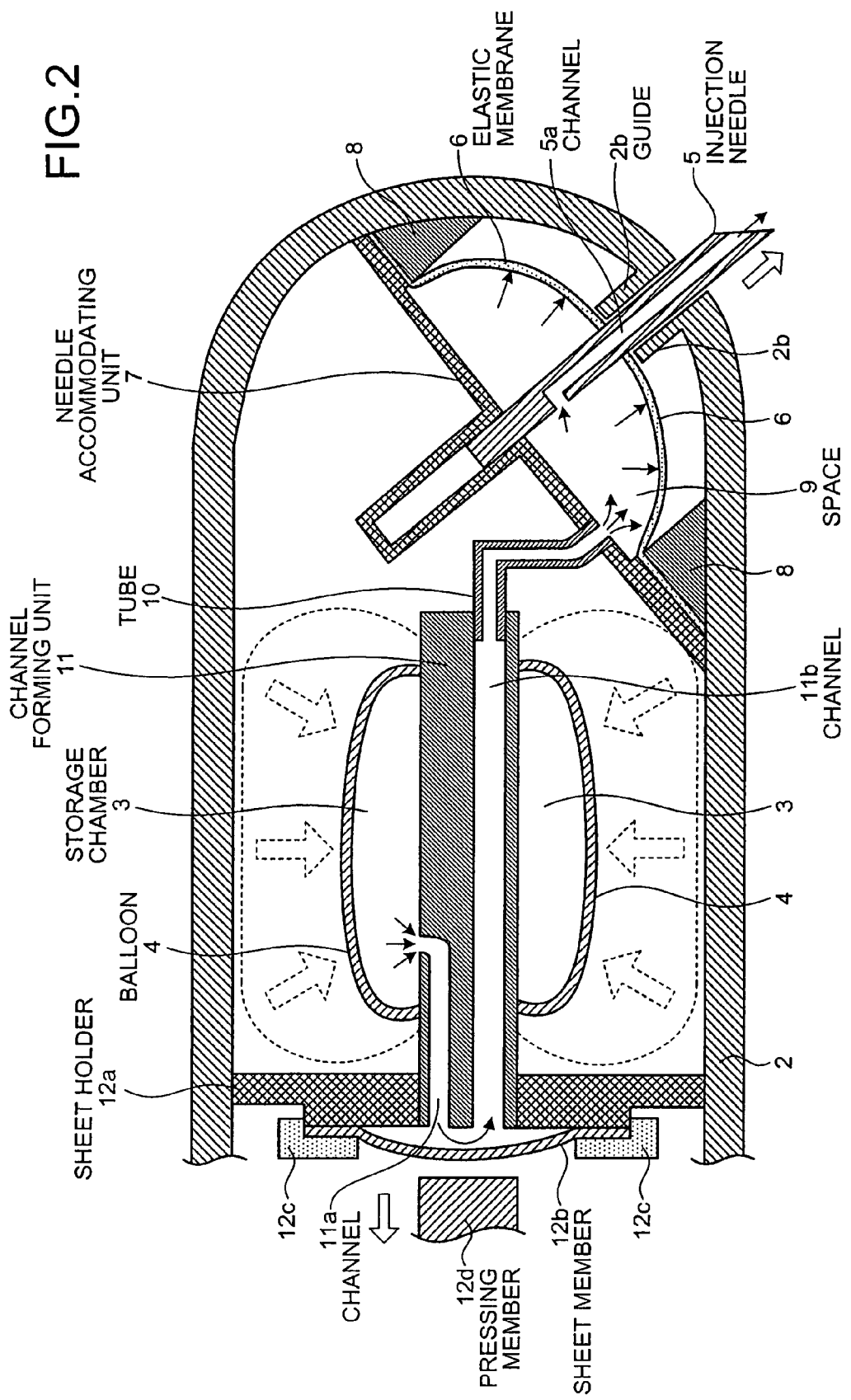
FIG. 2 is a schematic sectional view schematically exemplifying a projected state of an injection needle by applying a discharge pressure of a medical fluid to an elastic membrane.

An operation of the body-insertable apparatus 1 is explained next. FIG. 2 is a schematic sectional view schematically exemplifying a projected state of the injection needle 5 from the casing 2 by applying a discharge pressure of the medical fluid to the elastic membrane 6. The projection operation of the injection needle 5 and the medical-fluid discharge operation are explained with reference to FIG. 2.

The control circuit 13 supplies the predetermined current to the shape memory member 12e to raise the temperature of the shape memory member 12e by generating the Joule heat in the shape memory member 12e. The shape memory member 12e changes its shape when the temperature rises higher than the predetermined temperature. Specifically, the shape memory member 12e is formed in a bar shape and has been subjected to a shape memory treatment so that the length thereof in the longitudinal direction contracts at a high temperature. When the temperature rises higher than the predetermined temperature due to the Joule heat, the shape memory member 12e changes its shape so that the longitudinal length becomes shorter. The pressing member 12d fixed to the one end of the shape memory member 12e moves in a direction away from the sheet member 12b, as shown in FIG. 2, due to the contraction of the shape memory member 12e in the longitudinal direction. As a result, the pressing force against the sheet member 12b decreases (or becomes zero).

The adhesion state between the sheet member 12b with the end of the channel forming unit 11 is released due to the decrease of the pressing force against the sheet member 12b. In this case, the channels 11a and 11b change to the communicated state, and this triggers the contraction of the balloon 4 for reducing the volume of the storage chamber 3 due to the contraction, to pressurize the medical fluid in the storage chamber 3. The medical fluid pressurized due to the contraction of the balloon 4 is discharged, as shown in FIG. 2, to the injection needle 5 side, that is, to the space 9 via the channels 11a and 11b forming the first channel and the second channel, and the tube 10.

The balloon 4 continues the contraction so long as the channels 11a and 11b are in the communicated state, to sequentially discharge the medical fluid to the space 9, and applies the discharge pressure of the medical fluid to the elastic membrane 6. In this case, the storage amount of the medical fluid in the space 9 increases with the contraction of the balloon 4, and the discharge pressure of the medical fluid to be applied to the elastic membrane 6 increases with the increase of the storage amount. The elastic membrane 6 gradually expands using the thus applied discharge pressure of the medical fluid, so that the injection needle 5 slides in a direction protruding from the casing 2 accompanying the expansion. At the same time, the elastic membrane 6 generates the elastic force, which contracts the expanded shape (that is, restores the shape to the original shape). The elastic membrane 6 continues to expand due to the application of the discharge pressure larger than the elastic force. When the discharge pressure of the medical fluid increases to higher than a predetermined threshold, the elastic membrane 6 projects the injection needle 5 from the casing 2, so that the channel 5a of the injection needle 5 communicates with the space 9.

Thus, since the elastic membrane 6 projects the injection needle 5, the channels 11a and 11b, the tube 10, the space 9, and the channel 5a are communicated with each other, and the balloon 4 can discharge the medical fluid from the end of the injection needle 5 via the channels 11a and 11b, the tube 10, the space 9, and the channel 5a. In other words, the balloon 4, the elastic membrane 6, the tube 10, and the channel forming unit 11 constitute the medical-fluid discharger that discharges the medical fluid and projects the injection needle 5 from the casing 2 by using the discharge pressure of the medical fluid. Further, the communication adjusting mechanism 12 and the control circuit 13 constitute the discharge controller that controls the start of the medical-fluid discharge operation by the medical-fluid discharger.

Thereafter, the balloon 4 finishes discharge of the medical fluid in a predetermined amount and gradually stops the contraction, thereby gradually decreasing the discharge pressure of the medical fluid to be applied to the elastic membrane 6. When the discharge pressure of the medical fluid decreases to less than the elastic force, the expanded elastic membrane 6 contracts due to the elastic force, so that the injection needle 5 slides toward the casing 2, and when the discharge pressure of the medical fluid decreases to less than the threshold, the elastic membrane 6 stores the injection needle 5 up to the end of the sharp point in the casing 2. At the same time, the needle accommodating unit 7 accommodates the vicinity of the proximal end of the injection needle 5 to cut off the communicated state between the space 9 and the channel 5a. In other words, when the medical fluid in the predetermined amount or more has been discharged, the balloon 4 finishes the contraction, and the elastic membrane 6 stores the injection needle 5 in the casing 2 by the elastic force.

On the other hand, the communication adjusting mechanism 12 and the control circuit 13 constituting the discharge controller can control the medical-fluid discharge operation to be stopped due to the contraction of the balloon 4, by performing the cutoff adjusting operation of the communicated state between the channels 11a and 11b. Specifically, the control circuit 13 stops the current supply to the shape memory member 12e, so that the temperature of the shape memory member 12e drops to less than the predetermined temperature. According to such control of the control circuit 13, the shape memory member 13e restores the shape of the pressing member 12d to a shape capable of abutting against the sheet member 12b. In this case, the pressing member 12d uses the pressing force generated by the spring 12f to make the sheet member 12b and the end of the channel forming unit 11 adhere to each other, thereby cutting off the communicated state between the channels 11a and 11b.

Thus, by cutting off the communicated state between the channels 11a and 11b, the balloon 4 stops contraction, thereby suspending the medical-fluid discharge operation. In this case, if the balloon 4 has not discharged the medical fluid in an amount equal to or more than the predetermined amount, the balloon 4 has an elastic force (contraction force) of a level capable of resuming the contraction. The discharge pressure of the medical fluid applied to the elastic membrane 6 decreases to a level equal to or lower than the threshold, with the suspension of the discharge operation. As a result, the elastic membrane 6 can store the injection needle 5 in the casing 2, in the same manner as the balloon 4 has finished the discharge of the medical fluid in the predetermined amount or more.

Thereafter, when the control circuit 13 restarts current supply to the shape memory member 12e, the channels 11a and 11b are communicated with each other, and the balloon 4 starts the contraction to resume the medical-fluid discharge operation. Thus, since the communication adjusting mechanism 12 and the control circuit 13 repeat control of stopping and resuming the medical-fluid discharge operation, the balloon 4 can repeat the contraction intermittently until the medical fluid in an amount equal to or larger than the predetermined amount has been discharged. In other words, the medical-fluid discharger constituted by using the balloon 4, the elastic membrane 6, the tube 10, and the channel forming unit 11 can intermittently repeat the projection operation of the injection needle 5 by the discharge pressure of the medical fluid and the medical-fluid discharge operation.

Figure 3:
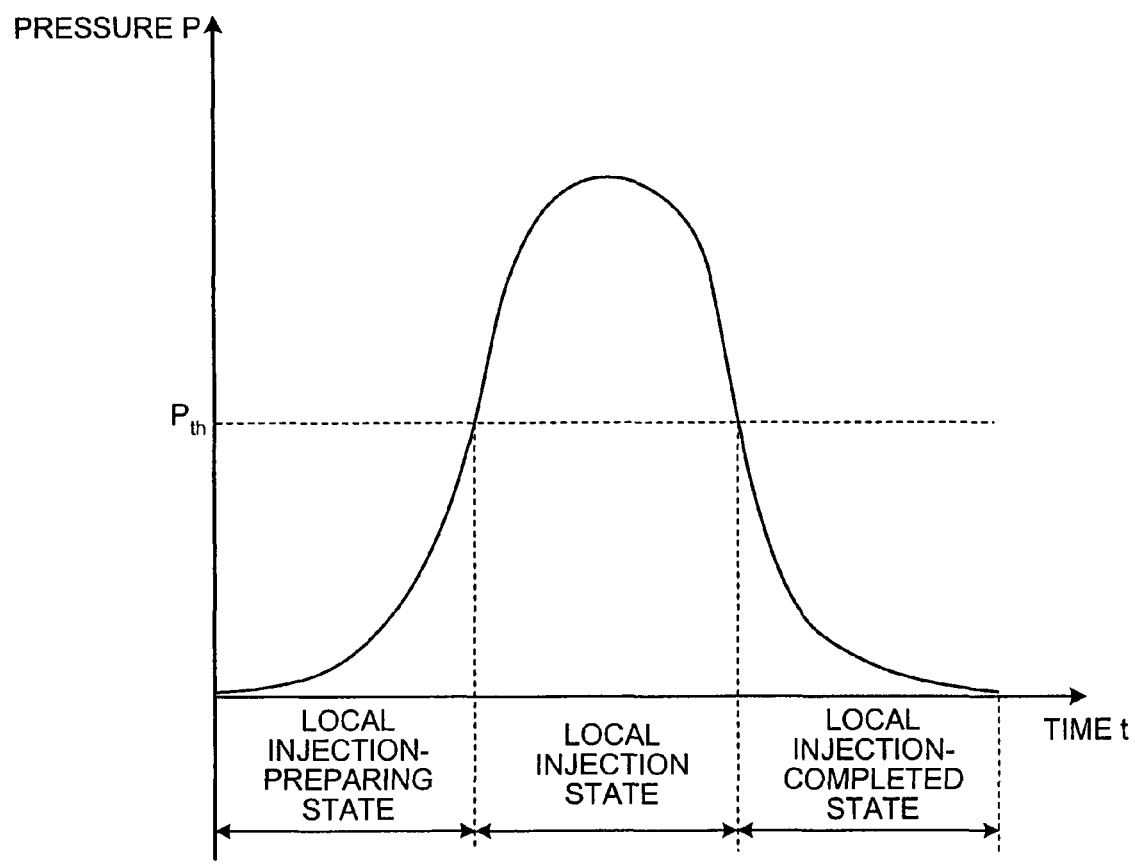
FIG. 3 is a schematic diagram schematically exemplifying changes of the discharge pressure of the medical fluid applied to the elastic membrane.
Figure 4:
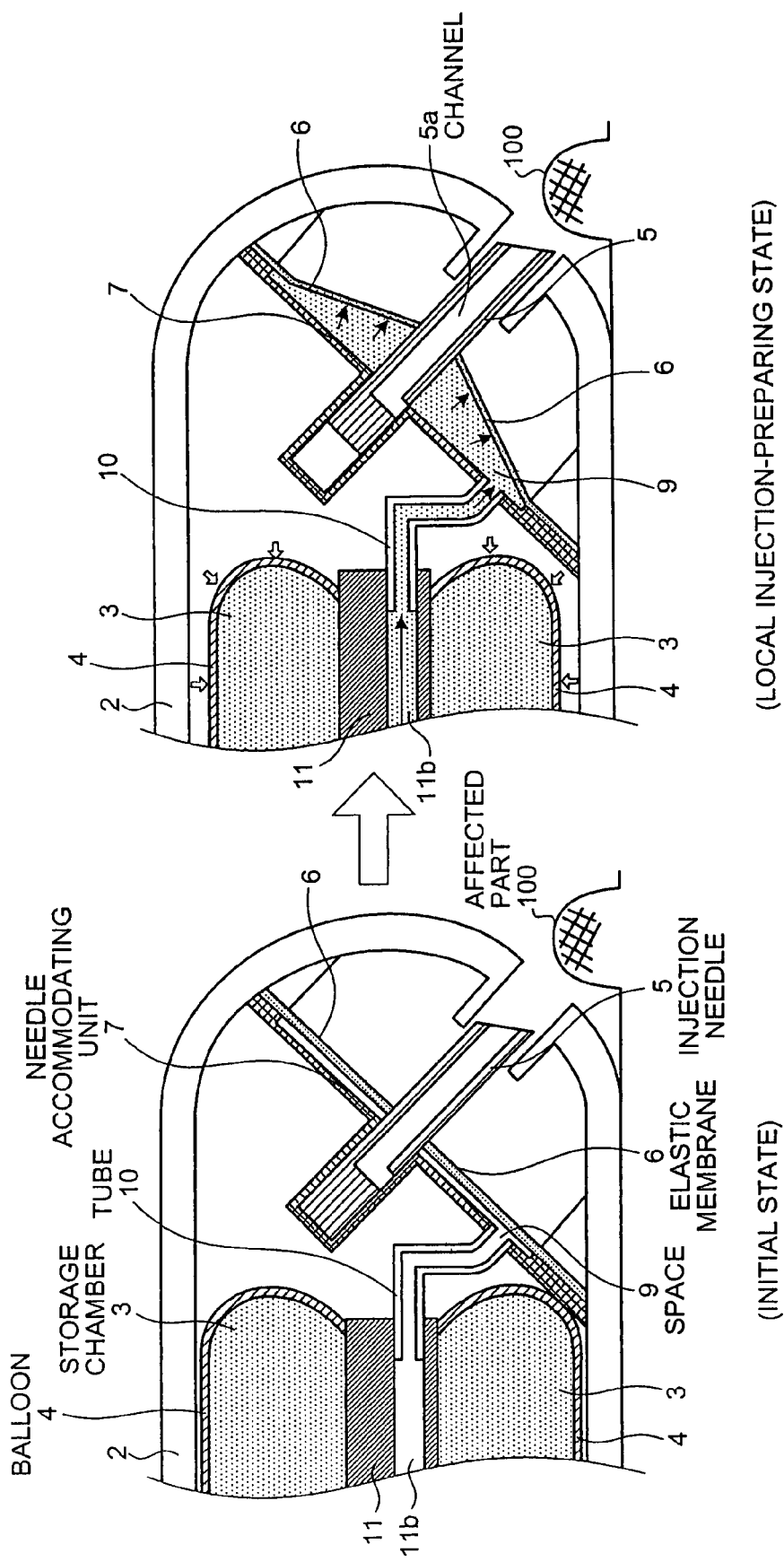
FIG. 4 is a schematic sectional view schematically showing a change of state since start of a discharge operation of the medical fluid until start of projection of the injection needle.
Figure 5:
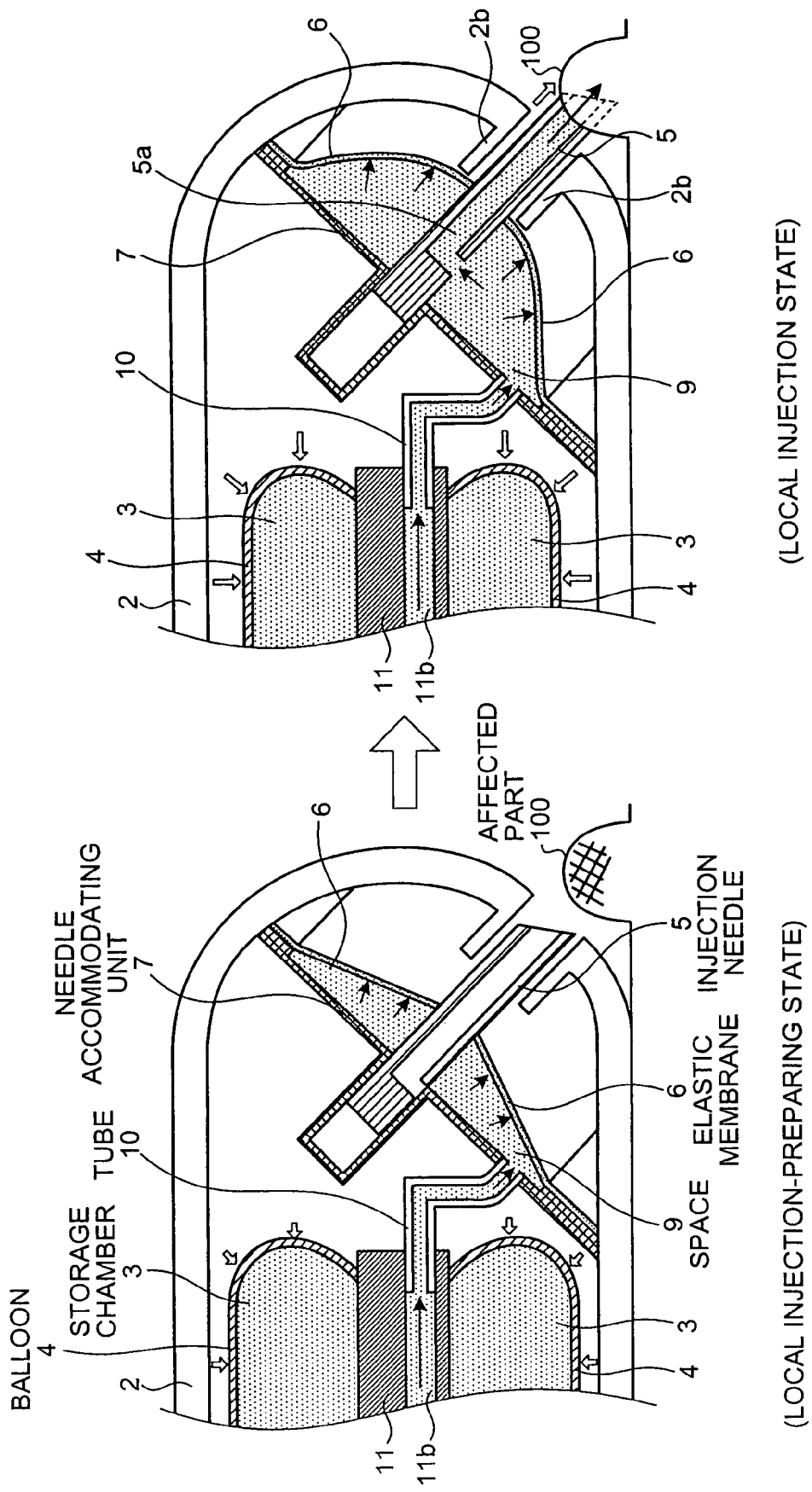
FIG. 5 is a schematic sectional view schematically showing a change of state since start of projection of the injection needle until injection of the medical fluid to a desired region.
Figure 6:
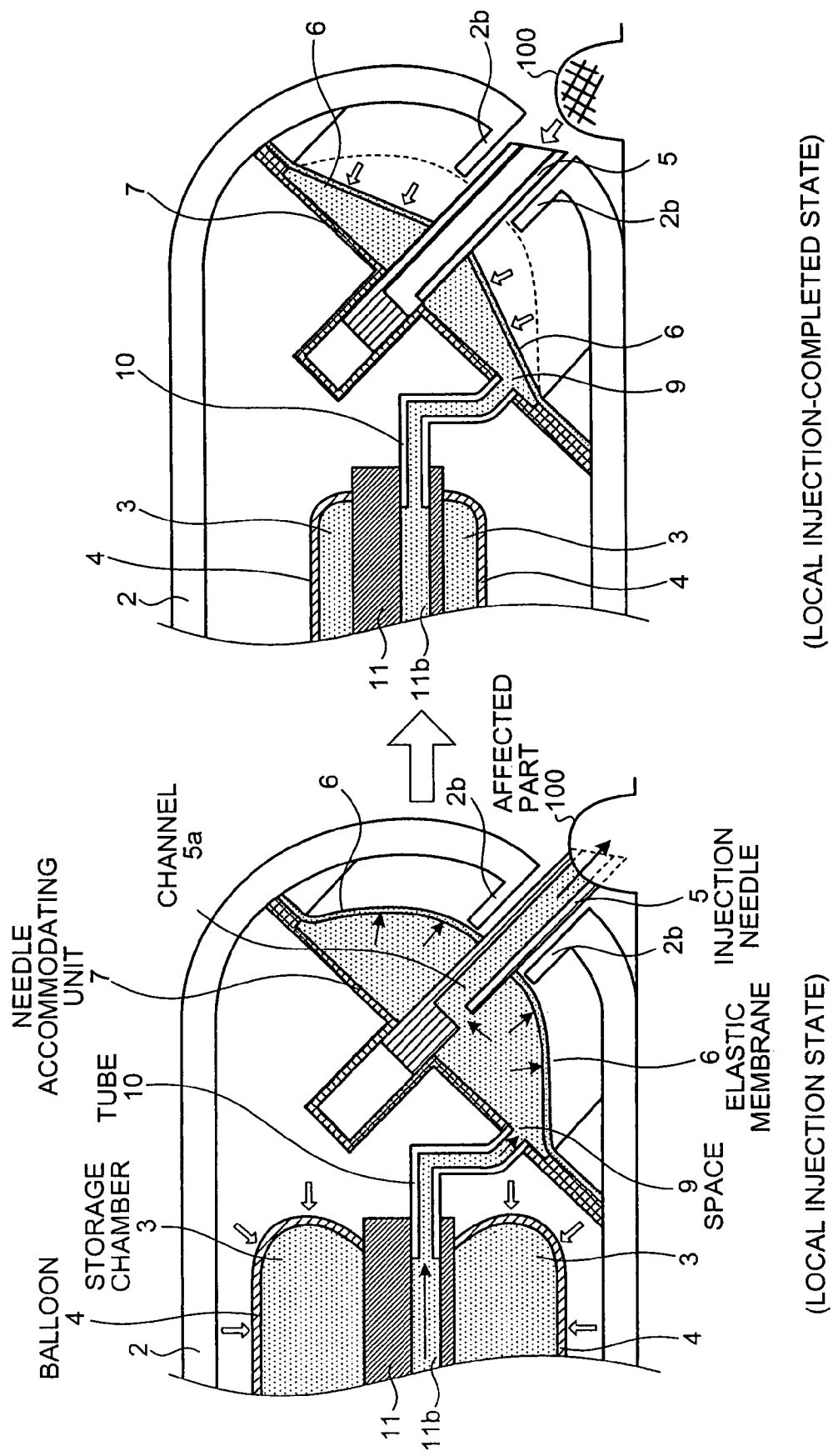
FIG. 6 is a schematic sectional view schematically showing a change of state since injection of the medical fluid to the desired region until the injection needle is stored.

A series of operations of the body-insertable apparatus 1 since projection of the injection needle 5 by using the discharge pressure of the medical fluid until finishing injection of the medical fluid to a desired region in the subject is specifically explained. FIG. 3 is a schematic diagram schematically exemplifying changes of the discharge pressure of the medical fluid applied to the elastic membrane 6. FIG. 4 is a schematic sectional view schematically showing a change of state since start of a discharge operation of the medical fluid until start of projection of the injection needle. FIG. 5 is a schematic sectional view schematically showing a change of state since start of projection of the injection needle until injection of the medical fluid to a desired region. FIG. 6 is a schematic sectional view schematically showing a change of state since injection of the medical fluid to the desired region until the injection needle 5 is stored in the casing. The series of operations of the body-insertable apparatus 1 until the medical fluid has injected to the desired region in the subject are explained with reference to FIGS. 3 to 6.

When the body-insertable apparatus 1 is introduced into the subject and reaches the desired region in the subject, for example, an affected part 100, the control circuit 13 supplies predetermined current to the shape memory member 12e, to control the shape change of the shape memory member 12e. According to the control of the control circuit 13, the pressing member 12d is away from the sheet member 12b to release the adhesion state between the sheet member 12b and the end of the channel forming unit 11. Accompanying this, the balloon 4 starts contraction for reducing the volume of the storage chamber 3, and discharges the medical fluid to the space 9 via the channels 11a and 11b, and the tube 10. The balloon 4 sequentially discharges the medical fluid into the space 9, and applies the discharge pressure of the medical fluid to the elastic membrane 6.

In this case, the body-insertable apparatus 1 changes the state, as shown in FIG. 4, from a state before starting contraction of the balloon 4 in which the medical fluid is not discharged to the space 9 (initial state) to a state where the medical fluid is discharged to the space 9 to start application of the discharge pressure of the medical fluid to the elastic membrane 6 (local injection-preparing state). In this local injection-preparing state, the elastic membrane 6 expands by using the discharge pressure of the medical fluid, and allows the injection needle 5 to slide up to a state immediately before projecting from the casing 2. In the state immediately before projecting from the casing 2, opening in the injection needle 5 near the proximal end is positioned inside the needle accommodating unit 7, thereby cutting off the communicated state between the space 9 and the channel 5a.

The discharge pressure P of the medical fluid applied to the elastic membrane 6 changes, as shown in FIG. 3, with the passage of time t when the contraction of the balloon 4 is executed. For example, the discharge pressure P increases up to a predetermined threshold $P_{th}$ in the local injection-preparing state. The threshold $P_{th}$ is a discharge pressure required for projecting the injection needle 5 from the casing 2 by the elastic membrane 6. In other words, the elastic membrane 6 can project the injection needle 5 from the casing 2, when the discharge pressure P equal to or higher than the threshold $P_{th}$ is applied.

Thereafter, the balloon 4 further discharges the medical fluid into the space 9 by continuing the contraction, to further increase the discharge pressure P. When the discharge pressure P equal to or higher than the threshold $P_{th}$ is applied due to the contraction of the balloon 4, the elastic membrane 6 expands further to project the injection needle 5 from the casing 2, so that the space 9 and the channel 5a communicate with each other. In this case, the body-insertable apparatus 1 changes the state, as shown in FIG. 5, from the above local injection-preparing state to a state where the injection needle 5 is pierced to the affected part 100 to inject the medical fluid to the affected part 100 (local injection state). Specifically, in the local injection state, the injection needle 5 slides along the guide 2b due to the expansion of the elastic membrane 6, projects from the casing 2, and pierces the affected part 100. Simultaneously therewith, the balloon 4 continues contraction, so that the medical fluid is injected to the affected part 100 via the channel 5a. By continuing contraction, the balloon 4 injects the medical fluid in a desired amount to the affected part 100. In such a local injection state, the discharge pressure P increases, as shown in FIG. 3, until the desired amount of medical fluid is injected to the affected part 100, and is maintained at the level equal to or higher than the threshold $P_{th}$.

When the desired amount of medical fluid is injected to the affected part 100, the balloon 4 gradually decreases the elastic force (that is, the contraction force) accompanying continuation of the contraction. When the desired amount of medical fluid is injected, the discharge pressure P starts to decrease gradually, as shown in FIG. 3, up to the threshold $P_{th}$. The balloon 4 finishes the discharge of the desired amount of medical fluid, and substantially loses the contraction force, and gradually stops the medical-fluid discharge operation.

The elastic membrane 6 expanded for projecting the injection needle 5 contracts by using the elastic force, with a decrease of the discharge pressure P, so that the injection needle 5 slides in a direction to be stored in the casing 2. Thereafter, the discharge pressure P decreases to less than the threshold $P_{th}$, with a decrease of the contraction force of the balloon 4, as shown in FIG. 3. In this case, the body-insertable apparatus 1 changes the state, as shown in FIG. 6, from the local injection state to a local injection-completed state. In the local injection-completed state, the elastic membrane 6 has a high elastic force as compared to the discharge pressure P, and the elastic membrane 6 uses this elastic force to pull the injection needle 5 out from the affected part 100 and store the injection needle 5 up to the end of the sharp point in the casing 2. The thus stored injection needle 5 slides along the guide 2b, so that the opening near the proximal end is inside the needle accommodating unit 7. As a result, the communicated state between the space 9 and the channel 5a is cut off, and the balloon 4 completes the medical-fluid discharge operation. In this manner, the body-insertable apparatus 1 accomplishes the series of operations until the medical fluid has been injected to the desired region in the subject.

As explained above, in the first embodiment of the present invention, the injection needle is provided so as to penetrate substantially the center of the expandable elastic membrane, so that the injection needle slides due to the expansion and contraction of the elastic membrane. When the discharge pressure of the medical fluid is applied to the elastic membrane holding the injection needle in this manner, the elastic membrane expands by using the discharge pressure of the medical fluid, and projects the injection needle from the casing. Therefore, it is not necessary to consume new driving power for executing the projection operation of the injection needle, thereby realizing the body-insertable apparatus that can execute the projection operation of the injection needle in a power saving manner.

The elastic membrane holding the injection needle in this manner generates the elastic force (contraction force) accompanying the expansion operation, and when the applied discharge pressure of the medical fluid decreases to less than the elastic force, the elastic membrane uses the elastic force to store the injection needle in the casing. Accordingly, it is not necessary to consume new driving power for executing the storing operation of the injection needle, thereby realizing the body-insertable apparatus that can execute the storing operation of the injection needle in a power saving manner.

Further, by adopting such a configuration, a new drive mechanism for executing the projection operation of the injection needle need not be provided, and hence the drive mechanism for injecting the medical fluid to the desired region in the subject can be simplified, thereby realizing a downsized body-insertable apparatus easily.

Further, a new drive mechanism for executing the storing operation of the injection needle need not be provided, and hence the drive mechanism for storing the injection needle after injecting the medical fluid to the desired region in the subject can be simplified, thereby realizing the downsized body-insertable apparatus easily. The body-insertable apparatus that can store the injection needle in the casing can prevent that other regions in the subject are damaged by the injection needle.

Further, the storage chamber of the medical fluid is formed by using the expandable balloon, the volume of the storage chamber is reduced by using the contraction force of the balloon to pressurize the medical fluid, and the medical-fluid discharge operation is executed by the contraction operation of the balloon. Therefore, it is not necessary to consume new driving power for executing the medical-fluid discharge operation, thereby promoting power saving of the body-insertable apparatus according to the present invention.

The body-insertable apparatus adopting such a configuration can realize downsizing of the apparatus and can include the local injection function for injecting the medical fluid to the desired region in the subject. Accordingly, the body-insertable apparatus can execute the local injection operation from projecting the injection needle to inject the medical fluid to the desired region in the subject until the injection needle is stored, with less power consumption.

First Modification of First Embodiment

A first modification of the body-insertable apparatus 1 according to the first embodiment of the present invention is explained next. In the first embodiment, the medical-fluid discharge operation is performed by the contraction operation of the balloon. However, in the first modification of the first embodiment, a piston mechanism that pressurizes the medical fluid by reducing the volume of the medical fluid storage chamber is provided, and the medical-fluid discharge operation is performed by driving the piston mechanism.

Figure 7:
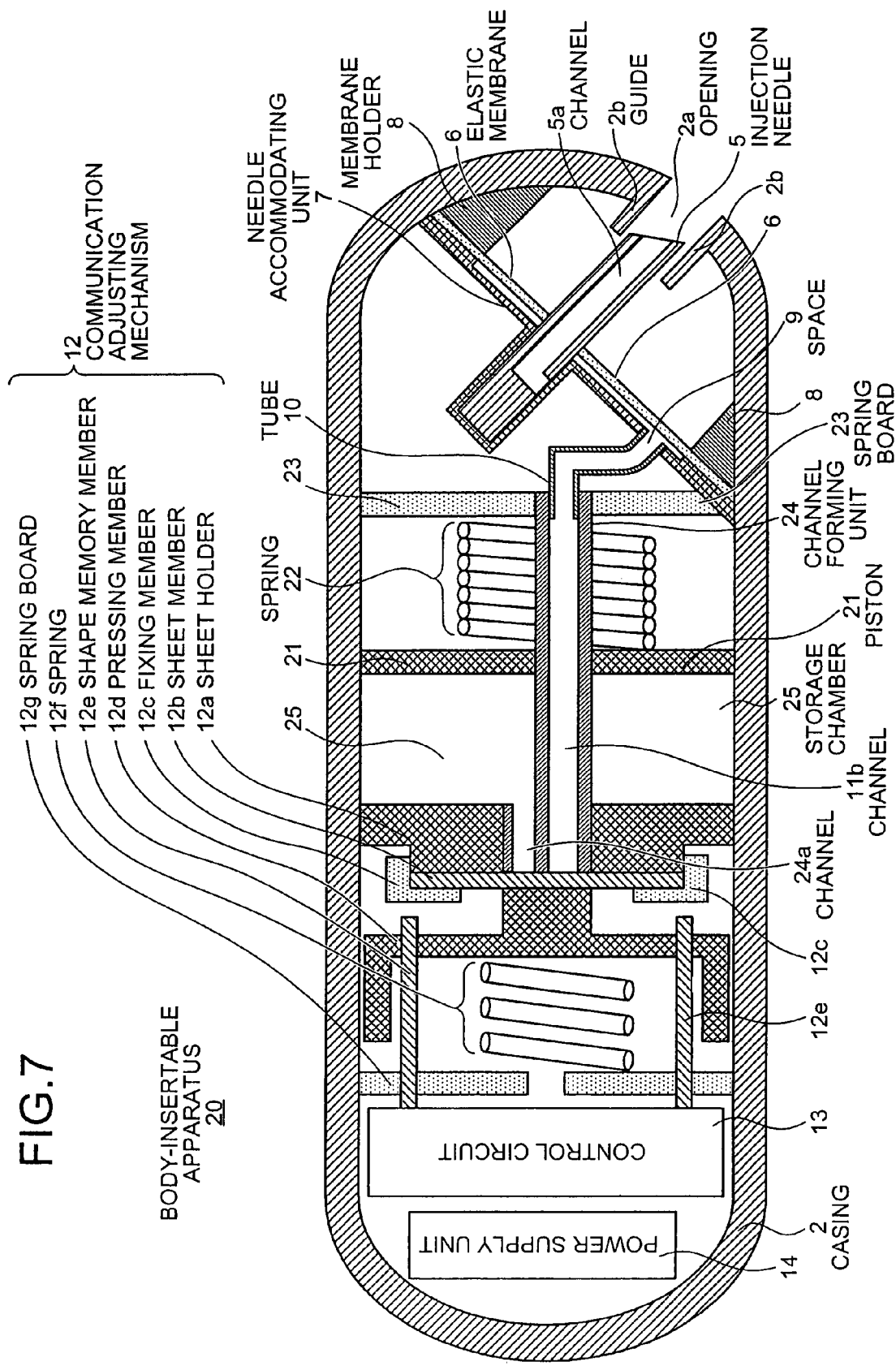
FIG. 7 is a schematic sectional view schematically showing one configuration example of the body-insertable apparatus, which is a first modification of the first embodiment according to the present invention.

FIG. 7 is a schematic sectional view schematically showing one configuration example of the body-insertable apparatus, which is the first modification of the first embodiment according to the present invention. As shown in FIG. 7, a body-insertable apparatus 20 includes a piston 21, a spring 22, and a spring board 23 instead of the balloon 4 in the body-insertable apparatus 1 in the first embodiment, and also includes a channel forming unit 24 instead of the channel forming unit 11. Other configurations are the same as those of the first embodiment, and like reference letters or numerals refer to like constituent elements.

A storage chamber 25 stores beforehand the medical fluid as in the storage chamber 3 in the first embodiment. Specifically, the storage chamber 25 is formed in a region surrounded by the sheet holder 12a, the piston 21, and a part of the casing 2 (that is, a portion positioned between the sheet holder 12a and the piston 21).

The piston 21 slides along the inner wall of the casing 2 to reduce the volume of the storage chamber 25. Specifically, when the storage chamber 25 and the injection needle 5 are communicated with each other due to the operation of the communication adjusting mechanism 12 and the operation of the elastic membrane 6, the piston 21 uses a spring force of the spring 22 to slide in a direction of reducing the volume of the storage chamber 25 to pressurize the medical fluid in the storage chamber 25, thereby discharging the medical fluid via the injection needle 5. In other words, the piston 21 functions as the medical fluid pressurizing unit that pressurizes the medical fluid by reducing the volume of the storage chamber 25, to discharge the medical fluid.

The spring 22 generates a driving force for sliding the piston 21 in the direction of reducing the volume of the storage chamber 25. Specifically, the spring 22 is fixed to the spring board 23 at one end, and to the piston 21 at the other end, and maintained in such a state that the spring length is shorter than the natural length. The spring 22 arranged in this manner functions so as to energize the elastic force (spring force) relative to the piston 21 in the direction of reducing the volume of the storage chamber 25. The spring 22 generates the spring force as the driving force of the piston 21.

The piston 21 that reduces the volume of the storage chamber 25, the spring 22 for generating the driving force of the piston 21, the spring board 23 holding the spring 22, and a part of the casing 2 in which the piston 21 slides (a part of the casing 2 positioned between the piston 21 and the sheet holder 12a) constitute the piston mechanism that reduces the volume of the storage chamber to pressurize the medical fluid, and performs a discharge operation of the medical fluid. In this case, the part of the casing 2 functions as a cylinder in the piston mechanism.

The medical-fluid discharger realized by including the piston mechanism, the tube 10, and the channel forming unit 24 described later reduces the volume of the storage chamber 25 to discharge the medical fluid in the storage chamber 25, and projects the injection needle 5 from the casing 2 by using the physical force for the discharge of the medical fluid (for example, the discharge pressure of the medical fluid). In other words, the medical-fluid discharger functions as a drive source (a drive source for the discharge of the medical fluid) that discharges the medical fluid in the storage chamber 25 and generates the driving force (physical force for the discharge of the medical fluid) for projecting the injection needle 5 from the casing 2.

The channel forming unit 24 and the tube 10 form a first channel connecting to the storage chamber 25 and a second channel connecting to the space 9, which is the injection needle 5 side relative to the storage chamber 25. Specifically, in the channel forming unit 24, channels 24a and 24b are formed therein, and the tube 10 is fitted thereto in such a manner that the channel 24b and the space 9 are communicated with each other. In this case, the channel 24a forms the first channel connecting to the storage chamber 25 and the channel 11b and the tube 10 form the second channel connecting to the space 9. The channel forming unit 24 is provided, as shown in FIG. 7, in such a manner that the channel forming unit 24 penetrate the sheet holder 12a, the piston 21, and the spring board 23. In this case, one end of the channel forming unit 24 (the side where the channel 24a is formed) is exposed on the sheet holder 12a, as in the case of the channel forming unit 11, and the communicated state of the channels 24a and 24b is adjusted by the communication adjusting mechanism 12 and the control circuit 13.

The body-insertable apparatus 20 adopting such a configuration can have the same function as that of the body-insertable apparatus 1 according to the first embodiment. For example, the body-insertable apparatus 20 can project the injection needle 5 by the discharge pressure of the medical fluid, as in the body-insertable apparatus 1. The body-insertable apparatus 20 can obtain the same operations and effects as those of the body-insertable apparatus 1.

Second Modification of First Embodiment

A second modification of the body-insertable apparatus 1 according to the first embodiment of the present invention is explained next. In the first embodiment, start or suspension of the medical-fluid discharge operation is controlled by the operation of the communication adjusting mechanism 12. However, in the second modification of the first embodiment, a piston mechanism for reducing the volume of the medical fluid storage chamber under the control of the control circuit 13 to pressurize the medical fluid is provided, and the medical-fluid discharge operation is performed by driving the piston mechanism.

Figure 8:
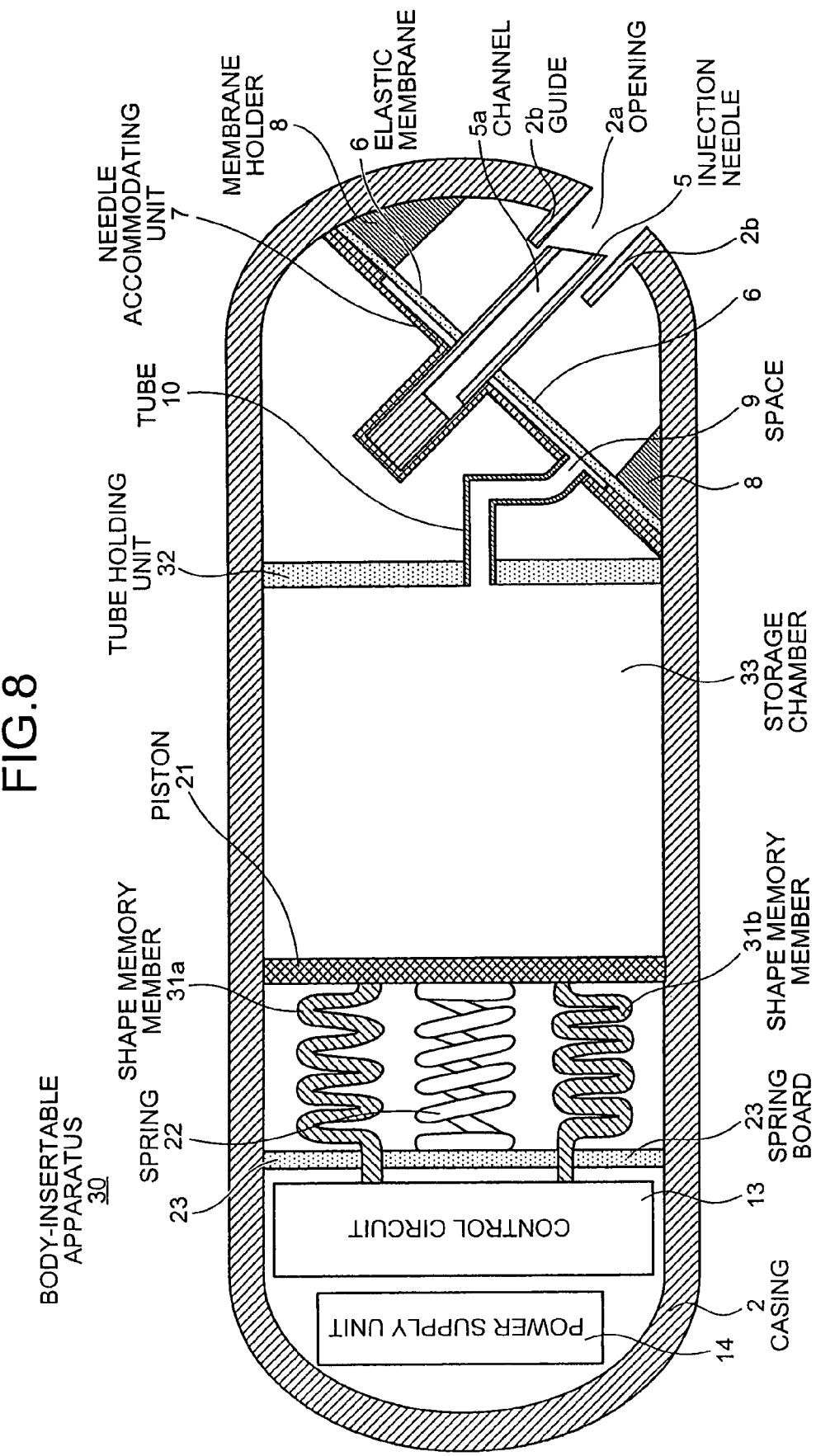
FIG. 8 is a schematic sectional view schematically showing one configuration example of the body-insertable apparatus, which is a second modification of the first embodiment according to the present invention.

FIG. 8 is a schematic sectional view schematically showing one configuration example of the body-insertable apparatus, which is the second modification of the first embodiment according to the present invention. As shown in FIG. 8, a body-insertable apparatus 30 includes shape memory members 31a and 31b for controlling start or suspension of sliding of the piston 21 instead of the communication adjusting mechanism 12 in the body-insertable apparatus 20, which is the first modification of the first embodiment. The body-insertable apparatus includes the spring board 23 so as to hold one end of the shape memory members 31a and 31b and the spring 22. The body-insertable apparatus 30 does not include the channel forming unit 11. Other configurations are the same as those of the first modification of the first embodiment, and like reference letters or numerals refer to like constituent elements.

A storage chamber 33 stores beforehand the medical fluid as in the storage chamber 3 in the first embodiment. Specifically, the storage chamber 33 is formed in a region surrounded by the piston 21, a tube holding unit 32, and a part of the casing 2 (that is, a portion positioned between the piston 21 and the tube holding unit 32).

The piston 21 provided in the body-insertable apparatus 30 slides along the inner wall of the casing 2 to reduce the volume of the storage chamber 33. Specifically, when the storage chamber 33 and the injection needle 5 are communicated with each other due to the operation of the shape memory member 31a and the operation of the elastic membrane 6, the piston 21 uses a spring force of the spring 22 to slide in a direction of reducing the volume of the storage chamber 33 to pressurize the medical fluid in the storage chamber 33, thereby discharging the medical fluid via the injection needle 5.

The spring 22 provided in the body-insertable apparatus 30 generates a driving force (spring force) for sliding the piston 21 in the direction of reducing the volume of the storage chamber 33. The shape memory members 31a and 31b are for controlling start or suspension of sliding of the piston 21 to the storage chamber 33. The spring 22 and the shape memory members 31a and 31b are fixed to the spring board 23 at one end and to the piston 21 at the other end, respectively. In this case, the spring 22 is maintained in such a state that the spring length is shorter than the natural length, and functions so as to energize the elastic force (spring force) relative to the piston 21 in the direction of reducing the volume of the storage chamber 33.

The shape memory members 31a and 31b has a cylindrical or coiled (for example, SMA coil) structure, and is formed of a shape memory alloy having a predetermined shape memory characteristic and a predetermined electrical resistivity. In this case, the shape memory members 31a and 31b have a length capable of counteracting the spring force by the spring 22 under the same temperature condition as the temperature inside the subject, and act so as to stop sliding of the piston 21. On the other hand, under a predetermined temperature condition, for example, a temperature condition sufficiently higher than the temperature inside the subject, the shape memory members 31a and 31b change the shape thereof so as to have a sufficient length to energize the spring force by the spring 22 to the piston 21, and act so as to start sliding of the piston 21 to the storage chamber 33.

The tube holding unit 32 is set, as shown in FIG. 8, near the needle accommodating unit 7, of the inner wall of the casing 2, in a manner facing the piston 21, and the tube 10 is inserted into the opening thereof and held. The tube 10 held by the tube holding unit 32 communicates with the storage chamber 33 and the space 9.

The piston mechanism of the body-insertable apparatus 30 is realized by using the piston 21, the spring 22, the shape memory members 31a and 31b, the tube holding unit 32, and a part of the casing 2. The medical-fluid discharger realized by including such a piston mechanism and the tube 10 reduces the volume of the storage chamber 33 to discharge the medical fluid in the storage chamber 33, and projects the injection needle 5 from the casing 2 by using the physical force for the discharge of the medical fluid (for example, the discharge pressure of the medical fluid). In other words, the medical-fluid discharger functions as a drive source (a drive source for the discharge of the medical fluid) that discharges the medical fluid in the storage chamber 33 and generates the driving force (physical force for the discharge of the medical fluid) for projecting the injection needle 5 from the casing 2.

The control circuit 13 provided in the body-insertable apparatus 30 generates the Joule heat by supplying predetermined current to the shape memory members 31a and 31b, to raise the temperature of the shape memory members 31a and 31b to higher than a predetermined temperature. As a result, the control circuit 13 controls so that the shape of the shape memory members 31a and 31b is changed to start sliding of the piston 21. According to such control for starting sliding, the control circuit 13 can start the medical-fluid discharge operation by the piston 21. On the other hand, the control circuit 13 decreases the temperature of the shape memory members 31a and 31b to lower than the predetermined temperature. As a result, the control circuit 13 controls so that the shape memory members 31a and 31b resumes the original shape, to stop sliding of the piston 21. According to such control for stopping sliding, the control circuit 13 can stop (suspend) the medical-fluid discharge operation by the piston 21.

The body-insertable apparatus 30 adopting such a configuration can have the same function as that of the body-insertable apparatus 1 according to the first embodiment. Further, the body-insertable apparatus 30 can control start and stop of the medical-fluid discharge operation without using the channel forming unit 11 and the communication adjusting mechanism 12, thereby simplifying the discharge operation mechanism of the medical fluid (that is, the piston mechanism) and the control mechanism. Therefore, the body-insertable apparatus 20 can obtain the same operations and effects as those of the body-insertable apparatus 1, and the apparatus can be downsized.

Second Embodiment

A second embodiment of the present invention is explained next. In the first embodiment, the discharge pressure of the medical fluid is applied to the elastic membrane 6 holding the injection needle 5, to project the injection needle 5. However, in the second embodiment, the injection needle is provided in a cylindrical guide, and the discharge pressure of the medical fluid is applied to a rear end of the injection needle, so as to push out the injection needle.

Figure 9:
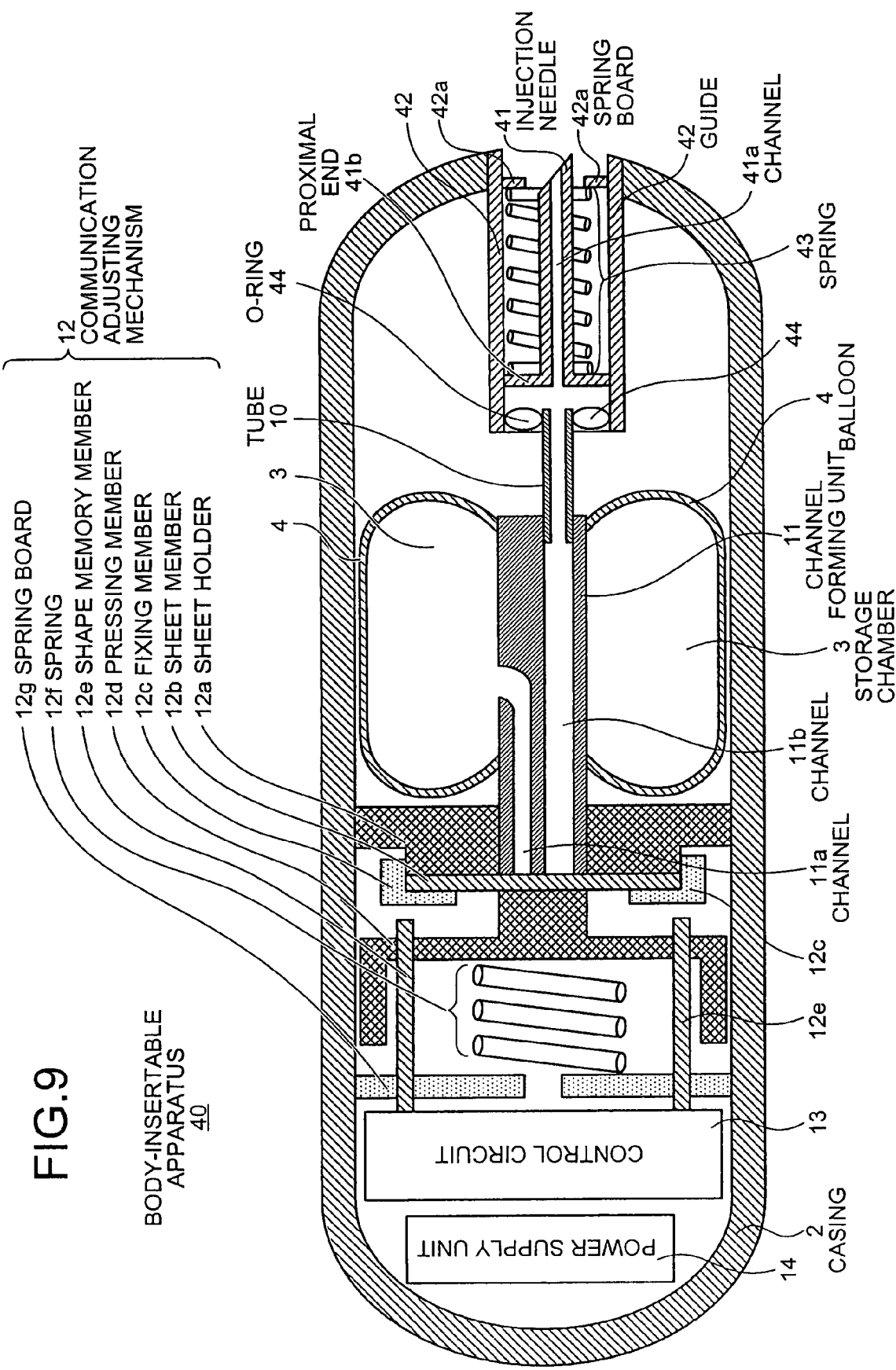
FIG. 9 is a schematic sectional view schematically showing one configuration example of a body-insertable apparatus according to a second embodiment of the present invention.

FIG. 9 is a schematic sectional view schematically showing one configuration example of the body-insertable apparatus according to the second embodiment of the present invention. As shown in FIG. 9, a body-insertable apparatus 40 includes a cylindrical guide 42 instead of the guide 2b in the body-insertable apparatus 1 according to the first embodiment, and an injection needle 41 is provided inside the guide 42, instead of the injection needle 5. A spring 43 is provided in the injection needle 41 instead of the elastic membrane 6. On the other hand, the body-insertable apparatus 40 does not include the needle accommodating unit 7 and the membrane holder 8, but includes the tube 10 so that the channel 11b is communicated with a rear end of the guide 42. Other configurations are the same as those of first embodiment, and like reference letters or numerals refer to like constituent elements.

The injection needle 41 projects from the casing 2 by using a predetermined drive source for the discharge of the medical fluid, and injects the medical fluid to the desired region in the subject, like the injection needle 5. Specifically, the injection needle 41 has a channel 41a formed therein for connecting the distal end side inserted into the subject to the rear end, and a brim-shaped proximal end 41b is formed at the rear end. The injection needle 41 is slidably arranged in the inner space of the cylindrical guide 42. In this case, the proximal end 41b and the inner wall of the guide 42 engages with each other, and as shown in FIG. 9, the proximal end 41b slides on the inner wall of the guide 42. That is, the proximal end 41b functions as a piston sliding on the inner wall of the cylindrical guide 42. When the discharge pressure of the medical fluid is applied to the rear end, the injection needle 41 having such a proximal end 41b formed therein slides along the guide 42 due to the discharge pressure of the medical fluid to project, and discharges the medical fluid from the distal end via the channel 41a.

The guide 42 regulates the sliding direction of the injection needle 41, and projects the injection needle 41 from the casing 2 by using the discharge pressure of the medical fluid. Specifically, the guide 42 has the cylindrical structure, and is provided at a predetermined position of the casing 2, for example, near the distal end. The guide 42 further includes a frame-like spring board 42a having an opening through which the injection needle 41 can pass through, on the distal end side (on the entrance side of the injection needle), and with the tube 10 on the rear end side via an O-ring 44. The guide 42 can keep watertight relative to the inside of the casing 2 by the O-ring 44.

The spring 43 is arranged in the guide 42 in an area between the proximal end 41b of the injection needle 41 and the spring board 42a. The spring 43 stores the injection needle 41 projected from the casing 2 in the casing 2. Specifically, the spring 43 is fixed to the spring board 42a at one end and to the proximal end 41b at the other end, and arranged such that when the injection needle 41 is stored in the casing 2, the spring length becomes the natural length. This spring 43 generates the elastic force (spring force) for sliding the injection needle 41 in the projecting direction and returning the injection needle 41 into the casing 2.

The medical-fluid discharger realized by including the guide 42, the balloon 4, the tube 10, and the channel forming unit 11 discharges the medical fluid in the storage chamber 3 by reducing the volume of the storage chamber 3, and projects the injection needle 41 from the casing 2 by using the physical force for the discharge of the medical fluid (for example, the discharge pressure of the medical fluid). In other words, the medical-fluid discharger functions as a drive source (drive source for the discharge of the medical fluid) that discharges the medical fluid in the storage chamber 3, and generates a driving force (physical force for the discharge of the medical fluid) for projecting the injection needle 41 from the casing 2.

Figure 10:
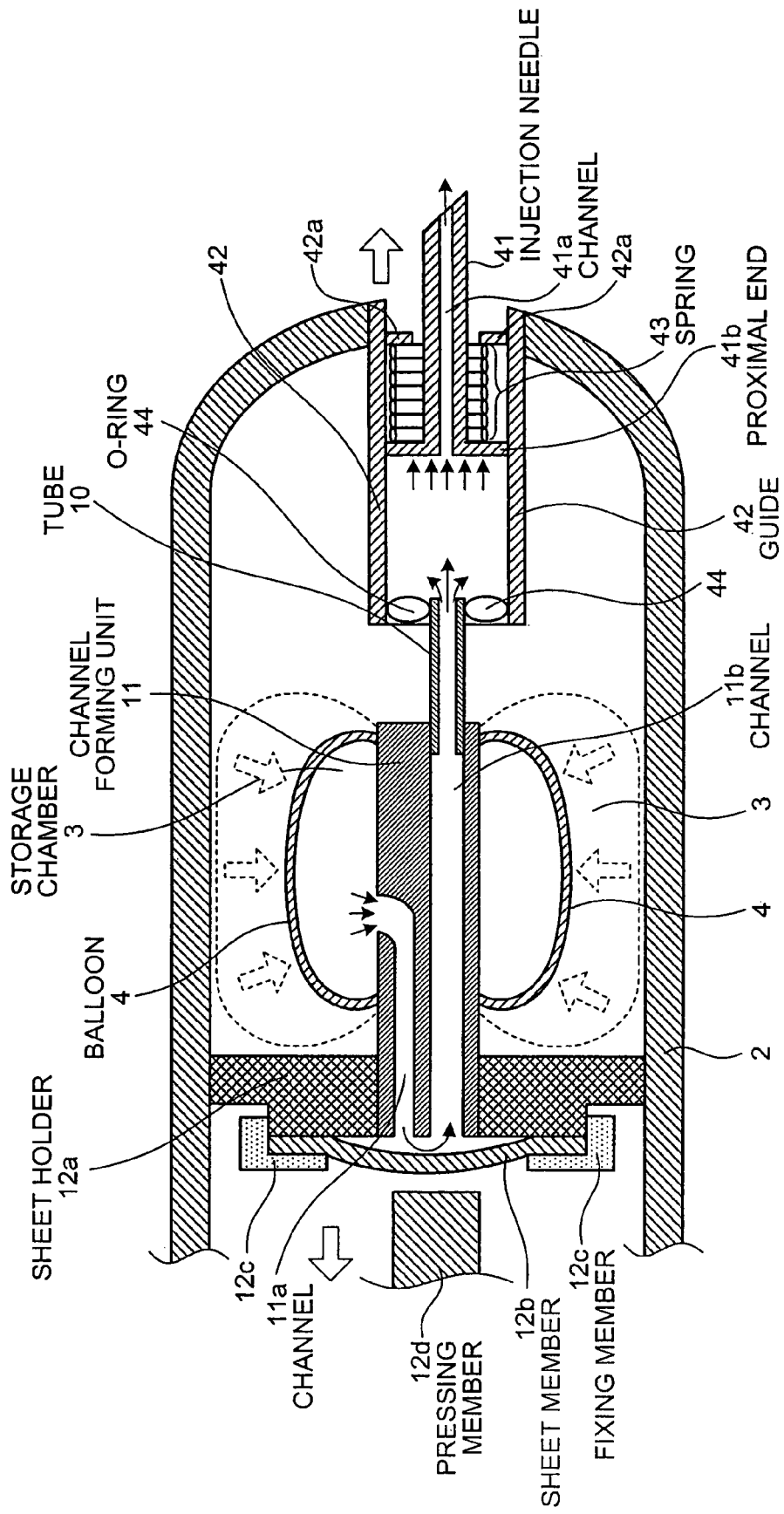
FIG. 10 is a schematic sectional view schematically exemplifying a projected state of the injection needle by applying the discharge pressure of the medical fluid to a rear end face of the injection needle.

An operation of the body-insertable apparatus 40 is explained next. FIG. 10 is a schematic sectional view schematically exemplifying a projected state of the injection needle 41 from the casing 2 by applying a discharge pressure of the medical fluid to the rear end of the injection needle 41. The projection operation of the injection needle 41 and the medical-fluid discharge operation are explained with reference to FIG. 10.

The control circuit 13 performs drive control of the communication adjusting mechanism 12, to release the adhesion state between the sheet member 12b and the end of the channel forming unit 11. Due to the operation of the channel forming unit 11, the channels 11a and 11b are communicated with each other, and the balloon 4 starts the contraction to execute the medical-fluid discharge operation. In this case, the medical fluid in the storage chamber 3 is discharged into the guide 42, specifically, to a rear end face of the injection needle 41 via the channels 11a and 11b and the tube 10, and further discharged from the distal end of the injection needle 41 via the channel 41a.

By discharging the medical fluid into the guide 42, the balloon 4 applies the discharge pressure of the medical fluid to the rear end face of the injection needle 41, and at the same time, discharges the medical fluid from the distal end of the injection needle 41 via the channel 41a. The discharge pressure of the medical fluid changes (increases or decreases) in the same manner as, for example, in the case shown in FIG. 3, accompanying continuation of the contraction operation of the balloon 4. When the discharge pressure of the medical fluid is equal to or higher than the elastic force of the spring 43, the injection needle 41 is pressed at the rear end face by the discharge pressure of the medical fluid, and slides in the guide 42, to project from the casing 2. Thus, by projecting the injection needle 41 and discharging the medical fluid by using the discharge pressure of the medical fluid, the body-insertable apparatus 40 can insert the injection needle 41 to the desired region in the subject to inject the medical fluid to the desired region.

On the other hand, when having discharged the medical fluid in a predetermined amount or more, or when the communicated state between the channels 11a and 11b is cut off, the balloon 4 stops contraction, to gradually decrease the discharge pressure of the medical fluid to be applied to the rear end face of the injection needle 41. The spring 43 generates the elastic force with the projection operation of the injection needle 41. When the discharge pressure of the medical fluid decreases to less than the elastic force, the spring 43 slides the injection needle 41 toward the casing 2 by the elastic force, and stores the injection needle 41 inserted into, for example, the desired region in the subject, in the casing 2.

The body-insertable apparatus 40 adopting such a configuration has substantially the same function as that of the body-insertable apparatus 1 according to the first embodiment, and for example, can project the injection needle 41 by using the discharge pressure of the medical fluid, and house the injection needle 41 in the casing 2 by using the elastic force of the spring 43. Further, since the body-insertable apparatus 40 applies the discharge pressure of the medical fluid discharged into the cylindrical guide 42 to the rear end face of the injection needle 41 to project the injection needle 41, and uses the elastic force of the spring 43 arranged in the guide 42 to house the injection needle 41 in the casing 2, the space for expanding the elastic membrane 6 need not be formed in the casing 2. Therefore, space saving can be further achieved in the casing 2, and the body-insertable apparatus 40 can obtain the same operations and effects as those of the body-insertable apparatus 1, and the apparatus size can be downsized.

First Modification of Second Embodiment

A first modification of the body-insertable apparatus 40 according to the second embodiment of the present invention is explained next. In the second embodiment, the injection needle 41 slides inside the cylindrical guide 42, however, in the first modification of the second embodiment, an extensible bellows tube is provided at a rear end of the injection needle 41, and the bellows tube is extended or contracted corresponding to projection or storage of the injection needle 41.

Figure 11:
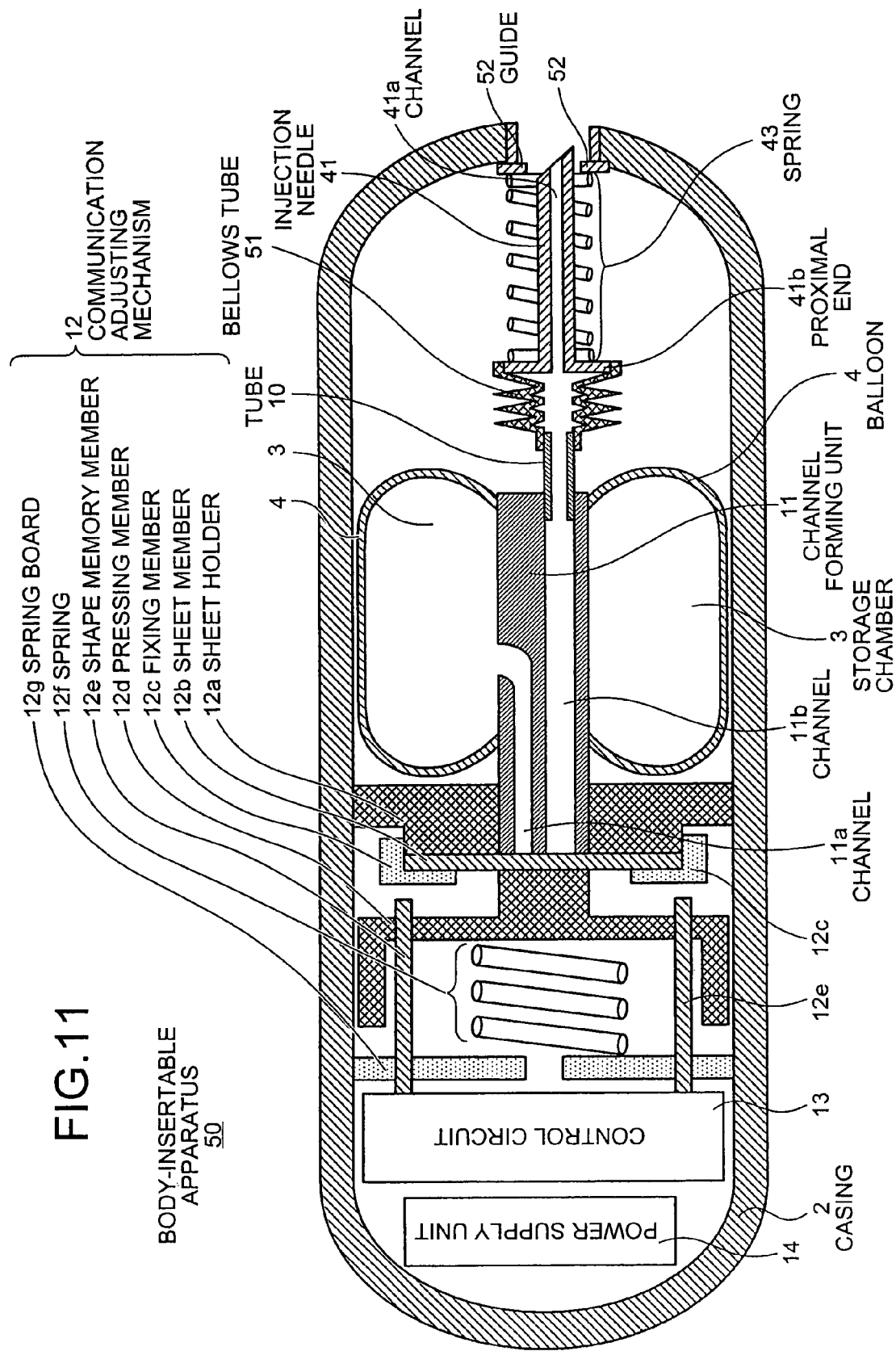
FIG. 11 is a schematic sectional view schematically showing one configuration example of the body-insertable apparatus, which is a first modification of the second embodiment according to the present invention.

FIG. 11 is a schematic sectional view schematically showing one configuration example of the body-insertable apparatus, which is the first modification of the second embodiment according to the present invention. As shown in FIG. 11, a body-insertable apparatus 50 includes a guide 52 instead of the guide 42 in the body-insertable apparatus 40 according to the second embodiment. The body-insertable apparatus 50 also includes a bellows tube 51 for connecting the tube 10 with the channel 41a at the proximal end 41b of the injection needle 41. Other configurations are the same as those of the second embodiment, and like reference letters or numerals refer to like constituent elements.

The bellows tube 51 discharges the medical fluid to the rear end face of the injection needle 41 and the channel 41a without impairing the projection operation and storing operation of the injection needle 41. Specifically, the bellows tube 51 is an extensible tube having a bellows structure, and as shown in FIG. 11, one end thereof is connected to the proximal end 41b and the other end is connected to the tube 10. The bellows tube 51 arranged in this manner connects the channel 11b with the channel 41a in the injection needle 41 via the tube 10, and extends or contracts corresponding to sliding of the injection needle 41. In this case, the bellows tube 51 maintains the communicated state between the channel 11b and the channel 41a without impairing the projection operation and storing operation of the injection needle 41, by the extending or contracting operation. The bellows tube 51 can be directly fitted to the channel forming unit 11. In this case, the bellows tube 51 connects the channel 11b with the channel 41a in the injection needle 41 not via the tube 10.

The guide 52 regulates the direction of putting in and out the injection needle 41. Specifically, the guide 52 has a substantially recessed structure, and an opening for putting in and out the injection needle 41 is formed on a bottom thereof. As shown in FIG. 11, the guide 52 is provided at an entrance for the injection needle 41 in the casing 2, and one end of the spring 43 is fitted thereto. The thus arranged guide 52 regulates the direction of putting in and out the injection needle 41, and the injection needle 41 can be put in and out smoothly according to the regulation.

The medical-fluid discharger realized by including the bellows tube 51, the guide 52, the balloon 4, the tube 10, and the channel forming unit 11 discharges the medical fluid in the storage chamber 3 by reducing the volume of the storage chamber 3, and projects the injection needle 41 from the casing 2 by using the physical force for the discharge of the medical fluid (for example, the discharge pressure of the medical fluid). In other words, the medical-fluid discharger functions as a drive source (drive source for the discharge of the medical fluid) that discharges the medical fluid in the storage chamber 3, and generates a driving force (physical force for the discharge of the medical fluid) for projecting the injection needle 41 from the casing 2.

Figure 12:
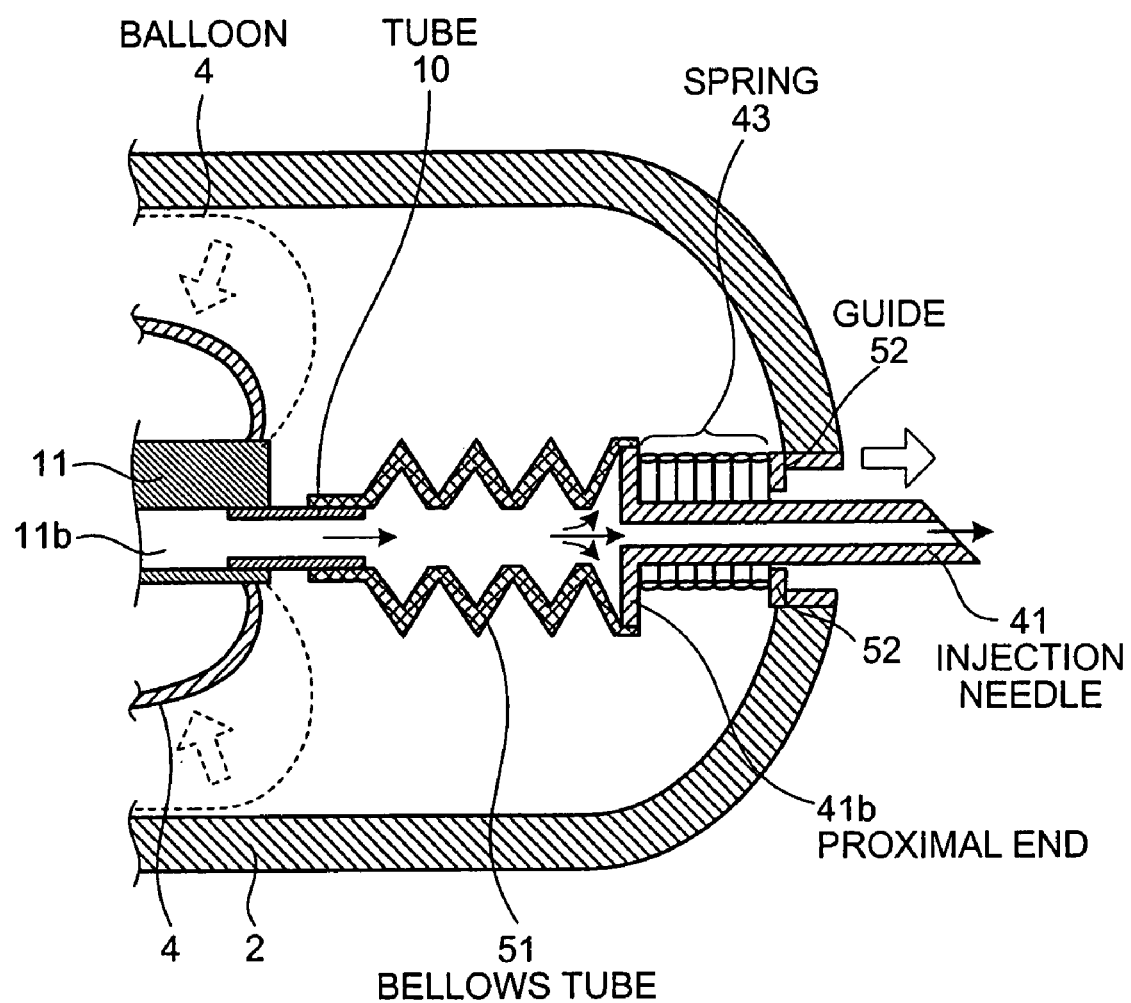
FIG. 12 is a schematic sectional view schematically exemplifying another projected state of the injection needle by applying the discharge pressure of the medical fluid to a rear end face of the injection needle.

An operation of the body-insertable apparatus 50 is explained next. FIG. 12 is a schematic sectional view schematically exemplifying another projected state of the injection needle 41 from the casing 2 by applying a discharge pressure of the medical fluid to the rear end of the injection needle 41. The projection operation of the injection needle 41 and the medical-fluid discharge operation accompanying the extension and contraction of the bellows tube 51 are explained with reference to FIG. 12.

The balloon 4 starts contraction based on the operation of the communication adjusting mechanism 12, to execute the medical-fluid discharge operation, as in the second embodiment, and discharges the medical fluid into the bellows tube 51 via the channels 11a and 11b and the tube 10. When the medical fluid reaches the rear end face of the injection needle 41, the balloon 4 applies the discharge pressure of the medical fluid to the rear end face of the injection needle 41, to discharge the medical fluid from the distal end of the injection needle 41 via the channel 41a.

The discharge pressure of the medical fluid changes (increases or decreases) in the same manner as in the second embodiment. When the discharge pressure of the medical fluid is equal to or higher than the elastic force of the spring 43, the injection needle 41 is pressed at the rear end face by the discharge pressure of the medical fluid, and projects via the opening in the guide 52. At the same time, the bellows tube 51 extends as shown in FIG. 12, to maintain the communicated state between the channel 11b and the channel 41a without impairing the projection operation of the injection needle 41. Thus, by projecting the injection needle 41 and discharging the medical fluid by using the discharge pressure of the medical fluid, the body-insertable apparatus 50 can insert the injection needle 41 to the desired region in the subject to inject the medical fluid to the desired region.

On the other hand, the balloon 4 gradually decreases the discharge pressure of the medical fluid as in the second embodiment. Accordingly, when the discharge pressure of the medical fluid decreases to less than the elastic force, the spring 43 allows the injection needle 41 inserted into the desired region in the subject to be stored in the casing 2 by the elastic force. At the same time, the bellows tube 51 contracts corresponding to the storing operation of the injection needle 41, and maintains the communicated state between the channel 11b and the channel 41a without impairing the storing operation of the injection needle 41.

The body-insertable apparatus 50 adopting such a configuration has substantially the same function as that of the body-insertable apparatus 40 according to the second embodiment. The body-insertable apparatus 50 is configured such that the bellows tube 51 is freely extended or contracted corresponding to the projection operation or the storing operation of the injection needle 41. Therefore, a drive mechanism for putting in and out the injection needle 41 can be simplified, thereby enabling further space saving inside the casing 2. The body-insertable apparatus 50 can obtain the same operations and effects as those of the body-insertable apparatus 40, and the apparatus size can be downsized.

Second Modification of Second Embodiment

A second modification of the body-insertable apparatus 40 in the second embodiment of the present invention is explained next. In the second embodiment, the medical-fluid discharge operation is performed by the contraction of the balloon, however, in the second modification of the second embodiment, a piston mechanism like the one in the first modification of the first embodiment is provided, and the medical-fluid discharge operation is performed by driving the piston mechanism.

Figure 13:
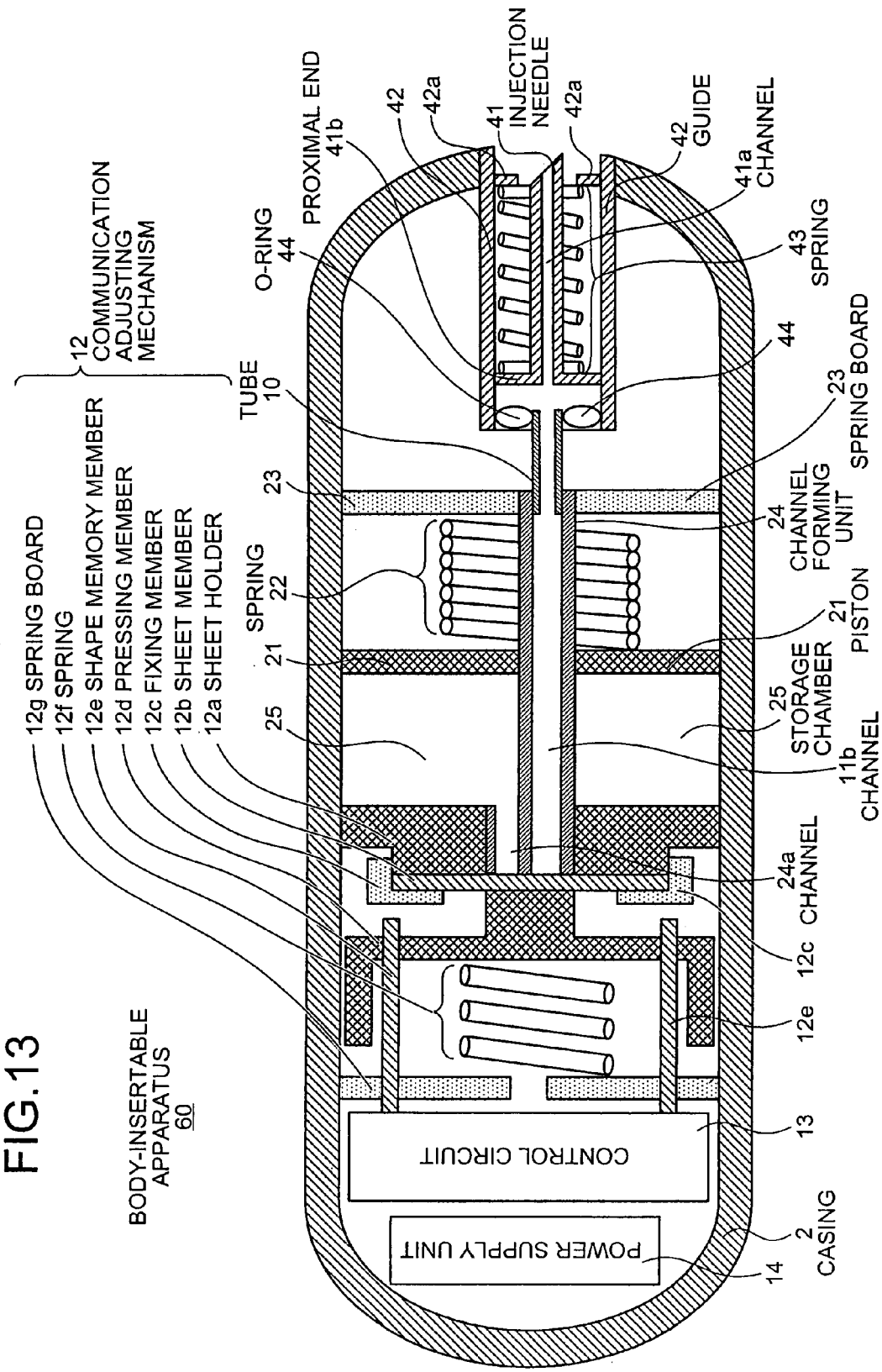
FIG. 13 is a schematic sectional view schematically showing one configuration example of the body-insertable apparatus, which is a second modification of the second embodiment according to the present invention.

FIG. 13 is a schematic sectional view schematically showing one configuration example of the body-insertable apparatus, which is the second modification of the second embodiment according to the present invention. As shown in FIG. 13, a body-insertable apparatus 60 includes the piston 21 and the spring board 23 instead of the balloon 4 of the body-insertable apparatus 40 according to the second embodiment, and a channel forming unit 24 is provided therein instead of the channel forming unit 11. Other configurations are the same as those of the second embodiment, and like reference letters or numerals refer to like constituent elements.

The piston 21, the spring 22, the spring board 23, and a part of the casing 1 along which the piston 21 slides (a part of the casing 2 positioned between the piston 21 and the sheet holder 12a) constitute the piston mechanism like the one in the body-insertable apparatus 20, which is the first modification of the first embodiment. That is, the spring 22 is fixed to the spring board 23 at one end, and to the piston 21 at the other end, and generates a driving force (spring force) for the piston 21. The piston 21 slides by using the spring force of the spring 22, thereby reducing the volume of the storage chamber 25 to pressurize the medical fluid. Such a piston mechanism performs a discharge operation of the medical fluid based on respective operations of the piston 21 and the spring 22. According to the discharge operation, the medical fluid in the storage chamber 25 is discharged into the guide 42 via the channel 24a, the tube 10, and the guide 42.

The medical-fluid discharger realized by including the piston mechanism, the guide 42, the tube 10, and the channel forming unit 24 discharges the medical fluid in the storage chamber 25 by reducing the volume of the storage chamber 25, and projects the injection needle 41 from the casing 2 by using the physical force for the discharge of the medical fluid (for example, the discharge pressure of the medical fluid). In other words, the medical-fluid discharger functions as a drive source (drive source for the discharge of the medical fluid) that discharges the medical fluid in the storage chamber 25, and generates a driving force (physical force for the discharge of the medical fluid) for projecting the injection needle 41 from the casing 2.

The body-insertable apparatus 60 adopting such a configuration has substantially the same function as that of the body-insertable apparatus 40 according to the second embodiment, and can obtain the same operations and effects as those of the body-insertable apparatus 40. This applies to the body-insertable apparatus 50 in the first modification of the second embodiment. That is, even when the piston mechanism the same as that of the body-insertable apparatus 20 is provided instead of the balloon 4 of the body-insertable apparatus 50, the same operations and effects as those of a case in which the balloon 4 is provided can be obtained.

Third Embodiment

A third embodiment of the present invention is explained next. In the first embodiment, the injection needle is projected by using the discharge pressure of the medical fluid. In the third embodiment, however, a pressurizing force for pressurizing the medical fluid (for example, the contraction force of the balloon 4) is used for discharging the medical fluid, thereby projecting the injection needle.

Figure 14:
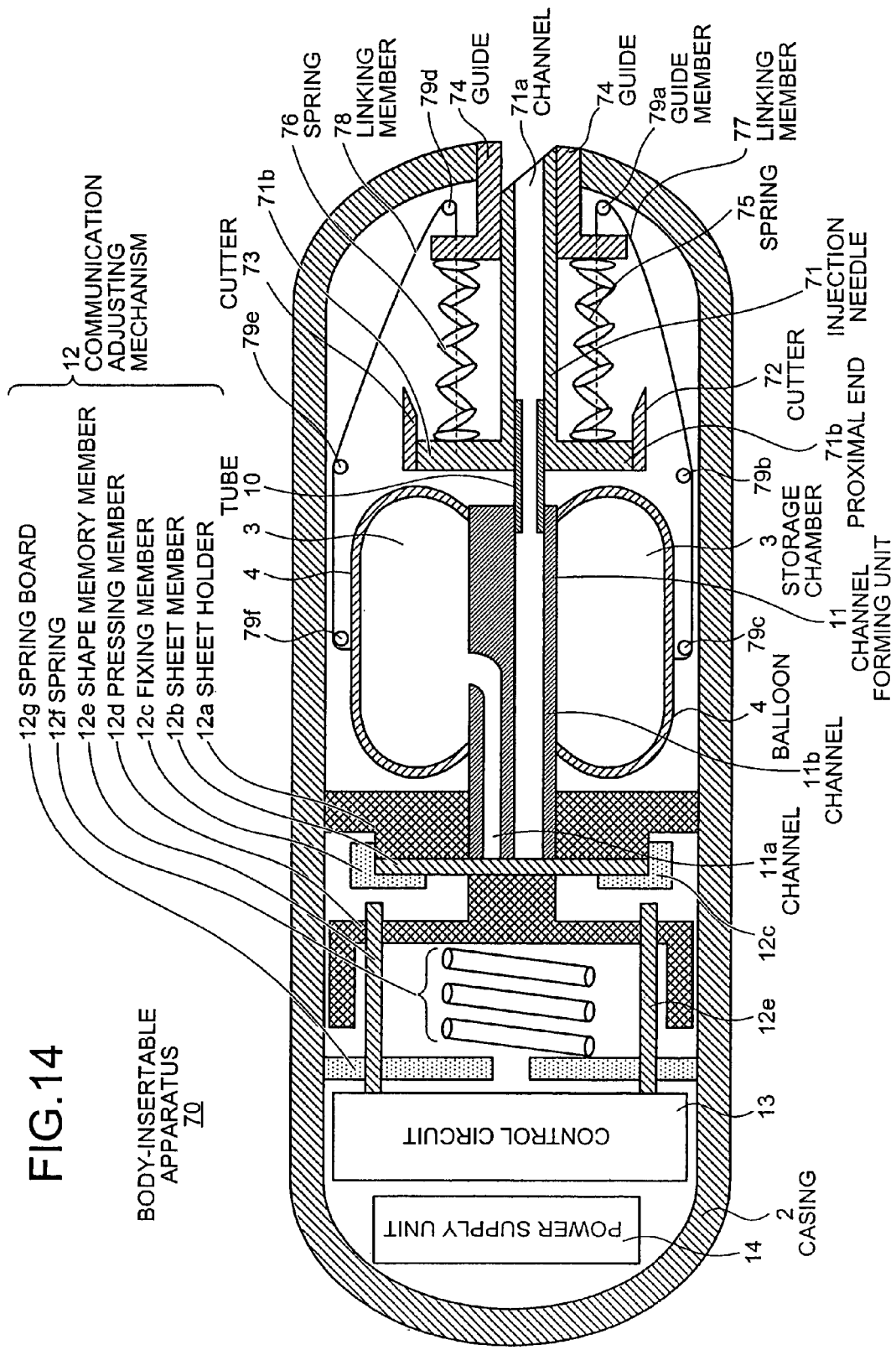
FIG. 14 is a schematic sectional view schematically showing one configuration example of a body-insertable apparatus according to a third embodiment of the present invention.

FIG. 14 is a schematic sectional view schematically showing one configuration example of the body-insertable apparatus according to the third embodiment of the present invention. As shown in FIG. 14, the body-insertable apparatus 70 includes an injection needle 71 instead of the injection needle 5 in the body-insertable apparatus 1 according to the first embodiment, and a guide 74 instead of the guide 2b. The body-insertable apparatus 70 does not include the elastic membrane 6, the needle accommodating unit 7, and the membrane holder 8, but includes springs 75 and 76, linking members 77 and 78 for projecting the injection needle 71 in conjunction with the contraction of the balloon 4, and guide members 79a to 79f for regulating respective paths of the linking members 77 and 78. Other configurations are the same as those of the first embodiment, and like reference letters or numerals refer to like constituent elements.

The injection needle 71 projects from the casing 2 by using a predetermined drive source for the discharge of the medical fluid, to inject the medical fluid to a desired region in the subject, like the injection needle 5. Specifically, the injection needle 71 has a channel 71a formed therein for connecting the distal end side inserted into the subject to the rear end, and a brim-shaped proximal end 71b is formed at the rear end. The tube 10 is slidably inserted into the channel 71a of the injection needle 71. The tube 10 connects the channel 11b to the channel 71a of the injection needle 71. The injection needle 71 includes cutters 72 and 73 at the proximal end 71b.

The cutters 72 and 73 are respectively for cutting the linking members 77 and 78. Specifically, the cutters 72 and 73 are respectively provided at the proximal end 71b so that the linking members 77 and 78 are respectively positioned on a moving line, which moves with the slide of the injection needle 71. When the injection needle 71 slides to a position where the length of the injection needle 71 (projecting length) projected from the casing 2 becomes a predetermined length, the cutters 72 and 73 function to cut the linking members 77 and 77, respectively.

The guide 74 regulates the sliding direction of the injection needle 71. Specifically, the guide 74 has a cylindrical structure, and a brim is formed so as to face the proximal end 71b of the injection needle 71. The guide 74 is provided at an entrance for the injection needle 71 in the casing 2, and regulates the sliding direction of the injection needle 71 to smoothly put in and out the injection needle 71.

The springs 75 and 76 are for storing the injection needle 71 projected from the casing 2 in the casing 2. Specifically, the springs 75 and 76 are respectively fixed to the guide 74 at one end and to the proximal end 71b at the other end. In this case, the springs 75 and 76 are arranged so as to be symmetrical relative to each other, centering on the channel 71a of the injection needle 71. The respective spring length of the springs 75 and 76 is the natural length when the injection needle 71 is stored in the casing 2. Therefore, the springs 75 and 76 contract with the slide of the injection needle 71 in the projecting direction, and generates the elastic force (spring force) accompanying the contraction. The springs 75 and 76 energizes the elastic force in a direction of storing the injection needle 71 in the casing 2.

The linking members 77 and 78 are for performing the projection operation of the injection needle 71, in conjunction with the contraction of the balloon 4 (that is, the medical-fluid discharge operation). Specifically, the linking members 77 and 78 are connected to the proximal end 71b of the injection needle 71 at one end, and to an outer circumference of the balloon 4, to link the balloon 4 and the injection needle 71 to each other. More specifically, as shown in FIG. 14, the linking member 77 passes through the brim of the guide 74 from the proximal end 71b, and reaches the outer circumference of the balloon 4 via the guide members 79a to 79c. Further, the linking member 78 passes through the brim of the guide 74 from the proximal end 71b, and reaches the outer circumference of the balloon 4 via the guide members 79d to 79f. In this case, the linking members 77 and 78 are arranged so as to be positioned substantially opposite to each other.

It is desired that the linking members 77 and 78 be arranged so as to pass near the springs 75 and 76 (for example, near the central axis of the spring in the longitudinal direction). As a result, the springs 75 and 76 and the linking members 77 and 78 can be connected close to each other on the proximal end 71b, thereby enabling downsizing of the injection needle 71, that is, of the casing 2.

The guide members 79a to 79f are for regulating the path of the linking members 77 and 78. Specifically, the guide members 79a to 79f are realized by using a pillar member having a smooth surface shape or a pulley, and respectively arranged in the casing 2 so that a direction of being pulled by the contraction of the balloon 4 is changed to a direction of projecting the injection needle 71. By arranging the guide members 79a to 79f in this manner, the linking members 77 and 78 can transmit the contraction force of the balloon 4 (that is, the pressurizing force against the medical fluid) as a driving force for the projection operation of the injection needle 71. The number of guide members is not limited to six, and necessary number of guide members can be arranged in the casing 2.

The medical-fluid discharger realized by including the linking members 77 and 78, the balloon 4, the tube, and the channel forming unit 11 discharges the medical fluid in the storage chamber 3 by reducing the volume of the storage chamber 3, and projects the injection needle 71 from the casing 2 by using the physical force for the discharge of the medical fluid (for example, the discharge pressure of the medical fluid). In other words, the medical-fluid discharger functions as a drive source (drive source for the discharge of the medical fluid) that discharges the medical fluid in the storage chamber 3, and generates a driving force (physical force for the discharge of the medical fluid) for projecting the injection needle 71 from the casing 2.

Figure 15:
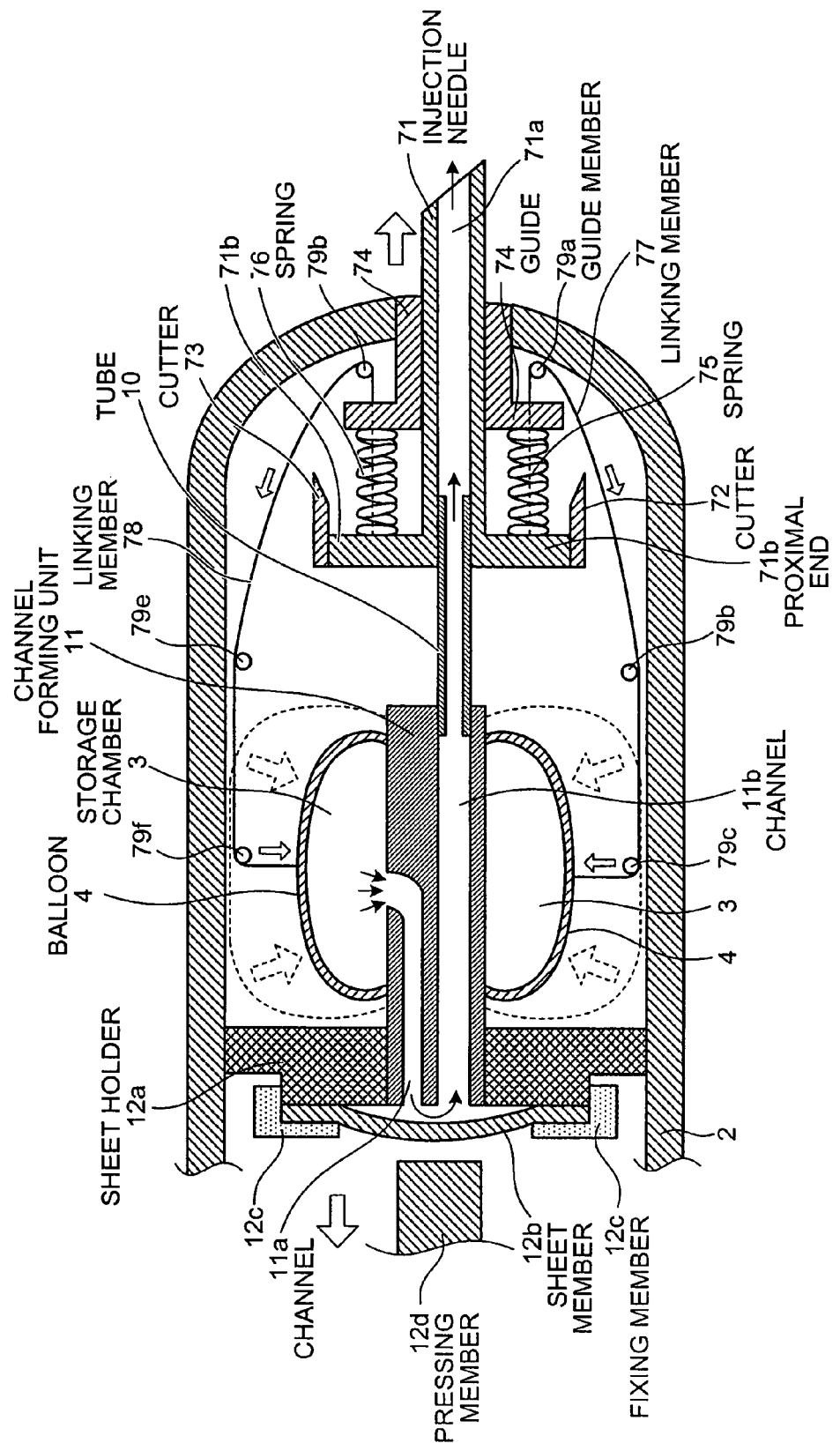
FIG. 15 is a schematic sectional view schematically exemplifying a state where the injection needle is projected by a contraction force of a balloon.

An operation of the body-insertable apparatus 70 is explained next. FIG. 15 is a schematic sectional view schematically exemplifying a state where the injection needle 71 is projected by the contraction force of the balloon 4. The projection operation of the injection needle 71 and the medical-fluid discharge operation are explained with reference to FIG. 15.

The balloon 4 starts contraction based on the operation of the communication adjusting mechanism 12 to execute the medical-fluid discharge operation, as in the first and the second embodiments, and discharges the medical fluid from the distal end of the injection needle 71 via the channels 11a and 11b, the tube 10, and the channel 71a of the injection needle 71. At the same time, the balloon 4 uses the driving force for executing the medical-fluid discharge operation, that is, its contraction force to move the linking members 77 and 78. In this case, the linking members 77 and 78 transmit the contraction force of the balloon 4 to the injection needle 71 as a driving force for the projection operation of the injection needle 71. Therefore, the balloon 4 can move the injection needle 71 in the projecting direction via the linking members 77 and 78, to project the injection needle 71 from the casing 2. The injection needle 71 punctures a desired region in the subject to inject the medical fluid to the desired region.

The contraction force of the balloon 4 is a pressurizing force (one example of the physical force for the discharge of the medical fluid) for pressurizing the medical fluid by reducing the volume of the storage chamber 3, and a driving force for the projection operation of the injection needle 71. That is, the balloon 4 uses its contraction force to perform the medical-fluid discharge operation and the projection operation of the injection needle 71 simultaneously. Therefore, the injection needle 71 can project the injection needle 71 from the casing 2 by using the contraction force of the balloon 4, without consuming new driving power.

A storing operation of the projected injection needle 71 in the casing 2 is explained next. FIG. 16 is a schematic diagram schematically exemplifying a state where the injection needle 71 is stored by cutting the linking members 77 and 78. The storing operation of the injection needle 71 is explained with reference to FIG. 16.

The balloon 4 uses its contraction force, which is the driving force for the medical-fluid discharge operation, to project the injection needle 71. In this case, the injection needle 71 projects from the casing 2 due to the contraction of the balloon 4, and extends the projection length corresponding to the contraction amount of the balloon 4. Accompanying the projection operation of the injection needle 71, the springs 75 and 76 contract, thereby generating an elastic force. The elastic force of the springs 75 and 76 is equal to or less than the contraction force of the balloon 4, when the balloon 4 and the injection needle 71 are in the connected state via the linking members 77 and 78. Therefore, the springs 75 and 76 do not interrupt the projection operation of the injection needle 71 in such a connected state.

Thereafter, when the balloon 4 has finished discharge of a desired amount of medical fluid, the injection needle 71 projects to a position at which the projection length thereof becomes a predetermined length (for example, the maximum length in the projection operation). In such a projected state, the cutters 72 and 73 move together with the injection needle 71, and as shown in FIG. 16, reach a position pressing the linking members 77 and 78, respectively. By pressing the linking members 77 and 78, respectively, the cutters 72 and 73 respectively cut the linking members 77 and 78. As a result, the connected state is released, and the injection needle 71 turns into a free state relative to the contraction force of the balloon 4. In this case, since the contraction force of the balloon 4 equal to or higher than the generated elastic force is not applied to the springs 75 and 76, the springs 75 and 76 extend (return to the natural length) due to the elastic force, thereby returning the projected injection needle 71 into the casing 2. That is, the injection needle 71 is stored inside the casing 2 by using the elastic force of the springs 75 and 76.

The body-insertable apparatus 70 adopting such a configuration can perform the medical-fluid discharge operation and the projection operation of the injection needle 71 by using the contraction force of the balloon, that is, the pressurizing force, without newly consuming the driving power for the projection operation of the injection needle 71. In this case, the body-insertable apparatus 70 can maintain the projected state of the injection needle 71 without depending on a decrease of the discharge pressure of the medical fluid, thereby enabling reliable injection of a desired amount of medical fluid to a desired region in the subject, and suppressing that the medical fluid uselessly remains in the casing 2. Further, the body-insertable apparatus 70 can store the injection needle 71 in the casing 2 by using the elastic force of the springs 75 and 76, without newly consuming the driving power for the storing operation of the injection needle 71.

Accordingly, the body-insertable apparatus 70 can obtain the same operations and effects as those of the body-insertable apparatus 1, can inject the desired amount of medical fluid to the desired region in the subject reliably, and can suppress that the medical fluid uselessly remains in the casing 2.

Fourth Embodiment

A fourth embodiment of the present invention is explained next. In the third embodiment, the projection operation of the injection needle 71 is performed by using the contraction force of the balloon 4. In the fourth embodiment, however, the injection needle is fitted to a piston that pressurizes the medical fluid, and the projection operation of the injection needle 71 is performed by using the pressurizing force of the piston.

Figure 17:
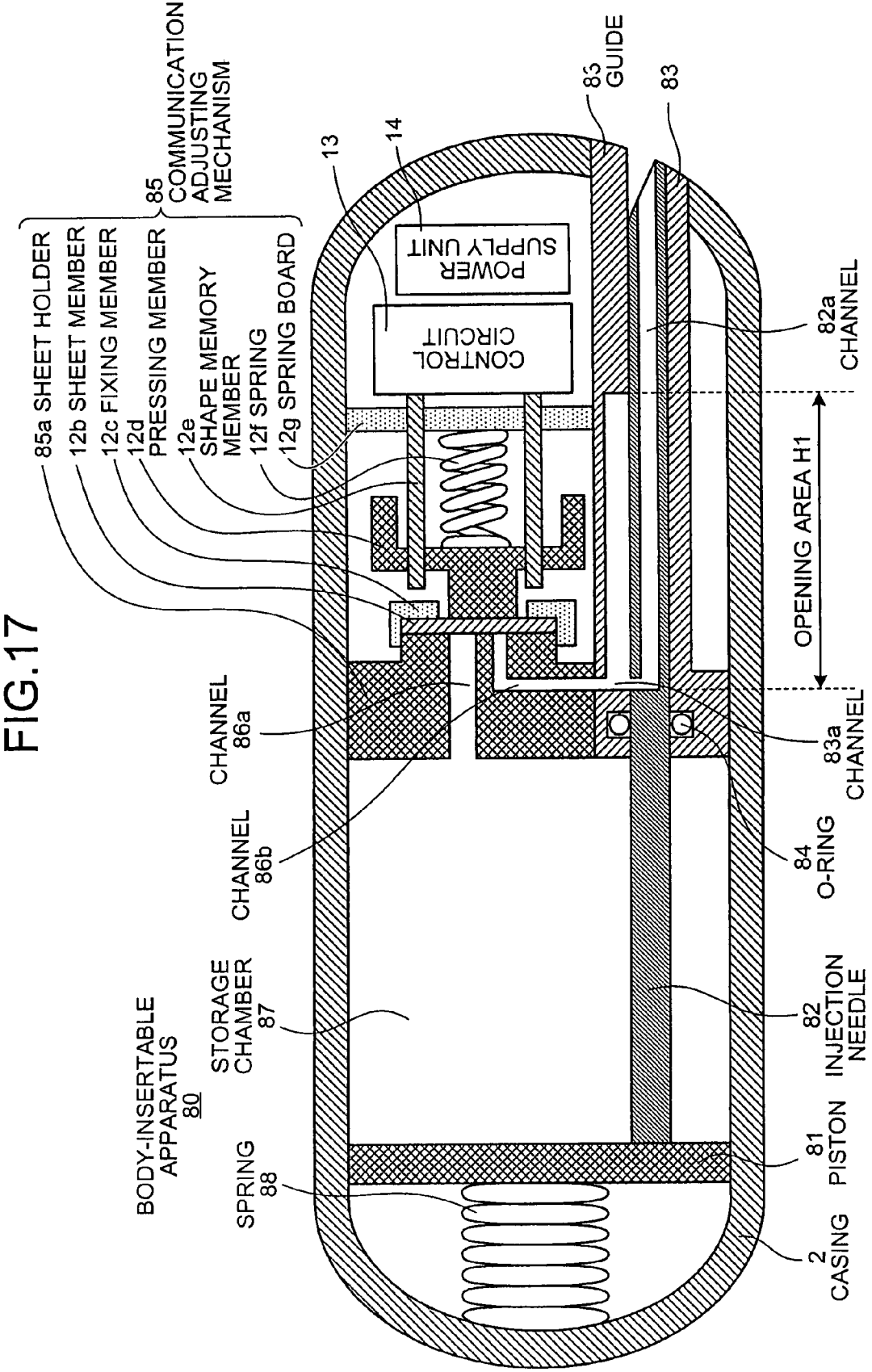
FIG. 17 is a schematic sectional view schematically showing one configuration example of a body-insertable apparatus according to a fourth embodiment of the present invention.

FIG. 17 is a schematic sectional view schematically showing one configuration example of the body-insertable apparatus according to the fourth embodiment of the present invention. A body-insertable apparatus 80 includes a medical-fluid discharge mechanism for projecting the injection needle in conjunction with driving of a piston for performing the medical-fluid discharge operation, instead of the medical-fluid discharge mechanism in the body-insertable apparatus 70 according to the third embodiment (that is, the mechanism for performing the medical-fluid discharge operation and the projection operation of the injection needle 71 in conjunction with each other by using the contraction force of the balloon 4).

That is, as shown in FIG. 17, the body-insertable apparatus 80 has, in the casing 2, a storage chamber 87 for storing the medical fluid beforehand, a piston 81 that pressurizes the medical fluid by reducing the volume of the storage chamber 87, a spring 88 that generates a driving force of the piston 81, an injection needle 82 projecting in conjunction with sliding of the piston 81, and a guide 83 for regulating the sliding direction of the injection needle 82. Further, the body-insertable apparatus 80 includes a communication adjusting mechanism 85 instead of the communication adjusting mechanism 12, and has the control circuit 13 that controls driving of the communication adjusting mechanism 85, and the power supply unit 14 that supplies driving power to the control circuit 13. The control circuit 13 controls driving of the communication adjusting mechanism 85 as in the case of the communication adjusting mechanism 12.

The communication adjusting mechanism 85 has a function of controlling the start or stop of the medical-fluid discharge operation, like the communication adjusting mechanism 12. Specifically, the communication adjusting mechanism 85 has a sheet holder 85a having channels 86a and 86b formed therein, instead of the sheet holder 12a of the communication adjusting mechanism 12. The communication adjusting mechanism 85 has the sheet member 12b arranged on the sheet holder 85a so as to cover the channels 86a and 86b, the fixing member 12c that fixes a rim portion of the sheet member 12b in a state closely adhering to the sheet holder 85a, the pressing member 12d that applies a predetermined pressing force to the sheet member 12b, the spring 12f that generates the pressing force applied by the pressing member 12d, the spring board 12g that holds the spring 12f, and the shape memory member 12e that changes a position of the pressing member 12d relative to the sheet member 12b.

The sheet holder 85a holds the sheet member 12 and connecting the storage chamber 87 to the injection needle 82. Specifically, in the sheet holder 85a, as shown in FIG. 17, a channel 86a communicating with the storage chamber 87 of the medical fluid, and a channel 86b communicating with a channel 82a of the injection needle 82 via a channel 83a of the guide 83 are formed. The sheet holder 85a holds the sheet member 12b so as to cover each opening of the channels 86a and 86b. In this case, when the pressing force is applied by the pressing member 12d, the sheet member 12 cuts off the communicated state between the channels 86a and 86b, and when the pressing force decreases or becomes zero, connects the channels 85a and 86b with each other.

The communication adjusting mechanism 85 can adjust the communicated state between the channels 85a and 86b under control of the control circuit 13, and can start the medical-fluid discharge operation based on sliding of the piston 81 by connecting the channels 85a and 86b with each other, or can stop the medical-fluid discharge operation by cutting off the communicated state between the channels 85a and 86b.

The medical-fluid discharge mechanism in the body-insertable apparatus 80 is constituted by using the piston 81, the guide 83, the sheet holder 85a, the spring 88, and a part of the casing 2. In this case, the storage chamber 87 is formed in a region surrounded by the piston 81, the guide 83, the sheet holder 85a, and the part of the casing 2 (that is, a portion between the piston 81 and the sheet holder 85a, or between the piston 81 and the guide 83). The part of the casing 2 functions as a cylinder along which the piston 81 slides.

The injection needle 82 projects from the casing 2 by using a predetermined drive source for the discharge of the medical fluid, and injects the medical fluid to the desired region in the subject, like the injection needle 5. Specifically, the injection needle 82 has the channel 82a formed therein for connecting the distal end side inserted into the subject to an opening on the side. The injection needle 82 is fitted to the piston 81 at the rear end and arranged so as to slide in the guide 23, in conjunction with sliding of the piston 81.

The guide 83 regulates the sliding direction of the injection needle 82. Specifically, the guide 83 is substantially a cylindrical member having a through hole for inserting the injection needle 82 formed therein, and is arranged corresponding to the sliding position of the injection needle 82. In the guide 83, the channel 83a is formed, which communicates with the channel 86b in the sheet holder 85a. In the channel 83a, an opening area H1 is formed on the inner wall side, and even when the injection needle 82 slides, in conjunction with sliding of the piston 81, the channel 83a maintains the communicated state with the channel 82a. Further, the guide 83 includes an O-ring 84 at the rear end, that is, on the inner wall near the storage chamber 87. The O-ring 84 ensures watertight between the through hole of the guide for inserting the injection needle 82 and the storage chamber 87.

The medical-fluid discharge mechanism in the body-insertable apparatus 80 reduces the volume of the storage chamber 87 to discharge the medical fluid in the storage chamber 87, and projects the injection needle 82 from the casing 2 by using the physical force for the discharge of the medical fluid (for example, the discharge pressure of the medical fluid). In other words, the medical-fluid discharge mechanism functions as a drive source (drive source for the discharge of the medical fluid) that discharges the medical fluid in the storage chamber 87, and generates a driving force (physical force for the discharge of the medical fluid) for projecting the injection needle 82 from the casing 2.

Figure 18:
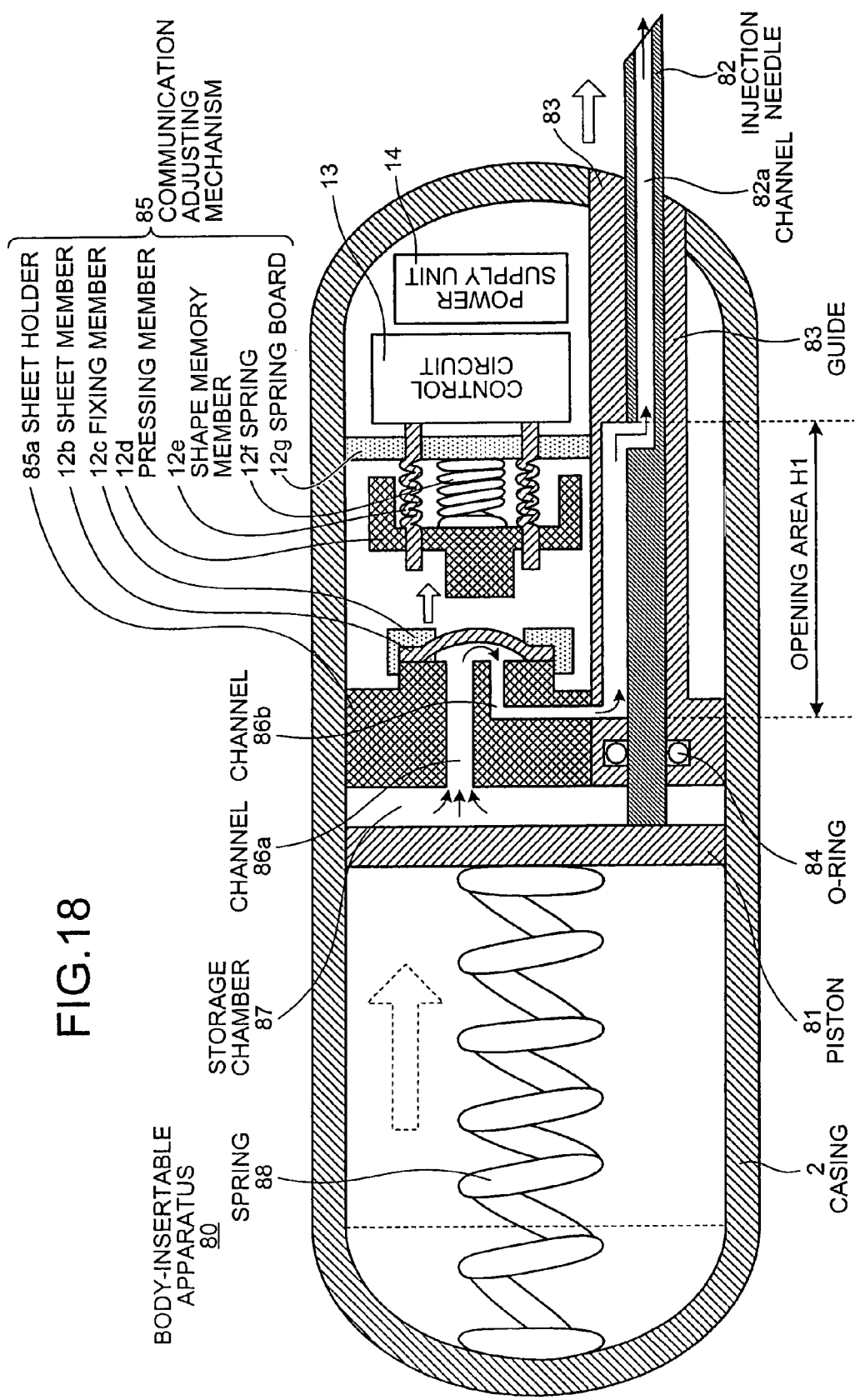
FIG. 18 is a schematic sectional view schematically exemplifying a state where the injection needle is projected by using a pressurizing force of a piston.

An operation of the body-insertable apparatus 80 is explained next. FIG. 18 is a schematic sectional view schematically exemplifying a state where the injection needle 82 is projected from the casing 2 by using the pressurizing force of the piston 81. The projection operation of the injection needle 82 and the medical-fluid discharge operation are explained with reference to FIG. 18.

When the communication adjusting mechanism 85 makes the channels 86a and 86b communicate with each other under the control of the control circuit 13, the piston 81 uses the driving force generated by the spring 88 to slide in a direction of reducing the volume of the storage chamber 87 to pressurize the medical fluid. The thus pressurized medical fluid is discharged from the distal end of the injection needle 82 via the channels 86a and 86b, the channel 83a in the guide 83, and the channel 82a in the injection needle 82. At the same time, the piston 81 uses the pressurizing force by the spring 88 to push out the injection needle 82. Due to the sliding operation of the piston 81, the injection needle 82 slides along the guide 83 and projects from the casing 2, to inject the medical fluid, for example, to a desired region in the subject.

The driving force generated by the spring 88 is a pressurizing force (one example of the physical force for the discharge of the medical fluid) for the piston 81 to reduce the volume of the storage chamber 87 and pressurize the medical fluid, and a driving force for the medical-fluid discharge operation. As described above, the piston 81 uses this pressurizing force to perform the medical-fluid discharge operation and the projection operation of the injection needle 82 simultaneously. Accordingly, the injection needle 82 can project from the casing 2 by using the pressurizing force, without newly consuming the driving power.

The body-insertable apparatus 80 adopting such configuration can use the pressurizing force of the piston 81 to perform the medical-fluid discharge operation and the projection operation of the injection needle 82 simultaneously, without newly consuming the driving power for the projection operation of the injection needle 82, and hence can perform the projection operation of the injection needle at the time of injecting the medical fluid to the desired region in the subject in a power saving manner.

The body-insertable apparatus 80 projects the injection needle 82, by attaching the injection needle 82 to the piston 81 so as to associate sliding of the injection needle 81 with sliding of the piston 81. Therefore, a new drive mechanism for executing the projection operation of the injection needle need not be provided, thereby simplifying the drive mechanism and realizing downsizing of the body-insertable apparatus.

In the body-insertable apparatus 80, since the communication adjusting mechanism 85 can adjust the communicated state and the cutoff state between the channels 86a and 86b based on the control of the control circuit 13, start and stop of the medical-fluid discharge operation can be intermittently repeated.

Further, the body-insertable apparatus 80 can maintain the projected state of the injection needle 82 without depending on a decrease of the discharge pressure of the medical fluid, can inject the desired amount of medical fluid to the desired region in the subject reliably, and can suppress that the medical fluid uselessly remains in the casing 2.

Modification of Fourth Embodiment

A modification of the body-insertable apparatus 80 in the fourth embodiment of the present invention is explained next.

In the fourth embodiment, start and stop of the medical-fluid discharge operation is controlled by the operation of the communication adjusting mechanism 85. In the modification of the fourth embodiment, however, a piston drive mechanism driven and controlled by the control circuit is provided, and the piston and the injection needle are simultaneously slid due to the operation of the piston drive mechanism.

Figure 19:
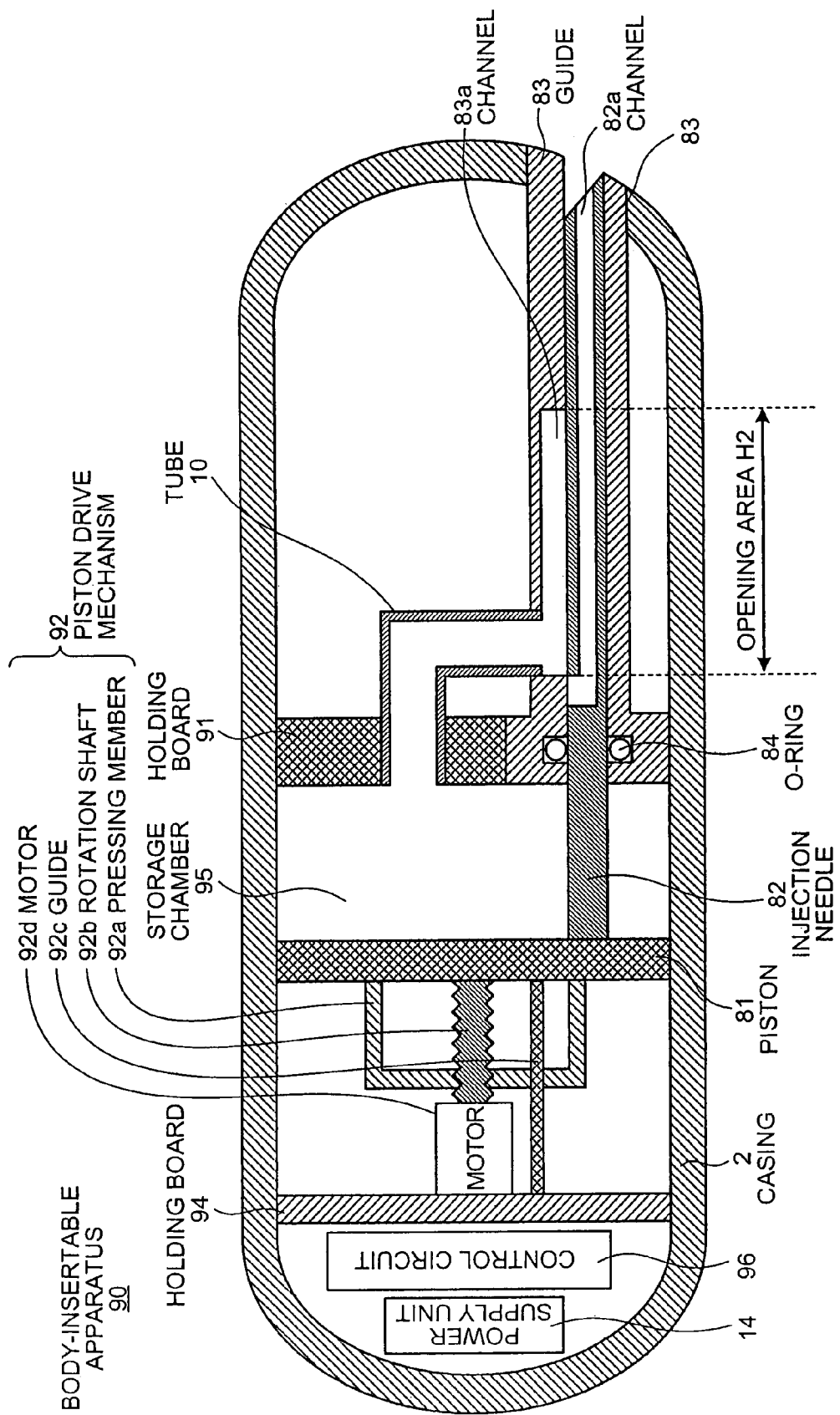
FIG. 19 is a schematic sectional view schematically showing one configuration example of the body-insertable apparatus, which is a modification of the fourth embodiment according to the present invention.

FIG. 19 is a schematic sectional view schematically showing one configuration example of the body-insertable apparatus, which is a modification of the fourth embodiment according to the present invention. As shown in FIG. 19, a body-insertable apparatus 90 includes the tube 10 and a holding board 91 instead of the communication adjusting mechanism 85 of the body-insertable apparatus 80 according to the fourth embodiment, and a piston drive mechanism 92 is provided instead of the spring 88. The body-insertable apparatus 90 also includes a control circuit 96 for controlling the piston drive mechanism 92 instead of the control circuit 13, and the power supply unit 14 that supplies driving power to the control circuit 96 is arranged. Other configurations are the same as those of the fourth embodiment, and like reference letters or numerals refer to like constituent elements.

The piston mechanism in the body-insertable apparatus 90 is constituted by using the piston 81 that slides so as to reduce the volume of the storage chamber 95, the guide 83 for regulating the sliding direction of the injection needle 82, a holding board 91 for holding the tube 10, a piston drive mechanism 92, and a part of the casing 2. In this case, the storage chamber 95 is formed in a region surrounded by the piston 81, the guide 83, the holding board 91, and the part of the casing 2 (that is, a portion between the piston 81 and the holding board 91, or between the piston 81 and the guide 83). The part of the casing 2 functions as a cylinder along which the piston 81 slides.

The holding board 91 forms an outer circumference of the storage chamber 95, and holds the tube 10. In this case, the tube 10 is inserted into the holding board 91 at one end, and into an opening of the guide 83 at the other end, so as to connect the storage chamber 95 to the channel 83a in the guide 83. In the body-insertable apparatus 90, the channel 83a in the guide 83 has an opening area H2 formed therein, as shown in FIG. 19, on the inner wall side, so that the channel 83a does not communicate with the channel 82a in the state with the injection needle 82 being stored in the casing 2, but maintains the communicated state with the channel 82a during a period since the injection needle 82 has started to project from the casing 2 until finishes projection.

The piston drive mechanism 92 generates a driving force (that is, the pressurizing force) for the piston 81 under the control of the control circuit 96, and slides the piston 81 in a direction of reducing the volume of the storage chamber 95. Specifically, the piston drive mechanism 92 has a pressing member 92a for pressing the piston 81, a rotation shaft 92b for converting rotation drive to linear drive of the pressing member 92a, a guide 92c for regulating the moving direction of the pressing member 92a, and a motor 92d that executes rotation drive of the shaft 92b. The guide 92c and the motor 92d are provided on the holding board 94.

The pressing member 92a applies the pressing force to the piston 81, to slide the piston 81 in a direction of reducing the volume of the storage chamber 95. Specifically, the pressing member 92a is a member having, for example, an inverse C shape, and as shown in FIG. 19, is screwed together with an external screw on the outer circumference of the rotation shaft 92b, and penetrated by the guide 92c. The pressing member 92a is linearly driven based on the rotation drive of the rotation shaft 92b, and presses its end against the piston 81. The pressing member 92a can make the piston 81 slide by pressing its end against the piston 81.

The motor 92d is provided on the holding board 94, and executes rotation drive of the rotation shaft 92b under the control of the control circuit 96. In other words, the motor 92d and the rotation shaft 92b function as a linear actuator for pressing the pressing member 92a against the piston 81.

The control circuit 96 controls the drive of the motor 92d. Specifically, the control circuit 96 controls the drive of the motor 92d, to start or stop linear drive of the pressing member 92a by the drive control of the motor 92d. In this case, the control circuit 96 can start or stop sliding of the piston 81 by controlling linear drive of the pressing member 92a, and can control the medical-fluid discharge operation based on pressurization of the medical fluid by reducing the volume of the storage chamber 95. As the configuration for specifying the execution timing of the drive control of the motor 92d by the control circuit 96, for example, a timer mechanism can be provided, or a radio reception mechanism can be incorporated and a control signal can be supplied from outside.

The medical-fluid discharger realized by including the piston mechanism and the piston drive mechanism 92 of the body-insertable apparatus 90 discharges the medical fluid in the storage chamber 95 by reducing the volume of the storage chamber 95, and projects the injection needle 82 from the casing 2 by using the physical force for the discharge of the medical fluid (for example, pressurizing force applied to the medical fluid). In other words, the medical-fluid discharger functions as a drive source (drive source for the discharge of the medical fluid) that discharges the medical fluid in the storage chamber 95, and generates a driving force (physical force for the discharge of the medical fluid) for projecting the injection needle 82 from the casing 2.

Figure 20:
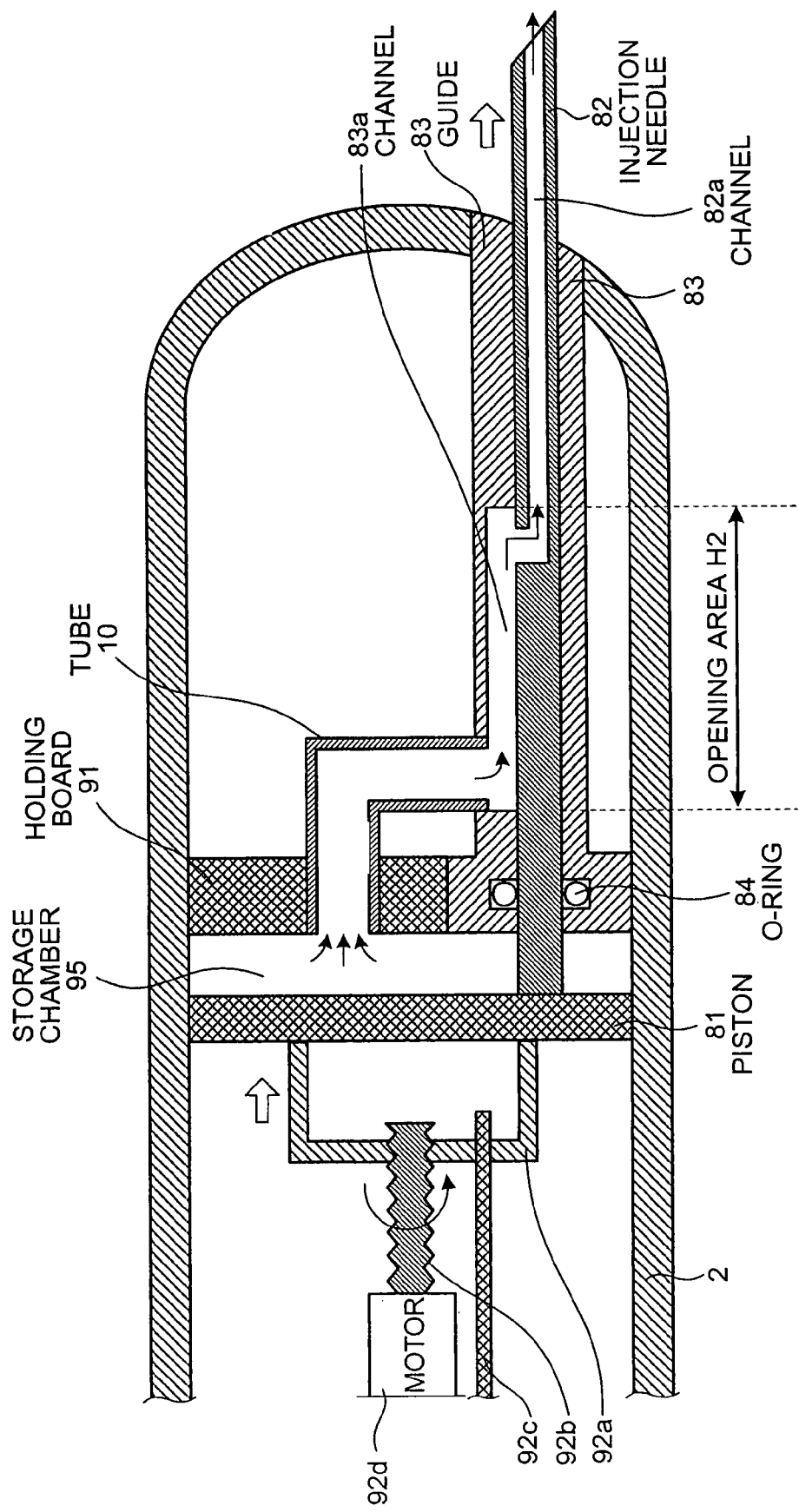
FIG. 20 is a schematic sectional view schematically exemplifying a state where the injection needle is projected by an operation of a piston drive mechanism.

An operation of the body-insertable apparatus 90 is explained. FIG. 20 is a schematic sectional view schematically exemplifying a state where the injection needle 82 is projected by an operation of a piston drive mechanism 92. The projection operation of the injection needle 82 and the medical-fluid discharge operation are explained with reference to FIG. 20.

The control circuit 96 starts rotation drive of the rotation shaft 92b by performing drive control of the motor 92b. The rotation shaft 92b converts rotation drive thereof to linear drive of the pressing member 92a. The pressing member 92a presses the piston 81 based on the rotation drive of the rotation shaft 92b, to thrust the piston 81 forward with the moving direction thereof being regulated by the guide 92c. In this case, the rotation shaft 92b and the motor 92d generates the pressing force for sliding the piston 81, and applies the generated pressing force to the piston 81 via the pressing member 92a.

The piston 81 slides in a direction of reducing the volume of the storage chamber 95 to pressurize the medical fluid according to the operation of the piston drive mechanism 92. Sliding of the piston 81 is performed by using the pressing force generated by the piston drive mechanism 92. The thus pressurized medical fluid is discharged from the distal end of the injection needle 82 via the tube 10, the channel 83a of the guide 83, and the channel 82a of the injection needle 82. At the same time, the piston 81 uses the pressing force by the piston drive mechanism 92 to push out the injection needle 82. According to the sliding operation of the piston 81, the injection needle 82 slides along the guide 83 and projects from the casing 2, to inject the medical fluid, for example, to a desired region in the subject.

The pressing force applied via the pressing member 92a is a pressurizing force (one example of the physical force for the discharge of the medical fluid) for the piston 81 to reduce the volume of the storage chamber 95 and pressurize the medical fluid, and a driving force for the medical-fluid discharge operation. As in the fourth embodiment, the piston 81 uses this pressurizing force to perform the medical-fluid discharge operation and the projection operation of the injection needle 82 simultaneously. Accordingly, the injection needle 82 can project from the casing 2 by using the pressurizing force, without newly consuming the driving power.

The body-insertable apparatus 90 adopting such a configuration can execute the medical-fluid discharge operation and the projection operation of the injection needle 82 together by using the pressing force applied to the piston 81, that is, the pressurizing force of the piston 81, so long as it consumes the driving power for sliding the piston 81. Further, the body-insertable apparatus 90 integrates the piston 81 and the injection needle 82 to associate sliding of the piston 81 with the projection operation of the injection needle 82, as in the body-insertable apparatus 80 according to the fourth embodiment. Therefore, the body-insertable apparatus 90 can obtain the operations and effects similar to those of the fourth embodiment.

In the body-insertable apparatus 90, since the piston drive mechanism 92 can start or stop sliding of the piston 81 based on the control of the control circuit 96, start and stop of the medical-fluid discharge operation can be intermittently repeated. Further, a storage function of the injection needle 82 can be added to the body-insertable apparatus 90 by shifting the pressing member 92a to an opposite direction by the piston drive mechanism 92 based on the control of the control circuit 96, so that the piston 81 is returned to the original position together with the pressing member 92a.

Since the body-insertable apparatus 90 can maintain the projecting state of the injection needle 82 without depending on a decrease of the discharge pressure of the medical fluid, a desired amount of medical fluid can be reliably injected to a desired region in the subject, and it can be suppressed that the medical fluid uselessly remains in the casing 2.

Fifth Embodiment

A fifth embodiment of the present invention is explained next. The body-insertable apparatus according to the fifth embodiment includes a storage bag for storing the medical fluid, and a pressurizing force for compressing the storage bag is used to perform the medical-fluid discharge operation and the projection operation of the injection needle simultaneously.

Figure 21:
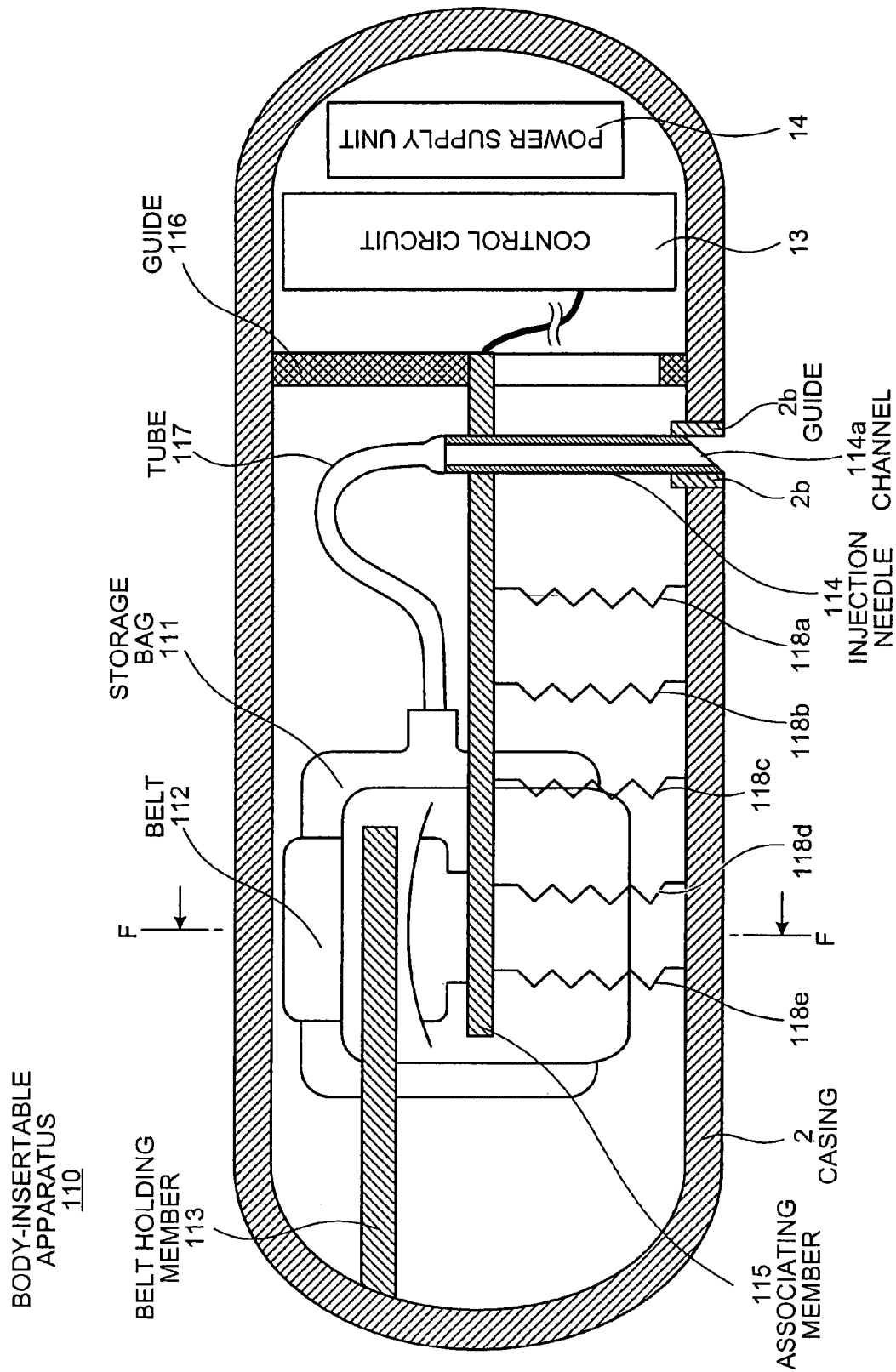
FIG. 21 is a schematic sectional view schematically showing one configuration example of a body-insertable apparatus according to a fifth embodiment of the present invention.
Figure 22:
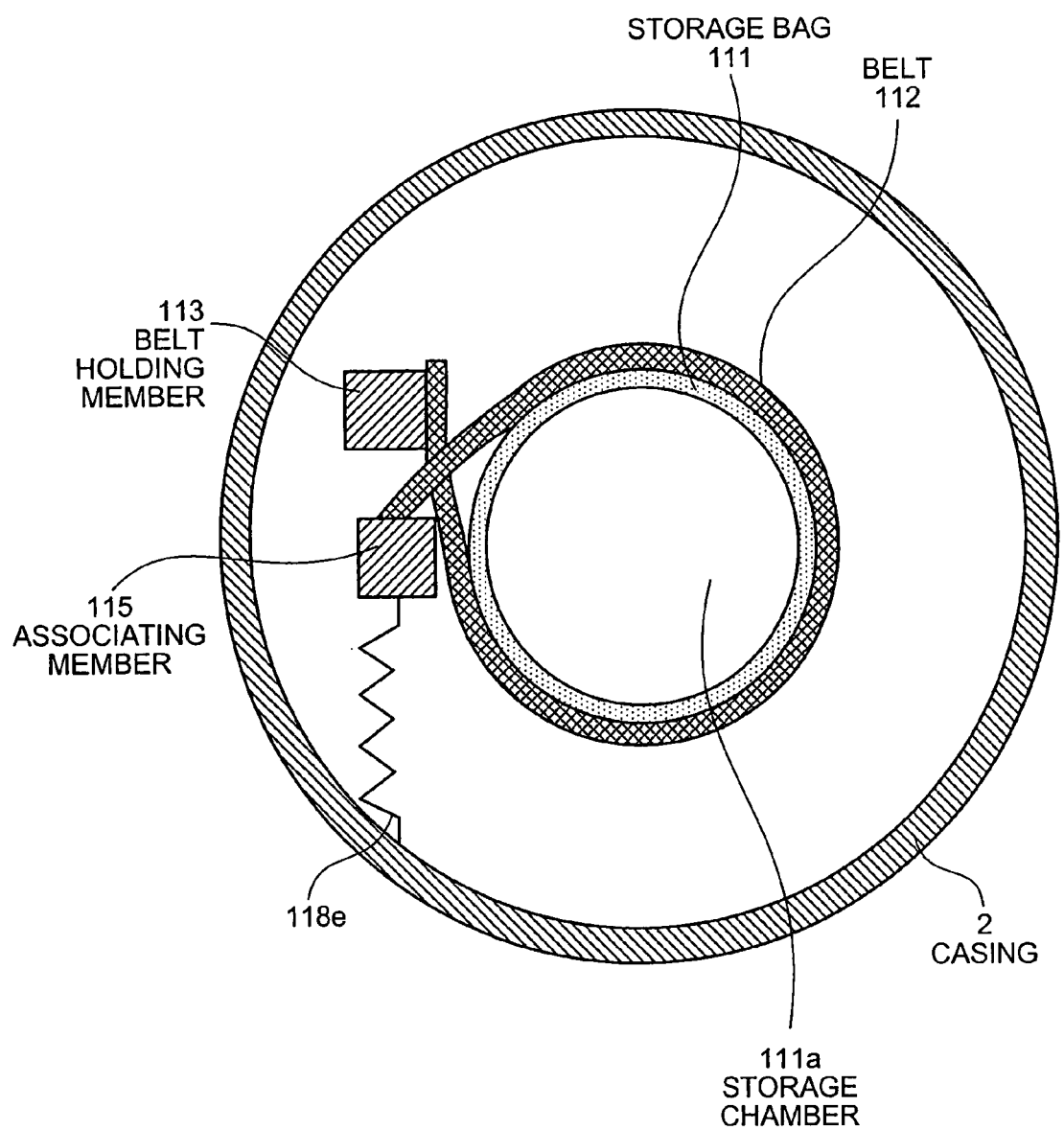
FIG. 22 is a schematic sectional view along line F-F of the body-insertable apparatus shown in FIG. 21.

FIG. 21 is a schematic sectional view schematically showing one configuration example of the body-insertable apparatus according to the fifth embodiment of the present invention. FIG. 22 is a schematic sectional view along line F-F of the body-insertable apparatus shown in FIG. 21. As shown in FIGS. 21 and 22, this body-insertable apparatus 110 has a storage bag 111 for storing the medical fluid beforehand inside the casing 2. The body-insertable apparatus 110 has a function of performing both the medical-fluid discharge operation and the projection operation of the injection needle simultaneously by using the pressurizing force for compressing the storage bag 111. Therefore, the body-insertable apparatus 110 includes, in the casing 2, a belt 112 for fastening and compressing the storage bag 111, a belt holding member 113 for holding one end of the belt 112, an injection needle 114, and an associating member 115 that associates the compression operation of the storage bag 111 and the projection operation of the injection needle 114. The body-insertable apparatus 110 also includes, in the casing 2, a guide 116 that regulates a moving direction of the associating member 115, a tube 117 that connects the storage bag 111 to the injection needle 114, and shape memory members 118a to 118e that generate a driving force (that is, the pressurizing force) for the compression operation. The body-insertable apparatus 110 further has the control circuit 13 that controls a shape change of the shape memory members 118a to 118e, and a power supply unit 14 that supplies the driving power to the control circuit control circuit 13, in the casing 2.

The storage bag 111 is a baglike member that forms a storage chamber 111a for storing the medical fluid beforehand therein, and is a soft member capable of easily reducing the volume of the storage chamber 111a by using a belt or the like to fasten the storage bag 111. The storage bag 111 has an outlet for allowing the medical fluid in the storage chamber 111a to flow outside, and the tube 117 is connected to the outlet.

The belt 112 discharges the medical fluid by compressing the storage bag 111. Specifically, the belt 112 is wound around the storage bag 111 in a state with opposite ends thereof crossing each other. In this case, one end of the belt 112 is a fixed end, and the other end is a free end capable of sliding. The belt 112 is fitted to the belt holding member 113 at the fixed end and to the associating member 115 at the free end, and by pulling the free end, the storage bag 111 can be fastened. The belt 112 reduces the volume of the storage chamber 111a by fastening the storage bag 111 to pressurize the medical fluid, and discharge the medical fluid.

The belt holding member 113 holds the belt 112. Specifically, the belt holding member 113 is fixed to the casing 2, and holds the belt 112 by holding the one end of the belt 112, and holds the storage bag 111 via the belt 112. In this case, the one end held by the belt holding member 113 is the fixed end.

The injection needle 114 projects from the casing 2 by using the driving source relating to the discharge of the medical fluid, and injects the medical fluid to a desired region in the subject, like the injection needle 5. Specifically, the injection needle 114 has a channel 114a formed therein, which connects the distal end side for puncturing the subject and the rear end, and the rear end is held by the associating member 115. The injection needle 114 slides accompanying the drive of the associating member 115. More specifically, the injection needle 114 projects from the casing 2 accompanying the drive of the associating member 115, or returns into the casing 2. The injection needle 114 is connected to the tube 117 at the rear end, and when the medical fluid is allowed to flow in via the tube 117, discharges the medical fluid from the distal end side. A cylindrical guide 2a is formed at an entrance of the injection needle 114 in the casing 2. The guide 2a regulates the sliding direction of the injection needle 114.

The associating member 115 associates the compression operation of the storage bag 111 by the belt 112 with the projection operation of the injection needle 114. Specifically, the free end of the belt 112 and the injection needle 114 are fitted to the associating member 115, and one end of the associating member 115 is slidably inserted into a through hole in the guide 116. The associating member 115 moves in a direction of fastening the belt 112 (that is, in a direction of compressing the storage bag 111), to project the injection needle 114 from the casing 2. The associating member 115 moves in a direction of loosening the belt 112 to store the injection needle 114 in the casing 2.

The guide 116 regulates the moving direction of the associating member 115. Specifically, the guide 116 is a plate-like member having a longitudinal through hole formed therein, and by inserting one end of the associating member 115 slidably into the through hole, the moving direction of the associating member 115 is regulated. In this case, the associating member 115 moves along the through hole in the guide 116, thereby reliably performing the projection operation and storage operation of the injection needle 114.

The tube 112 circulates the medical fluid in the storage bag 111 to the channel 114a in the injection needle 114. Specifically, the tube 117 is a soft tube member having flexibility or resilience, and one end thereof is connected to the storage bag 111 and the other end is connected to the injection needle 114. The tube 117 moves, matched with the projection operation or storage operation of the injection needle 114, to maintain the communicated state between the storage chamber 111a in the storage bag 111 and the channel 114a in the injection needle 114, and circulate the medical fluid discharged from the storage bag 111 to the channel 114a in the injection needle 114.

The shape memory members 118a to 118e generates a driving force for performing the compression operation of the storage bag 111 and the projection operation of the injection needle 114 synchronously. Specifically, the shape memory members 118a to 118e have a cylindrical or coiled (for example, SMA coil) structure, and are formed of a shape memory alloy having a predetermined shape memory characteristic and a predetermined electrical resistivity. The shape memory members 118a to 118e are fixed to the casing 2 at one end, and to the associating member 115 at the other end, and have a sufficient length so that the associating member 115 can store the injection needle 114 and loosen the belt 112 (stop the compression operation of the storage bag 111) under a temperature condition, for example, same as the temperature in the subject. On the other hand, the shape memory members 118a to 118e change the shapes at a predetermined temperature, for example, under a temperature condition sufficiently higher than the temperature in the subject, so that the associating member 115 projects the injection needle 114 and fastening the belt 112 (starts the compression operation of the storage bag 111). The shame memory members need only to be arranged in a number necessary for generating the driving force capable of performing the compression operation of the storage bag 111 and the projection operation of the injection needle 114 synchronously, and the number thereof is not particularly limited to five.

The shape memory members 118a to 118e are electrically connected to the control circuit 13 via a wiring (not shown) or the like provided in the associating member 115. The control circuit 13 controls the shape change of the shape memory members 118a to 118e, as in the shame memory member 12e. The control circuit 13 functions so as to supply the electric current to the shape memory members 118a to 118e, when the body-insertable apparatus 110 introduced into the subject reaches a desired region in the subject, for example, to the affected part, thereby changing the shape of the shape memory members 118a to 118e (to compress the shape). The shape memory members 118a to 118e generate the driving force according to the control of the control circuit 13, and the associating member 115 uses the driving force to perform the compression operation of the storage bag 111 and the projection operation of the injection needle 114 synchronously. On the other hand, the control circuit 13 returns the shape memory members 118a to 118e to the original shape by stopping the current supply. In this case, the associating member 115 uses the driving force generated by the shape memory members 118a to 118e resuming the original shape, to loosen the belt 112 (that is, stop the compression operation of the storage bag 111) and store the injection needle 114.

The medical-fluid discharger realized by including the storage bag 111, the belt 112, the belt holding member 113, the associating member 115, the shape memory members 118a to 118e, and the tube 117 discharges the medical fluid in the storage chamber 111a by reducing the volume of the storage chamber 111a, and projects the injection needle 114 from the casing 2 by using the physical force for the discharge of the medical fluid (for example, pressurizing force applied to the medical fluid). In other words, the medical-fluid discharger functions as a drive source (drive source for the discharge of the medical fluid) that discharges the medical fluid in the storage chamber 111a, and generates a driving force (physical force for the discharge of the medical fluid) for projecting the injection needle 114 from the casing 2.

Figure 23:
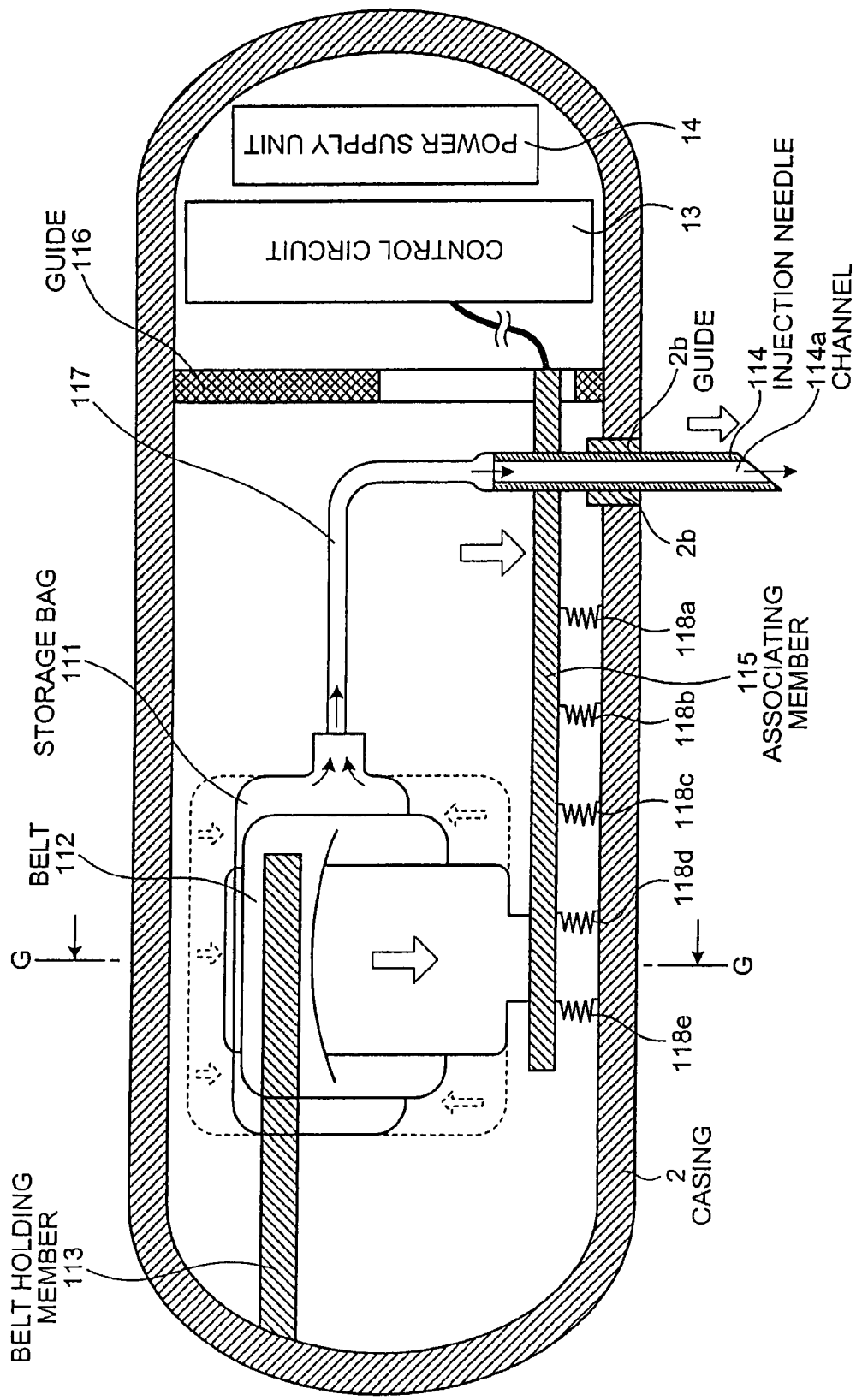
FIG. 23 is a schematic sectional view schematically exemplifying a state where the injection needle is projected, in conjunction with compression operation of a storing bag.
Figure 24:
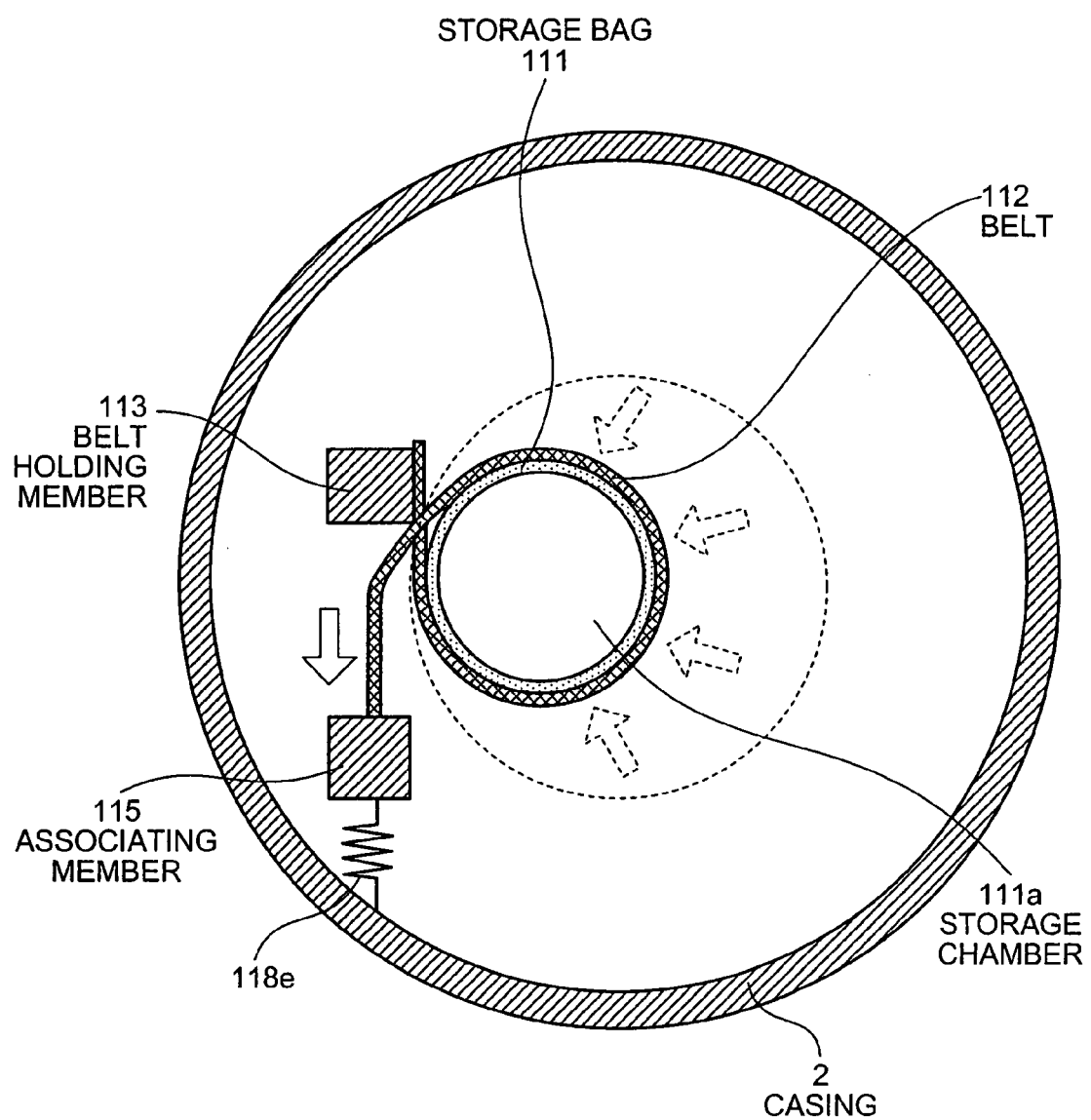
FIG. 24 is a schematic sectional view along line G-G of the body-insertable apparatus shown in FIG. 23.

An operation of the body-insertable apparatus 110 is explained. FIG. 23 is a schematic sectional view schematically exemplifying a state where the injection needle 114 is projected from the casing 2, in conjunction with the compression operation of the storage bag 111. FIG. 24 is a schematic sectional view along line G-G of the body-insertable apparatus shown in FIG. 23. The projection operation of the injection needle 115 and the medical-fluid discharge operation are explained with reference to FIGS. 23 and 24.

The control circuit 13 controls the shape change of the shape memory members 118a to 118e, to change (specifically, to contract) the shape of the shape memory members 118a to 118e. The shape memory members 118a to 118e generate a driving force with the change of the shape, to move the associating member 115 in a direction of fastening the belt 112. In this case, the associating member 115 pulls the free end of the belt 112 by using the driving force. Due to the operation of the associating member 115, the belt 112 fastens the storage bag 111 to compress it and reduces the volume of the storage chamber 111a to pressurize the medical fluid. The medical fluid in the thus pressurized storage bag 111 is discharged from the distal end of the injection needle 114 via the tube 117 and the channel 114a.

The associating member 115 uses the driving force based on the shape change of the shape memory members 118a to 118e to project the injection needle 114 from the casing 2, synchronously with the compression operation of the storage bag 111. The thus projected injection needle 114 punctures a desired region in the subject, to inject the medical fluid to the desired region.

On the other hand, when the shape memory members 118a to 118e substantially resume the original shape based on the control of the control circuit 13, the associating member 115 moves in a direction of loosening the belt 112 due to the shape-resuming operation of the shape memory members 118a to 118e to release the compression of the storage bag 111, and stores the injection needle 114 in the casing 2. In this case, since the compression operation of the storage bag 111 by the belt 112 is suspended, the medical fluid in the storage bag 111 is not discharged. When the belt resumes the compression operation of the storage bag 111 due to the operation of the associating member 115, discharge of the medical fluid is resumed.

The driving force generated by the shape change of the shape memory members 118a to 118e is a pressurizing force (one example of the physical force for the discharge of the medical fluid) for the belt 112 to compress the storage bag 111, that is, reduce the volume of the storage chamber 111a and pressurize the medical fluid. The associating member 115 uses this pressurizing force to perform the compression operation of the storage bag 111 and the projection operation of the injection needle 114 synchronously. Accordingly, the injection needle 114 can project from the casing 2 by using the pressurizing force, without newly consuming the driving power.

The belt 112, the associating member 115, and the shape memory members 118a to 118e function as the medical fluid pressurizing unit that compresses the storage bag 111 by using the pressuring force, to pressurize the medical fluid, and also functions as the medical-fluid discharger by adding the storage bag 111 and the tube 117. The medical-fluid discharger performs a discharge operation of the medical fluid based on the compression operation of the storage bag 111.

The body-insertable apparatus 110 adopting such a configuration can execute the medical-fluid discharge operation (that is, compression operation of the medical fluid bag 111) and the projection operation of the injection needle 114 synchronously by using the generated pressurizing force, so long as the body-insertable apparatus 110 consumes the driving power for generating the pressuring force for compressing the storage bag 111. Further, the body-insertable apparatus 110 can suspend the medical-fluid discharge operation and perform the storage operation of the injection needle 114, due to the shape-resuming operation of the shape memory members 118a to 118e. Therefore, the body-insertable apparatus 110 can obtain the same operations and effects as those in the first embodiment.

Further, by moving the associating member 115 attached with the free end of the belt 112 and the injection needle 114, the compression operation of the medical fluid bag 111 is associated with the projection operation of the injection needle 114. Therefore, the drive mechanism for discharging the medical fluid and the projecting the injection needle can be simplified, thereby promoting downsizing of the apparatus.

Furthermore, since the projection operation of the injection needle 114 is performed by the shape change of the shape memory members 118a to 118e, the projected state of the injection needle 114 can be maintained until a desired amount of medical fluid is injected to the desired region in the subject, without depending on a decrease of the discharge pressure of the medical fluid. Accordingly, the medical fluid can be reliably injected to the desired region in the subject, and it can be suppressed that the medical fluid uselessly remains in the casing 2.

Sixth Embodiment

A sixth embodiment of the present invention is explained. In the body-insertable apparatus according to the sixth embodiment, the injection needle is projected from the casing by using a predetermined drive source, and the medical-fluid discharge operation is started.

Figure 25:
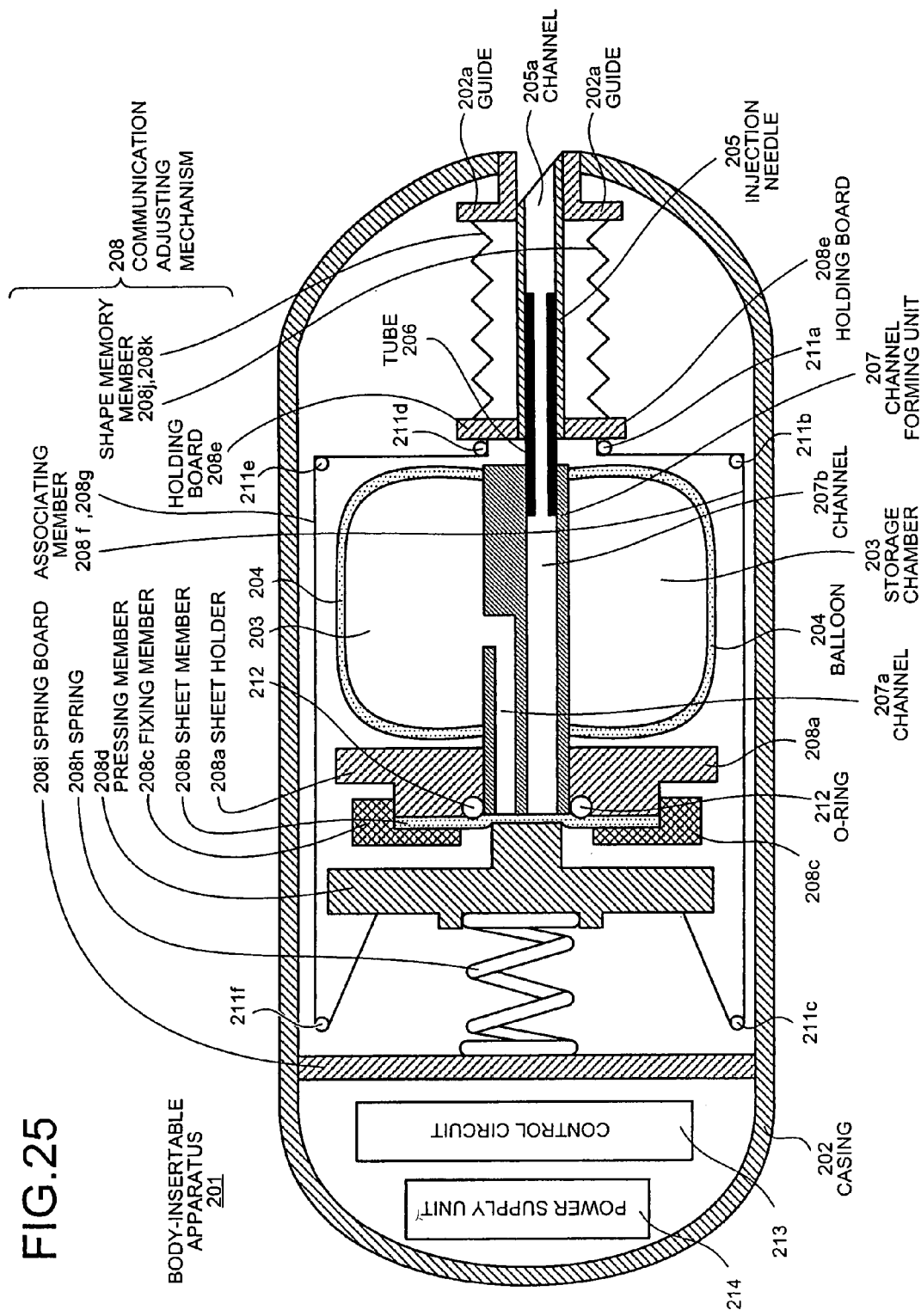
FIG. 25 is a schematic sectional view schematically showing one configuration example of a body-insertable apparatus according to a sixth embodiment of the present invention.

FIG. 25 is a schematic sectional view schematically showing one configuration example of the body-insertable apparatus according to the sixth embodiment of the present invention. This body-insertable apparatus 201 is introduced into the subject, to inject the medical fluid pre-stored in the storage chamber to a desired region in the subject. As shown in FIG. 25, the body-insertable apparatus 201 includes a capsule-like casing 202 having a size easily swallowable by the subject such as a patient. The body-insertable apparatus 201 includes, in the casing 202, a balloon 204 that forms a storage chamber 203 for storing the medical fluid beforehand, an injection needle 205 for injecting the medical fluid to the desired region in the subject, and a tube 206 and a channel forming unit 207 for forming a first channel connecting to the storage chamber 203 and a second channel connecting to the injection needle 205. The body-insertable apparatus 201 further includes, in the casing 202, a communication adjusting mechanism 208 for adjusting the communicated state between the first channel and the second channel and projecting the injection needle, a control circuit 213 that controls a driving state of the communication adjusting mechanism 208, and a power supply unit 214 that supplies driving power to the control circuit 213.

The storage chamber 203 pre-stores the medical fluid to be injected to the desired region in the subject. Specifically, in the sixth embodiment, the storage chamber 203 is formed in an area covered with an inner surface of the balloon 204 and a surface of the channel forming unit 207, and the medical fluid is stored in this area.

The balloon 204 forms the most part of an external wall of the storage chamber 203, and is realized by using an elastic member such as rubber. The balloon 204 expands due to injection of the medical fluid in a predetermined amount and stores the medical fluid, while maintaining the expanding state, that is, a state where the storage chamber 203 is expanded. When the storage chamber 203 and the injection needle 205 communicate with each other due to an operation of the communication adjusting mechanism 208, the balloon 204 reduces (compresses) the volume of the storage chamber 2 by using a contraction force thereof to pressurize the medical fluid, and discharges the medical fluid via the injection needle 205. That is, the balloon 204 functions as the medical-fluid discharger that uses the contraction force thereof to compress the storage chamber 203 and pressurize the medical fluid, and performs the medical-fluid discharge operation for discharging the medical fluid.

The injection needle 205 projects from the casing 202 by using the drive source for the discharge of the medical fluid to inject the medical fluid stored in the storage chamber 203 to the desired region in the subject. Specifically, the injection needle 205 has a channel 205a formed therein for connecting a distal end side (a side forming a sharp point) for puncturing the subject and a proximal end side, and is provided near a guide 202a provided in an opening in the casing 202 so as to be freely put in and out. In this case, in the injection needle 205, a tube 206 is slidably inserted in the channel 205a. The injection needle 205 slides due to the operation of the communication adjusting mechanism 208 and projects from the casing 202 along the guide 202a. The guide 202a regulates the moving direction of the injection needle 205 so that the injection needle 205 can be smoothly projected or stored.

The tube 206 and the channel forming unit 207 are for forming the first channel and the second channel. Specifically, channels 207a and 207b are formed inside of the channel forming unit 207, and the tube 206 is connected to the channel 207b. In this case, the channel 207a communicates with the storage chamber 203, and the channel 207b communicates with the channel 205a of the injection needle 205 via the tube 206. That is, the channel 207a forms the first channel, and the channel 207b and the tube 206 form the second channel. The channels 207a and 207b, and the tube 206 function as a medical fluid channel for circulating the medical fluid in the storage chamber 203 to the channel 205a in the injection needle 205, when the channels 207a and 207b, and the tube 206 communicate with each other.

It is desired that the channels 207a and 207b are formed parallel with each other along the longitudinal direction of the casing 202. The size of the channel forming unit 207 can be downsized as much as possible by forming the channels 207a and 207b in this manner, thereby promoting downsizing of the body-insertable apparatus 201.

The communication adjusting mechanism 208 adjusts the communicated state (communication state) between the first channel and the second channel, that is, the channels 207a and 207b under control of the control circuit 213, and functions so as to project the injection needle 205. In this case, the communication adjusting mechanism 208 functions as a discharge starting unit that starts the contraction operation of the balloon 204, that is, a discharge operation of the medical fluid by performing the communication adjusting operation for communicating the channels 207a and 207b with each other. The communication adjusting mechanism 208 has a function for cutting off the communicated state (cutoff state) between the channels 207a and 207b by using the elastic force by a spring, and for storing the injection needle 205 in the casing 202. In this case, the communication adjusting mechanism 208 stops the contraction operation of the balloon 204, that is, the medical-fluid discharge operation by performing a cutoff adjusting operation for cutting off the communicated state between the channels 207a and 207b.

The communication adjusting mechanism 208 performs the projection operation for projecting the injection needle 205 and the communication adjusting operation synchronously under control of the control circuit 213, or performs the storage operation for storing the injection needle 205 in the casing 202 by using the elastic force by the spring and the cutoff adjusting operation synchronously. Since the communication adjusting mechanism 208 has such a function, it includes a sheet holder 208a into which the channel forming unit 207 is inserted, a sheet member 208b arranged on the sheet holder 208a so as to cover the end of the channel forming unit 207 exposed on the sheet holder 208a, and a fixing member 208c that fixes a rim portion of the sheet member 208b in a state with the rim portion being stuck to the sheet holder 208a. The communication adjusting mechanism 208 further includes a pressing member 208d that applies a predetermined pressing force to the sheet member 208b, a holding board 208e that holds the proximal end of the injection needle 205, and associating members 208f and 208g that associates an operation of the pressing member 208d with an operation of the holding board 208e. The communication adjusting mechanism 208 further includes a spring 208h that generates the pressing force applied by the pressing member 208d, a spring board 208i that holds the spring 208h, and shape memory members 208j and 208k which are the drive source of the operation of the pressing member 208d and the operation of the holding board 208e.

The sheet holder 208a holds the sheet member 208b. Specifically, the sheet holder 208a is fixed on, for example, the casing 202, to hold the channel forming unit 207 in a state with the sheet holder 208a being penetrated by the channel forming unit 207, and also hold the sheet member 208b so as to cover an area in which the end of the channel forming unit 207 is exposed.

The sheet member 208b adjusts the communicated state or the cutoff state between the first channel and the second channel. Specifically, the sheet member 208b is formed of a watertight and flexible material such as a silicon sheet. The sheet member 208b is arranged on the sheet holding member 208a so as to cover the end of the channel forming unit 207 exposed on the sheet holder 208a, and fixed in a state with the rim portion being stuck to the sheet holder 208a by the fixing member 208c. When the predetermined pressing force is applied by the pressing member 208d, the sheet member 208b is maintained in the state of adhering to the end of the channel forming unit 208, thereby cutting off between the channels 207a and 207b, that is, a part of the medical fluid channel. An O-ring 212 is provided at the end of the channel forming unit 207, so that the watertightness between the end of the channel forming unit 207 and a contact surface of the sheet member 208b is ensured in the cutoff state. On the other hand, when the pressing force by the pressing member 208d decreases, the sheet member 208b is away from the end of the channel forming unit 207 by the discharge pressure or the like of the medical fluid circulated from the channel 207a, thereby connecting the channels 207a and 207b with each other.

The fixing member 208c fixes the rim portion of the sheet member 208b to the sheet holder 208a. Specifically, the fixing member 208c applies the pressing force to the rim portion of the sheet member 208b toward the sheet holder 208a so that the rim portion of the sheet member 208b adheres and is fixed to the sheet holder 208a. Since the fixing member 208c fixes the sheet member 208b in this manner, the central portion of the sheet member 208b, that is, the vicinity of the end of the channel forming unit 207 freely deforms the shape thereof corresponding to the pressing force of the pressing member 208d. At the same time, the sheet member 208b arranged in this manner prevents the medical fluid circulating between the channels 207a and 207b from leaking to the area in the casing 202 where components other than the channels 207a and 207b, for example, the pressing member 208d or the control circuit 213 is arranged.

The pressing member 208d applies the predetermined pressing force to the sheet member 208b to change the communicated state between the channels 207a and 207b to the cutoff state, thereby achieving the cutoff adjusting operation. The pressing member 208d changes the cutoff state to the communicated state between the channels 207a and 207b and achieves the communication adjusting operation by moving in a direction away from the sheet member 208b to decrease the pressing force or make the pressing force zero.

The holding board 208e holds the injection needle 205, with the injection needle 205 penetrating the holding board 208e. The holding board 208e functions as a projecting unit that projects the injection needle 205 from the casing using the driving force generated by the shape memory members 208j and 208k. The holding board 208e also has a function for storing the projected injection needle 205 in the casing 202 using the elastic force of the spring 208h transmitted via the associating members 208f and 208g.

The associating members 208f and 208g associate the operation of the pressing member 208d with the operation of the holding board 208e. Specifically, the associating members 208f and 208g are, for example, a filamentous member having flexibility, and are connected to the holding board 208e at one end, and to the pressing member 208d at the other end. More specifically, the associating members 208f and 208g are connected to each other at the ends so as to be positioned opposite to each other on the pressing member 208d or the holding board 208e. In this case, as shown in FIG. 25, the associating member 208f reaches the pressing member 208d from the holding board 208e via the guide members 211a to 211c. The associating member 208g reaches the pressing member 208d from the holding board 208e via the guide members 211d to 211f. The associating members 208f and 208g transmit the driving force by the shape memory members 208j and 208k to the pressing member 208d, to associate the projection operation of the injection needle 205 by the holding board 208e with the synchronization adjusting operation by the pressing member 208d. Further, the associating members 208f and 208g transmit the elastic force of the spring 208h to the holding board 208e, to associate the storage operation of the injection needle 205 by the holding board 208e with the cutoff adjusting operation by the pressing member 208d.

The guide members 211a to 211f are provided at predetermined positions in the casing 202, to regulate the routes of the associating members 208f and 208g. Specifically, the guide member 211a to 211f are realized using a pillar member having a smooth surface shape, a pulley, or the like, and arranged so that the moving directions of the associating members 208f and 208g that move with the projection operation of the injection needle 205 by the holding board 208e agrees with the moving directions of the associating members 208f and 208g when the pressing member 208d moves away from the sheet member 208b. A necessary number of the guide members needs only to be arranged in the casing 202, and the number of the guide members is not particularly limited to six.

The spring 208h generates the pressing force to be applied to the sheet member 208b by the pressing member 208d. Specifically, one end of the spring 208h is fixed to the spring board 208i, and the other end is fixed to the pressing member 208d, with the spring length being maintained shorter than a natural length. The thus arranged spring 208h functions so as to energize the elastic force (spring force) in a direction in which the sheet member 208b is positioned relative to the pressing member 208d. In this case, the spring 208h transmits the elastic force as the pressing force for pressing the sheet member 208b to the pressing member 208d.

The shape memory members 208j and 208k are the driving force of the communication adjusting mechanism 208 that performs the projection operation of the injection needle 205 and the communication adjusting operation, and generate the driving force for performing the projection operation of the injection needle 205 and the communication adjusting operation together. Specifically, the shape memory members 208j and 208k have cylindrical or coiled (for example, SMA coil) structures, and is formed of a shape memory alloy having a predetermined shape memory characteristic and a predetermined electrical resistivity. The shape memory member 208j and 208k are fixed to the guide 202a at respective one end, and to the holding board 208e at the other end, and have a sufficient length so that the injection needle 205 can be stored in the casing 202 under a temperature condition, for example, same as the temperature in the subject. In this case, the pressing member 208d presses the sheet member 208b using the elastic force by the spring 208h. The associating members 208f and 208g have such a length that the stored state of the injection needle 205 or the pressing state of the pressing member 208d relative to the sheet member 208b is not interrupted.

On the other hand, the shape memory member 208j and 208k change the shape thereof at a predetermined temperature, for example, under a temperature condition sufficiently higher than the temperature in the subject, and generate the predetermined driving force with the shape change (specifically, contraction deformation). The driving force is transmitted to the holding board 208e and to the pressing member 208d via the associating members 208f and 208g. In this case, the holding board 208e projects the injection needle 205 from the casing using the driving force (a projection operation of the injection needle 205). Synchronously with the projection of the injection needle 205, the pressing member 208d moves away from the sheet member 208b to adjust the channels 207a and 207b to the communicated state (a communication adjusting operation). The shape memory members 208j and 208k generate the driving force sufficient for performing the projection operation of the injection needle 205 and the communication adjusting operation synchronously.

When the channels 207a and 207b are adjusted to the communicated state due to the operation of the shape memory members 208j and 208k, the balloon 204 and the injection needle 205 are communicated with each other via the channels 207a and 207b. In this case, the balloon 204 discharges the medical fluid to the outside of the casing 202 (for example, to the desired region in the subject) via the channels 207a and 207b and the channel 205a of the injection needle 205. Therefore, the driving force generated by the shape memory members 208j and 208k is used for performing the projection operation of the injection needle 205, and also used for the communication adjusting operation for starting the medical-fluid discharge operation by the balloon 204 (that is, an example of the physical force for the discharge of the medical fluid). In other words, the shape memory members 208j and 208k that generate the physical force for the discharge of the medical fluid are the drive source for the discharge of the medical fluid.

The control circuit 213 functions so as to control the shape change of the shape memory members 208j and 208k according to the presence of power supply to the shape memory members 208j and 208k, and control the projection operation of the injection needle 205 and the medical-fluid discharge operation by the balloon 204 through the control of the shape change. Specifically, the control circuit 213 functions so as to supply the electric current to the shape memory members 208j and 208k when the body-insertable apparatus 201 introduced into the subject reaches a desired region in the subject, for example, the affected part. Joule heat is generated in the shape memory members 208j and 208k due to the flow of the current in the shape memory members 208j and 208k, and the temperature of the shape memory members 208j and 208k rise higher than the predetermined temperature resulting from the Joule heat. The shape memory members 208j and 208k change the shape thereof due to the temperature rise to generate the driving force for the projection operation of the injection needle and the communication adjusting operation, the holding board 208e projects the injection needle 205, and the pressing member 208d moves away from the sheet member 208b. As a result, the injection needle 205 is projected, and the balloon 204 performs the medical-fluid discharge operation.

On the other hand, the control circuit 213 decreases the temperature of the shape memory members 208j and 208k to lower than the predetermined temperature (for example, about the same temperature as that in the subject) by stopping the current supply to the shape memory members 208j and 208k. The shape memory members 208j and 208k lose the driving force relative to the communication adjusting mechanism 208, due to the temperature drop. In this case, the pressing member 208d presses the sheet member 208b, and the holding board 208e stores the injection needle 205 using the pressing force, that is, the elastic force of the spring 208h. As a result, the injection needle 205 is stored in the casing 202, and the balloon 204 stops the medical-fluid discharge operation.

As the configuration for specifying the current supply timing by the control circuit 213, for example, a timer mechanism can be provided, or a radio reception mechanism is incorporated therein and a control signal can be supplied from the outside.

Figure 26:
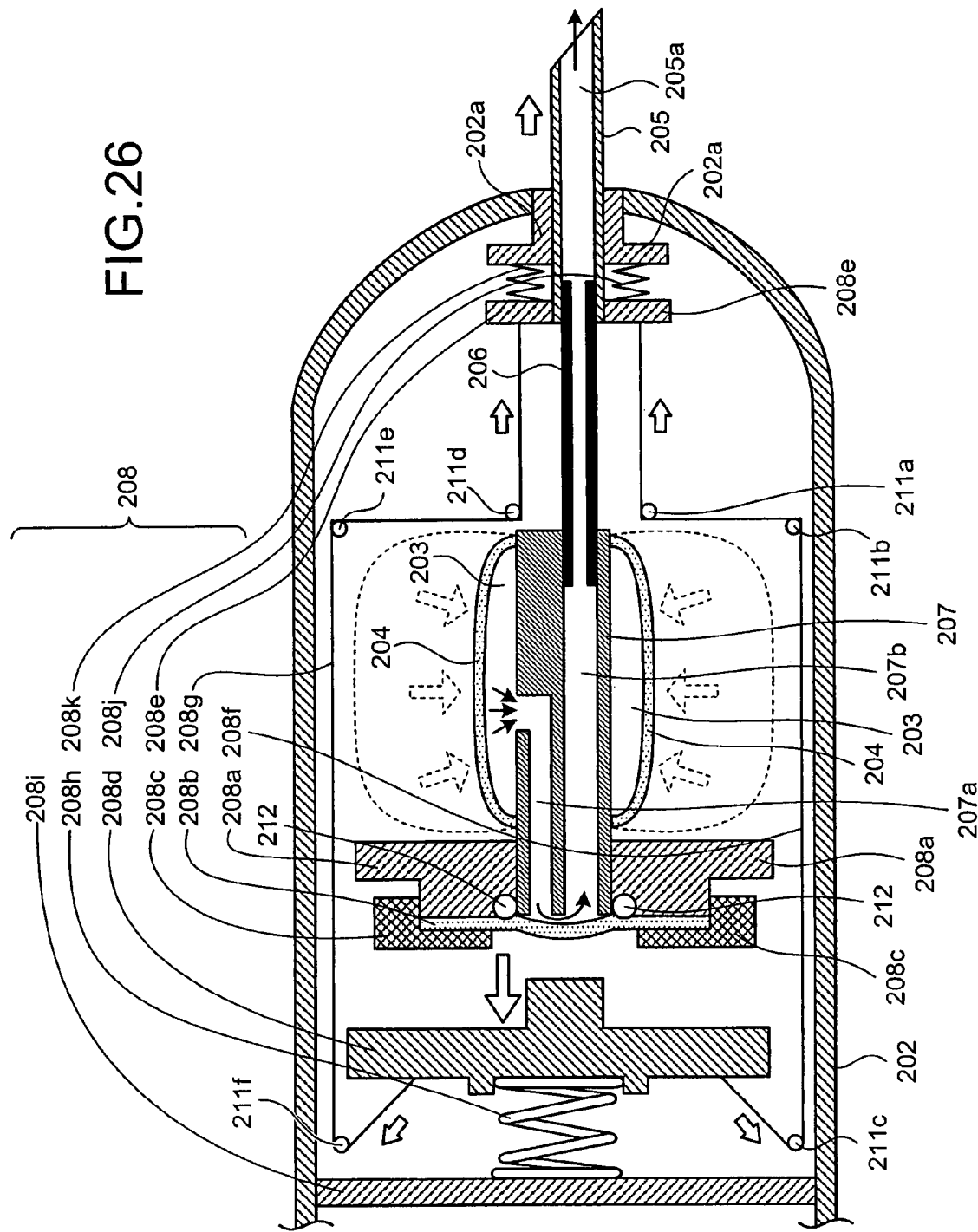
FIG. 26 is a schematic sectional view schematically exemplifying a state where the injection needle of the body-insertable apparatus according to the sixth embodiment is projected.

An operation of the body-insertable apparatus 201 is explained next. FIG. 26 is a schematic sectional view schematically exemplifying a state where the injection needle 205 of the body-insertable apparatus 201 is projected. The projection operation of the injection needle 205 and the medical-fluid discharge operation are explained with reference to FIG. 26.

The control circuit 213 supplies predetermined current to the shape memory members 208j and 208k to raise the temperature of the shape memory members 208j and 208k by generating the Joule heat in the shape memory members 208j and 208k. The shape memory members 208j and 208k change the shape thereof when the temperature rises higher than the predetermined temperature. Specifically, the shape memory members 208*j* and 208*k* are formed in a coiled shape and have been subjected to a shape memory treatment so that the length thereof in the longitudinal direction contracts at a high temperature. When the temperature rises higher than the predetermined temperature due to the Joule heat, the shape memory members 208*j* and 208*k* change the shape so that the longitudinal length becomes short. The shape memory members 208*j* and 208*k* generate the driving force due to the shape change. The generated driving force is transmitted to the holding board 208*e* and also transmitted to the pressing member 208*d* via the associating members 208*f* and 208*g*.

In this case, the holding board 208*e* projects the injection needle 205 from the casing 202 using the driving force, and pulls the associating members 208*f* and 208*g* toward the projecting direction of the injection needle 205. Synchronously therewith, the associating members 208*f* and 208*g* move the pressing member 208*d* in a direction away from the sheet member 208. The pressing member 208*d* decreases the pressing force against the sheet member 208*b* due to the operation of the associating members 208*f* and 208*g*, to achieve the communication adjusting operation by releasing the adhesion state between the sheet member 208*b* and the end of the channel forming unit 207. The channels 207*a* and 207*b* are adjusted to the communicated state by the communication adjusting operation, which triggers the discharge operation of the balloon 204. In this case, the medical fluid in the storage chamber 203 is discharged from the end of the projected injection needle 205 by sequentially passing through the channels 207*a* and 207*b*, the tube 206, and the channel 205*a* of the injection needle 205 due to the medical-fluid discharge operation by the balloon 204. The projected injection needle 205 punctures the desired region in the subject such as the affected part, to inject the medical fluid to the desired region.

The communication adjusting mechanism 208 having such a configuration functions as the discharge starting unit that performs the projection operation of the injection needle 205 and the communication adjusting operation synchronously, using the driving force generated by the shape memory members 208*j* and 208*k*, to project the injection needle 205 from the casing 202, thereby starting the medical-fluid discharge operation of the balloon 204. The balloon 204 can inject a desired amount of medical fluid to the desired region in the subject via the injection needle 205 by using its contraction force to perform the medical-fluid discharge operation.

On the other hand, when the control circuit 213 stops supply of the current to the shape memory members 208*j* and 208*k*, generation of the Joule heat is suppressed, and the temperature of the shape memory members 208*j* and 208*k* gradually decreases, and releases the contraction deformation to lose the driving force. In this case, the pressing member 208*d* presses the sheet member 208*b* by using the elastic force of the spring 208*h*, and changes the communicated state between the channels 207*a* and 207*b* to the cutoff state. The balloon 204 stops the medical-fluid discharge operation due to the cutoff adjusting operation of the pressing member 208*d*. The elastic force by the spring 208*h* is transmitted to the holding board 208*e* via the associating members 208*f* and 208*g*. That is, the pressing member 208*d* moves the holding board 208*e* in the direction toward the channel forming unit 207 synchronously with the cutoff adjusting operation, by using the associating members 208*f* and 208*g*. The holding board 208*e* stores the injection needle 205 in the casing 202 due to the operation of the pressing member 208*d*. The communication adjusting mechanism 208 can stop the medical-fluid discharge operation by the balloon 204 and can store the injection needle 205 in the casing 202 by using the elastic force of the spring 208*h*.

At a distal end in time when the communication adjusting mechanism 208 stops the medical-fluid discharge operation by the balloon 204, if the balloon 204 has not yet discharged the medical fluid in an amount equal to or larger than the predetermined amount, the balloon 204 has an elastic force (contraction force) of a level capable of resuming the contraction. Therefore, when the communication adjusting mechanism 208 performs the communication adjusting operation again based on the control of the control circuit 213, the channels 207*a* and 208*b* are adjusted to the communicated state again, and the balloon 204 resumes the medical-fluid discharge operation. Since the communication adjusting mechanism 208 repeats the communication adjusting operation and the cutoff adjusting operation in this manner, the balloon 204 can repeat the medical-fluid discharge operation intermittently, until the medical fluid in an amount equal to or larger than the predetermined amount has been discharged.

As explained above, in the sixth embodiment of the present invention, the operation of the pressing member for adjusting the medical fluid channel to the communicated state or to the cutoff state and the operation of the holding board holding the injection needle are associated with each other by the associating members, and the projection operation of the injection needle from the casing by the holding board and the operation for adjusting the medical fluid channel to the communicated state by the pressing member are performed synchronously, by using the driving force generated by the shape change of the shape memory members. Accordingly, by supplying predetermined power to the shape memory members, the medical fluid channel can be adjusted to the communicated state to start the medical-fluid discharge operation, and the injection needle can be projected. Therefore, it is not necessary to consume new driving power for executing the projection operation of the injection needle, thereby realizing the body-insertable apparatus that can execute the projection operation of the injection needle in a power saving manner.

Further, the operation of the pressing member for adjusting the medical fluid channel to the cutoff state by using the elastic force of the spring and the operation of the holding member for storing the injection needle in the casing are synchronously performed. Accordingly, it is not necessary to consume new driving power for executing the storage operation of the injection needle, thereby realizing the body-insertable apparatus that can execute the storage operation of the injection needle in a power saving manner. Thus, the body-insertable apparatus that can store the injection needle in the casing can puncture the injection needle only to a necessary spot in the subject. Further, by adjusting the medical fluid channel to the cutoff state, the medical-fluid discharger can be suspended, and hence by repetitively adjusting the medical fluid channel to the communicated state or to the cutoff state, the medical fluid can be discharged intermittently.

Further, by using the holding board for projecting or storing the injection needle, the pressing member that adjusts the medical fluid channel to the communicated state or to the cutoff state, and the associating members that associate the operation of these members, a synchronization adjusting mechanism that can perform the projection operation of the injection needle and the communication adjusting operation of the medical fluid channel synchronously can be integrally formed. By using the synchronization adjusting mechanism adopting such a configuration, a new drive mechanism for executing the projection operation of the injection needle need not be provided, and hence the drive mechanism for injecting the medical fluid to the desired region in the subject can be simplified, thereby realizing a downsized body-insertable apparatus easily.

Further, the communication adjusting mechanism performs the operation of the pressing member for adjusting the medical fluid channel to the cutoff state and the operation of the holding board for storing the injection needle in the casing synchronously. Therefore, a new drive mechanism for executing the storage operation of the injection needle need not be provided, and hence the drive mechanism for storing the injection needle after finishing injection of the medical fluid to the desired region in the subject can be simplified, thereby realizing the downsized body-insertable apparatus easily.

Further, an expandable balloon is used to form the storage chamber of the medical fluid, and the medical-fluid discharge operation is executed by using the contraction force of the balloon. Therefore, it is not necessary to consume new driving power for executing the medical-fluid discharge operation, thereby promoting power saving of the body-insertable apparatus according to the present invention.

The body-insertable apparatus adopting such a configuration can realize downsizing of the apparatus and can include the local injection function for injecting the medical fluid to the desired region in the subject. Accordingly, the body-insertable apparatus can execute the local injection operation from projecting the injection needle to inject the medical fluid to the desired region in the subject until the injection needle is stored, with less power consumption.

First Modification of Sixth Embodiment

A first modification of the body-insertable apparatus 201 according to the sixth embodiment of the present invention is explained next. In the sixth embodiment, the shape memory members 208$j$ and 208$k$ as the drive source are fitted to the holding board 208$e$ that holds the injection needle 205. The holding board 208$e$ projects the injection needle 205 due to the contraction operation of the shape memory members 208$j$ and 208$k$, and the pressing member 208$d$ moves away from the sheet member 208$b$ synchronously therewith. However, in the first modification of the sixth embodiment, the shape memory members 208$j$ and 208$k$ as the drive source are fitted to the pressing member 208$d$, and the pressing member 208$d$ moves away from the sheet member 208$b$ due to the contraction operation of the shape memory members 208$j$ and 208$k$ to project the injection needle 205 synchronously therewith.

Figure 27:
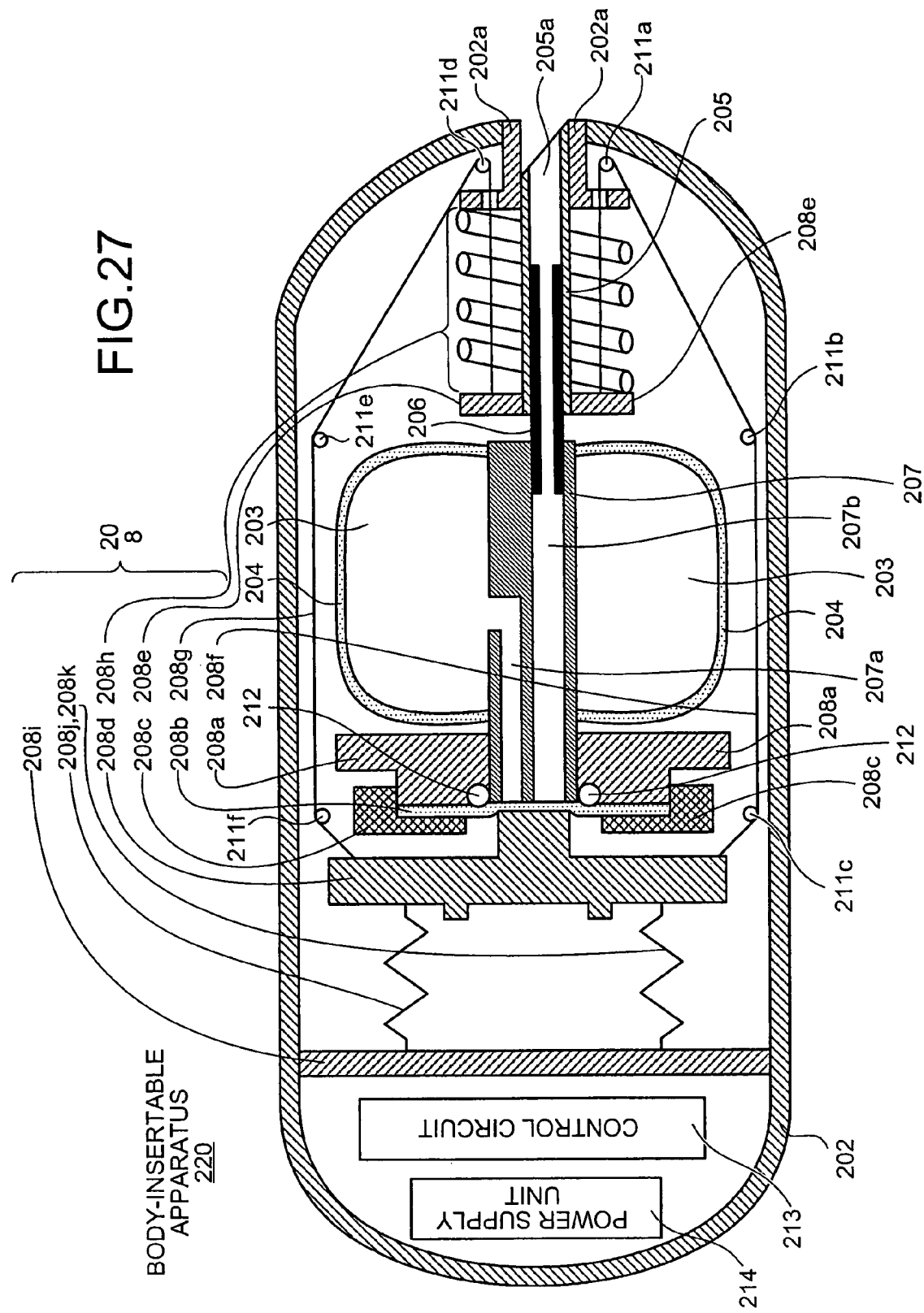
FIG. 27 is a schematic sectional view schematically showing one configuration example of the body-insertable apparatus, which is a first modification of the sixth embodiment according to the present invention.

FIG. 27 is a schematic sectional view schematically showing one configuration example of the body-insertable apparatus, which is the first modification of the sixth embodiment according to the present invention. As shown in FIG. 27, in this body-insertable apparatus 220, shape memory members 208$j$ and 208$k$ as the drive source are provided instead of the spring 208$h$, and a spring 208$h$ is provided instead of the shape memory members 208$j$ and 208$k$. Other configurations are the same as those of the sixth embodiment, and like reference letters or numerals refer to like constituent elements.

Specifically, one end of the spring 208$h$ is fixed to the guide 202$a$, and the other end is fixed to the holding board 208$e$, with the spring length being maintained shorter than a natural length. The thus arranged spring 208$h$ functions so as to energize the elastic force in a direction of storing the injection needle 205 relative to the holding board 208$e$.

In the body-insertable apparatus 220, as shown in FIG. 27, the associating member 208$f$ extends from the holding board 208$e$, passes near the spring 208$h$, penetrates the guide 202$a$ slidably, and reaches the surface side of the pressing member 208$d$ (the side opposite to the sheet member 208$b$) via the guide members 211$a$ to 211$c$. The associating member 208$g$ extends from the holding board 208$e$, passes near the spring 208$h$, penetrates the guide 202$a$ slidably, and reaches the surface side of the pressing member 208$d$ via the guide members 211$d$ to 211$f$. In this case, the guide members 211$a$ to 211$f$ are arranged inside the casing 202, so as to realize the path of the associating members 208$f$ and 208$g$.

On the other hand, the shape memory members 208$j$ and 208$k$ are fixed to the rear face (the side opposite to the spring board 208$i$) of the pressing member 208$d$ at one end and to the spring board 208$i$ at the other end, and has a length sufficient for the pressing member 208$d$ to abut against the sheet member 208$b$ under a temperature condition, for example, same as the temperature inside the subject. The shape memory members 208$j$ and 208$k$ change the shape thereof (specifically, are contraction-deformed) at a predetermined temperature, for example, under a temperature condition sufficiently higher than the temperature in the subject, and act so that the pressing member 208$d$ moves away from the sheet member 208$b$.

When the shape memory members 208$j$ and 208$k$ have a temperature lower than the predetermined temperature, that is, when the shape memory members 208$j$ and 208$k$ are not contraction-deformed, the pressing member 208$d$ presses the sheet member 208$b$ by using the elastic force of the spring 208$h$ transmitted by the associating members 208$f$ and 208$g$. Thereafter, when the shape memory members 208$j$ and 208$k$ are contraction-deformed based on the control of the control circuit 213, the pressing member 208$d$ is moved so as to be away from the sheet member 208$b$ by the operation of contraction deformation (that is, the driving force generated by the shape memory members 208$j$ and 208$k$). At the same time, the driving force is transmitted to the holding board 208$e$ by the associating members 208$f$ and 208$g$. In this case, the holding board 208$e$ is made to associate with the operation of the pressing member 208$d$, and is moved in a direction of projecting the injection needle 205 by the associating members 208$f$ and 208$g$. Thus, the holding board 208$e$ uses such a driving force to project the injection needle 205 from the casing 202.

Thereafter, when the control circuit 213 stops current supply to the shape memory members 208$j$ and 208$k$, the shape memory members 208$j$ and 208$k$ stops the contraction deformation to lose the driving force. In this case, the holding board 208$e$ stores the injection needle 205 in the casing 202 by using the elastic force of the spring 208$h$, and pulls the associating members 208$f$ and 208$g$ along the direction of storing the injection needle 205. The associating members 208$f$ and 208$g$ transmit the elastic force by the spring 208$h$ to the pressing member 208$d$. In other words, the pressing member 208$d$ is moved in a direction of pressing the sheet member 208$b$ by the associating members 208$f$ and 208$g$, synchronously with the storage operation by the holding board 208$e$. The pressing member 208$d$ presses the sheet member 208$b$ by using the elastic force of the spring 208$h$.

Thus, the synchronization adjusting mechanism 208 uses the driving force generated by the shape memory members 208$j$ and 208$k$, to isolate the pressing member 208$d$ from the sheet member 208$b$, thereby achieving the communication adjusting operation, and pulls the holding board 208$e$ synchronously with the communication adjusting operation, to project the injection needle 205 from the casing 202. The synchronization adjusting mechanism 208 further uses the elastic force of the spring 208$h$ to move the holding board 208$e$ in a direction of storing the injection needle 205, thereby storing the injection needle 205 in the casing 202, and presses the pressing member 208$d$ against the sheet member 208$b$ synchronously with the storage operation of the injection needle 205, to achieve the cutoff adjusting operation.

The body-insertable apparatus 220 adopting such a configuration can have the same function as that of the body-insertable apparatus 201 according to the sixth embodiment. For example, the body-insertable apparatus 220 can project the injection needle 205 due to the contraction deforming operation of the shape memory members 208*j* and 208*k* (that is, the driving force generated by the shape memory members 208*j* and 208*k*), and discharge the medical fluid, as in the body-insertable apparatus 201. The body-insertable apparatus 220 can obtain the same operations and effects as those of the body-insertable apparatus 201.

Second Modification of Sixth Embodiment

A second modification of the body-insertable apparatus 201 in the sixth embodiment of the present invention is explained next. In the sixth embodiment, the balloon 204 discharges the medical fluid according to the contraction operation thereof. In the second modification of the sixth embodiment, however, a piston mechanism that forms a storage chamber for storing the medical fluid is provided, and the piston mechanism uses the elastic force of the spring to compress the storage chamber, thereby discharging the medical fluid.

Figure 28:
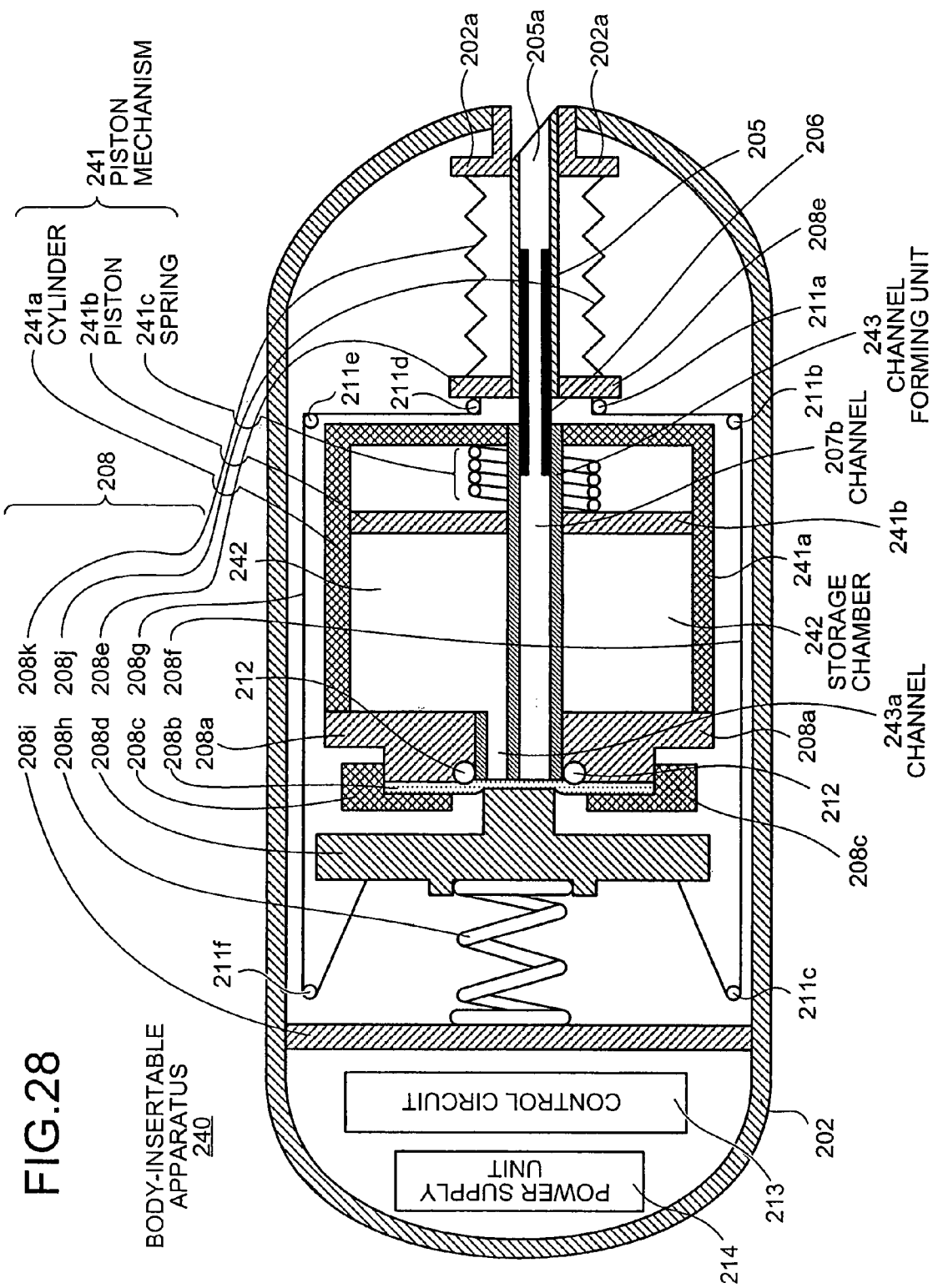
FIG. 28 is a schematic sectional view schematically showing one configuration example of the body-insertable apparatus, which is a second modification of the sixth embodiment according to the present invention.

FIG. 28 is a schematic sectional view schematically showing one configuration example of the body-insertable apparatus, which is the second modification of the sixth embodiment according to the present invention. As shown in FIG. 28, this body-insertable apparatus 240 includes a piston mechanism 241 instead of the balloon 204 in the body-insertable apparatus 201 according to the sixth embodiment, and a channel forming unit 243 instead of the channel forming unit 207. Other configurations are the same as those of the sixth embodiment, and like reference letters or numerals refer to like constituent elements.

The piston mechanism 241 forms therein a storage chamber 242 for pre-storing the medical fluid, and functions as the medical-fluid discharger that discharges the medical fluid by compressing the storage chamber 242. Specifically, the piston mechanism 241 has a cylinder 241*a* that forms the most part of an external wall thereof, a piston 241*b* that slides in the cylinder 241*a* so as to compress the storage chamber 242, and a spring 241*c* that applies a predetermined elastic force to the piston 241*b*.

The cylinder 241*a* forms the most part of the external wall of the piston mechanism 241, and is attached to a sheet holder 208*a* so that an opening thereof is covered with a rear face (a face where the sheet member 208*b* is not arranged). In the cylinder 241*a*, the piston 241*b* is slidably provided, and the spring 241*c* is provided between the bottom thereof and the piston 241*b*. In this case, the piston 241*b* is provided so as to be slidably penetrated by the channel forming unit 243 provided in the sheet holder 208*a*, and the spring 241*c* is provided such that the channel forming unit 243 passes the center of the coil. The cylinder 41 is provided such that bottom is penetrated by the channel forming unit 243.

In this case, the storage chamber 242 is formed in an area surrounded by the rear face of the sheet holder 208*a*, the piston 241*b*, and a part of the cylinder 241*a* (that is, a portion positioned between the rear face of the sheet holder 208*a* and the piston 241*b*).

The piston 241*b* discharges the medical fluid by compressing the storage chamber 242. Specifically, the piston 241*b* slides between the internal wall of the cylinder 241*a* and an external wall of the channel forming unit 243 by using the elastic force of the spring 241*c*, when the channels 243*a* and 207*b* are communicated with each other due to the operation of the communication adjusting mechanism 208, thereby compressing the storage chamber 242 to discharge the medical fluid.

The spring 241*c* applies a predetermined elastic force to the piston 241*b*. Specifically, the spring 241*c* is fixed to the bottom of the cylinder 241*a* at one end, and to the piston 241*b* at the other end, with the spring length being maintained shorter than a natural length. The thus arranged spring 241*c* functions so as to energize the elastic force (spring force) in a direction of compressing the storage chamber 242 relative to the piston 241*b*.

The channel forming unit 243 includes therein a channel 243*a* connecting to the storage chamber 242 and a channel 207*b* connecting to the channel 205*a* of the injection needle 205 via the tube 206. In the channel forming unit 243, one end forming an opening of the channels 243*a* and 207*b* is provided in the sheet holder 208*a*, as in the channel forming unit 207, and the other end thereof is proved so as to penetrate the bottom of the cylinder 241*a*. In this case, the channel forming unit 243 is adjusted so as to maintain the channels 243*a* and 207*b* in the communicated state or the cutoff state due to the operation of the communication adjusting mechanism 208 (the communication adjusting operation or the cutoff adjusting operation).

The body-insertable apparatus 240 adopting such a configuration can perform the medical-fluid discharge operation like the balloon 204 of the body-insertable apparatus 201 according to the sixth embodiment, and can have the same function as that of the body-insertable apparatus 201. Accordingly, the body-insertable apparatus 240 can obtain the same operations and effects as those of the body-insertable apparatus 201.

Seventh Embodiment

A seventh embodiment of the present invention is explained next. In the sixth embodiment, the associating members 208*f* and 208*g* are used to associate the operation of the pressing member 208*d* (for example, the communication adjusting operation) with the operation of the holding board 208*e* (for example, the projection operation of the injection needle 205). In the seventh embodiment, however, the injection needle is directly provided on the pressing member 208*d*, so that the operation of the pressing member 208*d* and the projection operation of the injection needle are performed simultaneously.

Figure 29:
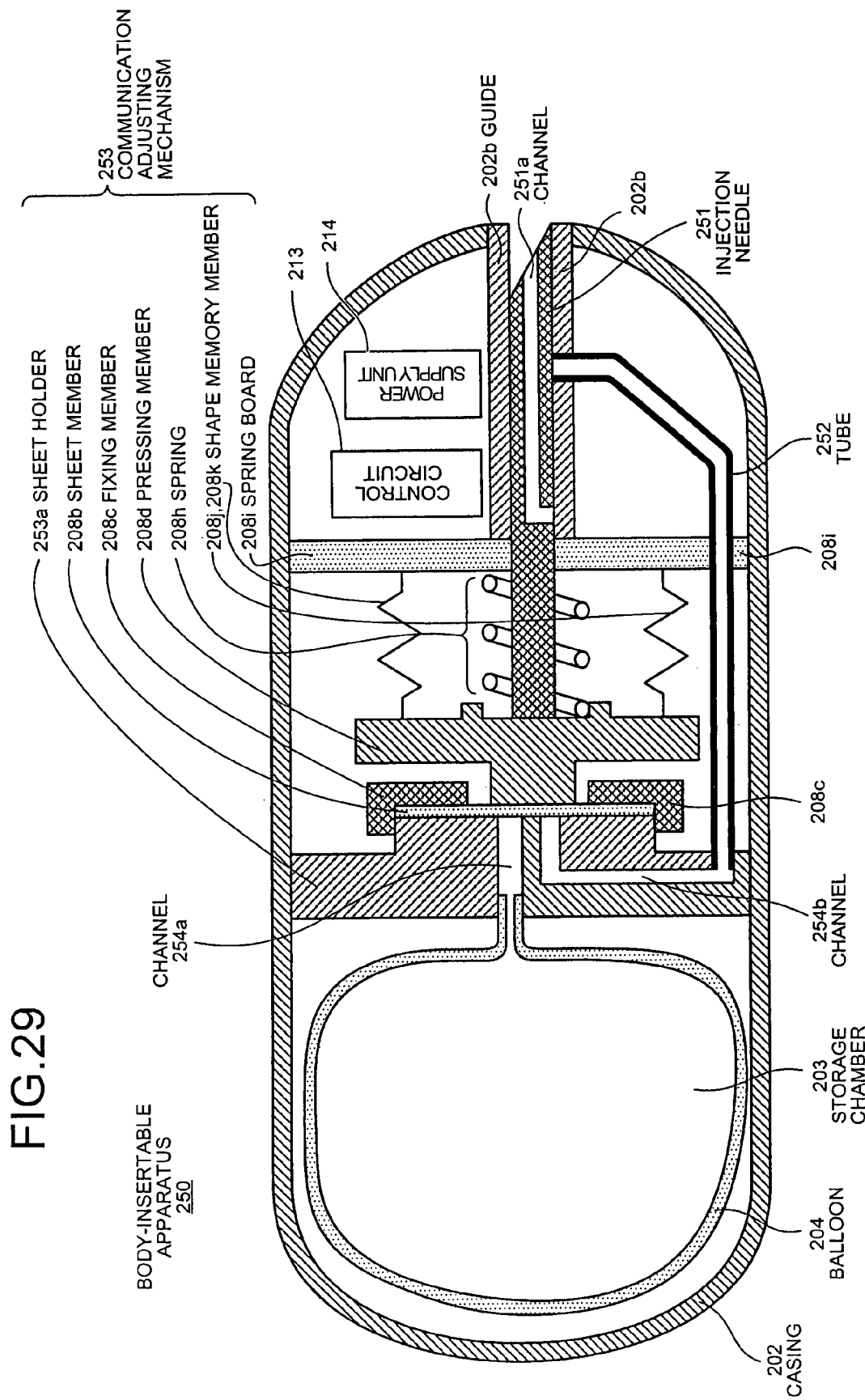
FIG. 29 is a schematic sectional view schematically showing one configuration example of a body-insertable apparatus according to a seventh embodiment of the present invention.

FIG. 29 is a schematic sectional view schematically showing one configuration example of the body-insertable apparatus according to a seventh embodiment of the present invention. As shown in FIG. 29, this body-insertable apparatus 250 includes, inside the casing 202, an injection needle 251 for injecting the medical fluid to a desired region in the subject, a tube 252 for circulating the medical fluid to a channel 251*a* formed in the injection needle 251, and a balloon 204 as the medical-fluid discharger that forms the storage chamber 203. Further, the body-insertable apparatus 250 includes a communication adjusting mechanism 253 that adjusts the storage chamber 203 and the tube 252 to the communicated state and projects the injection needle 251 from the casing 202, the control circuit 213 that controls the driving state of the communication adjusting mechanism 253, and the power supply unit 214 that supplies driving power to the control circuit 213.

The injection needle 251 uses the drive source for the discharge of the medical fluid to project from the casing 202, and injects the medical fluid to the desired region in the subject. Specifically, the injection needle 251 has a channel 251a formed therein for connecting a distal end side (a side forming a sharp point) for puncturing the subject and a predetermined position on the side. Further, the injection needle 251 is fixed to the pressing member 208d in the communication adjusting mechanism 253 at the rear end. The injection needle 251 is provided so as to be inserted slidably in the guide 202b having a cylindrical structure provided at an entrance of the injection needle in the casing 202. The guide 202b regulates the moving direction of the injection needle 251 so that the injection needle 251 can be smoothly projected or stored, and prevents the medical fluid circulated to the channel 251a in the injection needle 251 from leaking to an area in the casing 202 where components other than the tube 252, for example, the control circuit 213 or the communication adjusting mechanism 253 is arranged.

The tube 252 forms a channel for circulating the medical fluid to the channel 251a in the projected injection needle 251. Specifically, the tube 252 is connected to the guide 202b at one end, and to the sheet holder 253a in the communication adjusting mechanism 253 at the other end. More specifically, the tube 252 is connected to a predetermined position of the guide 202b so as to be communicated with the channel 251a when the injection needle 251 is projected from the casing 202. The tube 252 communicates with the channel 254b formed in the sheet holder 253a, and communicates with the channel 251a of the injection needle 251 projected from the casing 202.

The communication adjusting mechanism 253 functions so as to perform the communication adjusting operation for adjusting between the storage chamber 203 and the tube 252 (that is, the channel 251a of the injection needle 251) to the communicated state based on the control of the control circuit 213. The communication adjusting mechanism 253 projects the injection needle 251 from the casing synchronously with the communication adjusting operation, and stores the injection needle 251 in the casing 202 synchronously with the cutoff adjusting operation. The communication adjusting mechanism 253 has a sheet holder 253a having a channel 254a connecting to the storage chamber 203 and a channel 254b connecting to the tube 252 formed therein, a sheet member 208b arranged on the sheet holder 253a so as to cover openings of the channels 254a and 254b, and a fixing member 208c that fixes a rim portion of the sheet member 208b in a state closely adhering to the sheet holder 208a. The communication adjusting mechanism 253 further includes a pressing member 208d that applies a predetermined pressing force to the sheet member 208b, a spring 208h that generates the pressing force applied by the pressing member 208d, a spring board 208i that holds the spring 208h, and shape memory members 208j and 208k that change a position of the pressing member 208d relative to the sheet member 208b. The sheet member 208b, the fixing member 208c, the pressing member 208d, the spring 208h, the spring board 208i, and the shape memory members 208j and 208k function like the communication adjusting mechanism 208 in the sixth embodiment.

In the sheet holder 253a, the balloon 204 is connected to the channel 254a and the tube 252 is connected to the channel 254b. When the pressing member 208d reduces the pressing force against the sheet member 208b due to the operation of the shape memory members 208j and 208k, the adhesion state between the sheet holder 253a and the openings of the channels 254a and 254b is released, to adjust the channels 254a and 254b to the communicated state. In such a communicated state, the balloon 204 starts the medical-fluid discharge operation, and the sheet holder 253a circulates the medical fluid to the tube 252 via the channels 254a and 254b. On the other hand, when the pressing member 208d presses the sheet member 208b by using the elastic force of the spring 208h, in the sheet holder 54a, the sheet member 208b and the openings of the channels 254a and 254b are turned to the adhesion state, and the channels 254a and 254b are adjusted to the cutoff state. In such a cutoff state, in the sheet holder 253a, circulation of the medical fluid between the storage chamber 203 and the tube 252 (that is, the channel 251a in the injection needle 251) is cut off. As a result, the balloon 204 stops the medical-fluid discharge operation.

The injection needle 251 is connected to the rear face (the side opposite to the spring board 208i) of the pressing member 208d. The injection needle 251 fixed to the pressing member 208d in this manner slides in the guide 202b, synchronously with the operation of the pressing member 208d. Specifically, the injection needle 251 projects from the casing 202, synchronously with the operation of the pressing member 208d in a direction away from the sheet member 208b (that is, the communication adjusting operation for adjusting the channels 254a and 254b to the communicated state). In this projected state, the injection needle 251 connects the channel 251a to the tube 252. Thereafter, the projected injection needle 251 returns to the casing 202, that is, is stored in the casing 202, synchronously with the operation of the pressing member 208d in a direction of pressing the sheet member 208b (that is, the cutoff adjusting operation for adjusting the channels 254a and 254b to the cutoff state).

Figure 30:
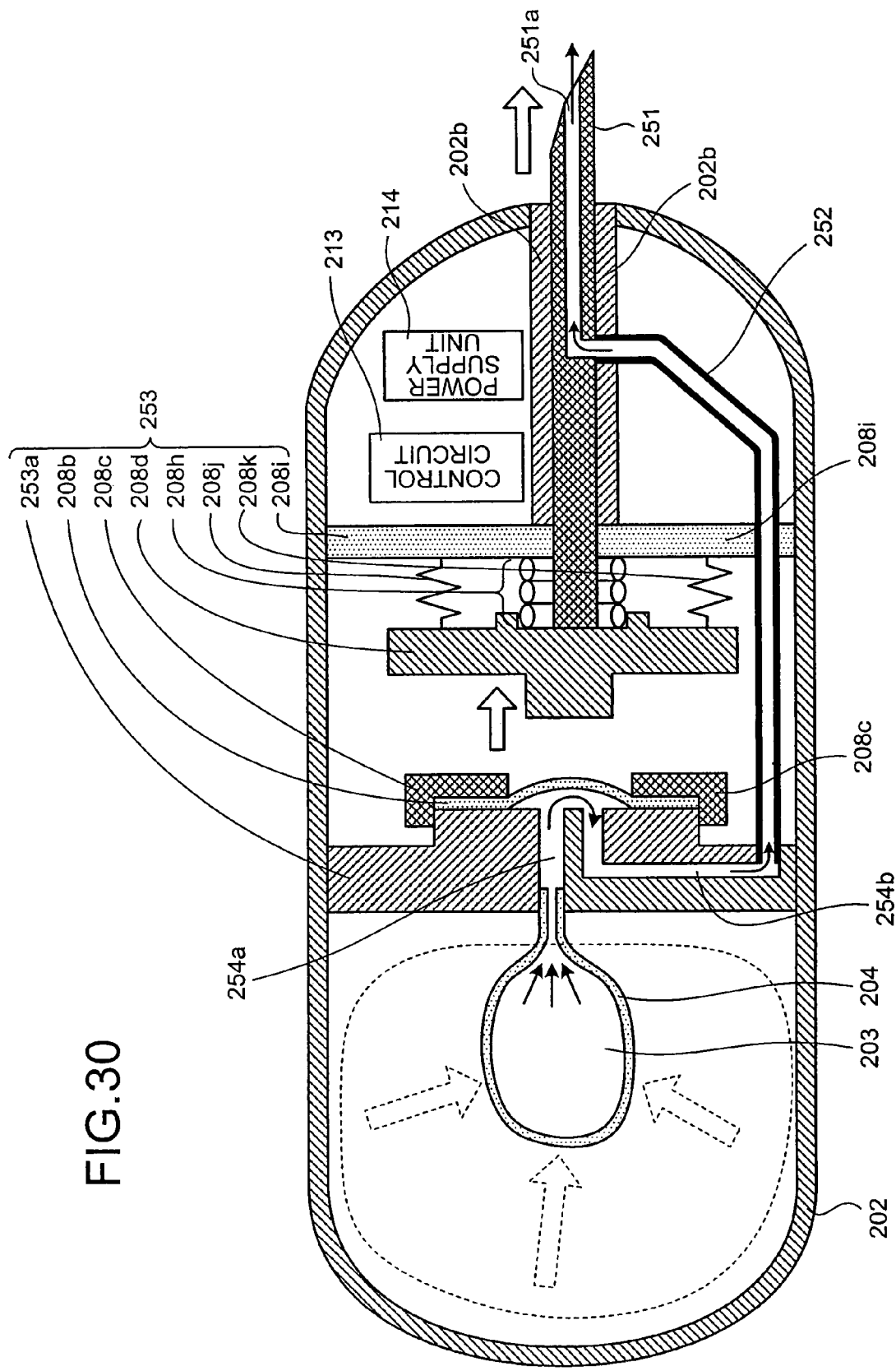
FIG. 30 is a schematic sectional view schematically exemplifying a state where the injection needle of the body-insertable apparatus according to the seventh embodiment is projected.

An operation of the body-insertable apparatus 250 is explained next. FIG. 30 is a schematic sectional view schematically exemplifying a state where the injection needle 251 of the body-insertable apparatus 250 is projected. The projection operation of the injection needle 251 and the medical-fluid discharge operation are explained with reference to FIG. 30.

The control circuit 213 performs drive control for the communication adjusting mechanism 253 so that the balloon 204 starts the medical-fluid discharge operation. Specifically, the control circuit 213 supplies predetermined current to the shape memory members 208j and 208k, which are the drive source of the communication adjusting mechanism 253, to control the shape change thereof (contraction deformation). The shape memory members 208j and 208k generate a driving force due to the shape change, and pulls the pressing member 208d using the driving force. In this case, the pressing member 208d moves in a direction away from the sheet member 208b due to the driving force, to decrease the pressing force against the sheet member 208b. As a result, the pressing member 208d achieves the communication adjusting operation, and the balloon 204 starts the medical-fluid discharge operation.

The pressing member 208d moves in the direction away from the sheet member 208b in this manner, to push the injection needle 251. The injection needle 251 slides in the guide 202b due to the operation of the pressing member 208d so that the tube 252 is communicated with the channel 251a, and projects from the casing 202. In other words, the pressing member 208d performs the communication adjusting operation and the projection operation of the injection needle 251 simultaneously, due to the driving force of the shape memory members 208j and 208k.

In such a state that the injection needle 251 is projected, the storage chamber 203 and the channel 251a of the injection needle 251 are communicated with each other via the channels 254a and 254b and the tube 252, and the balloon 204 continues the medical-fluid discharge operation. Due to the medical-fluid discharge operation, the medical fluid in the storage chamber 203 passes through the channels 254a and 254b, the tube 252, and the channel 251a sequentially, and is discharged from the distal end of the injection needle 251.

The communication adjusting mechanism 253 having such a configuration functions as the discharge starting unit that performs the projection operation of the injection needle 205 and the communication adjusting operation synchronously, using the driving force generated by the shape memory members 208j and 208k, to project the injection needle 251 from the casing 202, thereby starting the medical-fluid discharge operation of the balloon 204. The injection needle 251 punctures a desired region in the subject, for example, the affected part, and balloon 204 can inject a desired amount of medical fluid to the desired region in the subject via the injection needle 251 by using its contraction force to perform the medical-fluid discharge operation.

Thereafter, when the control circuit 213 stops current supply to the shape memory members 208j and 208k, the shape memory members 208j and 208k stop the contraction deformation and lose the driving force. In this case, the pressing member 208d presses the sheet member 208b by using the elastic force of the spring 208h, and pulls the injection needle 205 back into the casing 202. Due to the operation of the pressing member 208d, the channels 254a and 254b are adjusted to the cutoff state, and the injection needle 251 is stored in the casing 202.

If the balloon 204 has not discharged the medical fluid in an amount equal to or more than the predetermined amount, when the channels 254a and 254b are adjusted to the cutoff state, the balloon 204 stops (suspends) the medical-fluid discharge operation. Thereafter, when the pressing member 208d moves away from the sheet member 208b again and projects the injection needle 251, the channels 254a and 254b are again adjusted to the communicated state, and the balloon 204 resumes the medical-fluid discharge operation. Thus, since the communication adjusting mechanism 253 repeats the communication adjusting operation and the cutoff adjusting operation, the balloon 204 can intermittently repeat the medical-fluid discharge operation until the desired amount of medical fluid has been discharged.

The body-insertable apparatus 250 adopting such a configuration has the same function as that of the body-insertable apparatus 201 according to the sixth embodiment, and hence the body-insertable apparatus 250 can obtain the operations and effects of the body-insertable apparatus 201.

Further, in the body-insertable apparatus 250, the injection needle 251 is directly fixed to the pressing member 208d, the operation of the pressing member 208d moving away from the sheet member 208b is associated with the projection operation of the injection needle 251 from the casing 202, and the operation of the pressing member 208d pressing the sheet member 208b is associated with the storage operation of the injection needle 251 in the casing 202. Accordingly, it is not necessary to provide a member for associating the movement of the pressing member with the movement of the injection needle, as exemplified by the synchronization members 208f and 208g, thereby promoting space saving inside the casing 202 and downsizing of the apparatus.

Modification of Seventh Embodiment

A modification of the body-insertable apparatus 250 in the seventh embodiment of the present invention is explained next. In the seventh embodiment, the injection needle is directly provided in the pressing member 208d that adjusts the communicated state between the channels 254a and 254b. In the modification of the seventh embodiment, however, the injection needle is connected to a channel forming unit fixed to the pressing member that adjusts the communicated state between the channel in the injection needle and the balloon, so that the projection operation of the injection needle is performed together with the operation of the channel forming unit.

Figure 31:
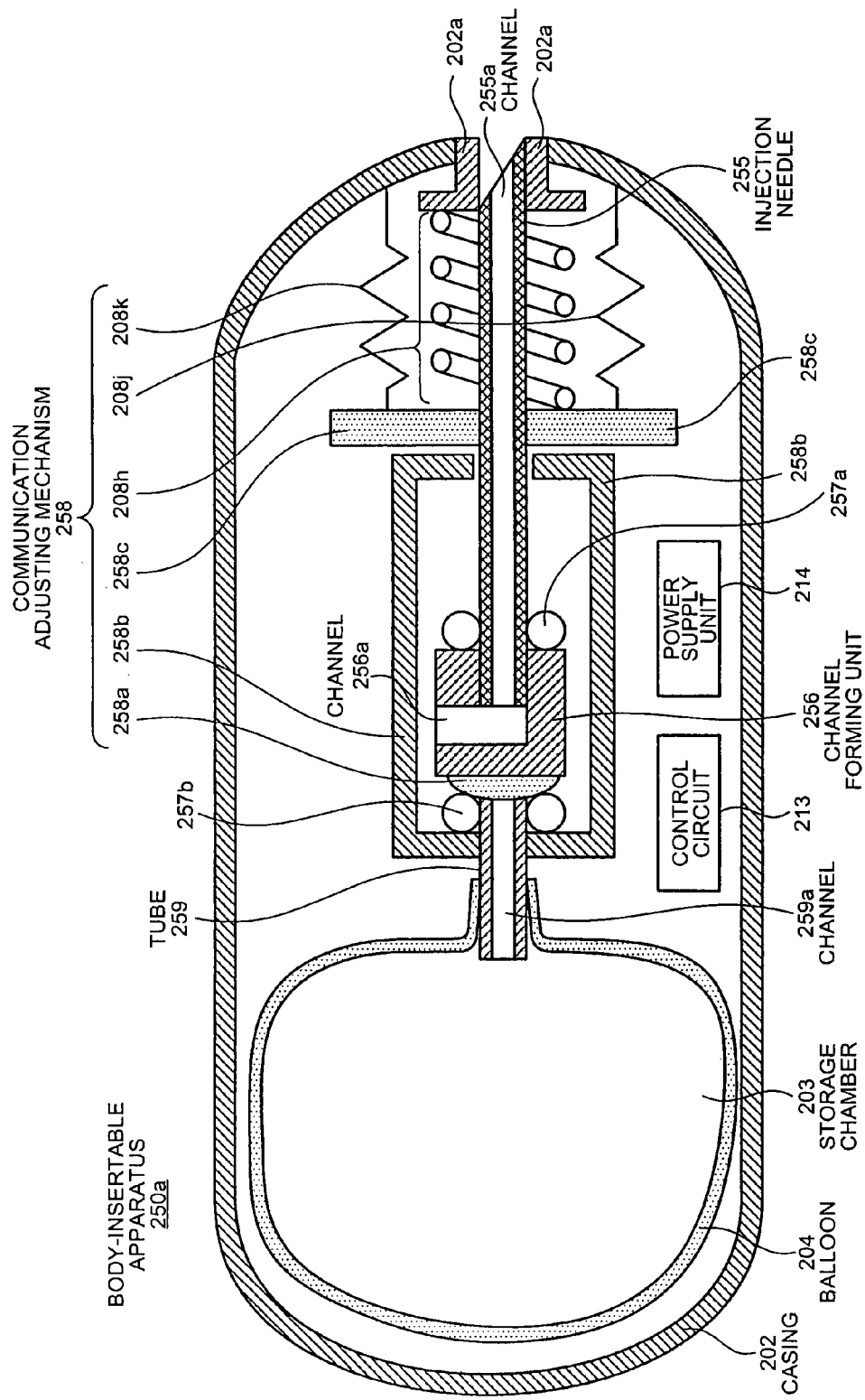
FIG. 31 is a schematic sectional view schematically showing one configuration example of the body-insertable apparatus, which is a modification of the seventh embodiment according to the present invention.

FIG. 31 is a schematic sectional view schematically showing one configuration example of the body-insertable apparatus, which is the modification of the seventh embodiment according to the present invention. As shown in FIG. 31, the body-insertable apparatus 250a has an injection needle 255 instead of the injection needle 251 in the body-insertable apparatus 250 according to the seventh embodiment and a communication adjusting mechanism 258 instead of the communication adjusting mechanism 253. Further, the body-insertable apparatus 250a has a channel forming unit 256 and a tube 259 that respectively form channels 256a and 259a for connecting the inside of the balloon 204 (storage chamber 203) to a channel 255a in the injection needle 255, instead of the tube 252 and the sheet holder 253a in the body-insertable apparatus 250. The body-insertable apparatus 250a further includes an O-ring 257a as a leakage preventing unit that prevents leakage of the medical fluid to the outside of the channel, and an O-ring 257a as a communication cutoff unit that reliably cuts off the communicated state of the channels. The O-rings 257a and 257b are elastic members that deform while generating an elastic force upon being pressed. Other configurations are the same as those of the seventh embodiment, and like reference letters or numerals refer to like constituent elements.

The injection needle 255 uses the drive source for the discharge of the medical fluid to project from the casing 202, and injects the medical fluid to the desired region in the subject. Specifically, the injection needle 255 has a channel 255a formed therein for connecting a distal end side (a side forming a sharp point) for puncturing the subject and a proximal end. The injection needle 255 is provided so as to be inserted slidably in the guide 202b having a cylindrical structure provided at an entrance of the injection needle in the casing 202. The injection needle 255 projects from the casing 202 by an operation of the communication adjusting mechanism 258 for adjusting the channel 255a and the storage chamber 203 in the balloon 204 to the communicated state to start the medical-fluid discharge operation of the balloon 204. On the other hand, the injection needle 255 returns into the casing 202 (that is, is stored in the casing 202) according to the operation of the communication adjusting mechanism 258 for cutting off the communicated state between the channel 255a and the storage chamber 203 to suspend the medical-fluid discharge operation of the balloon 204.

The channel forming unit 256 and the tube 259 are for forming the channel for connecting the channel 255a in the injection needle 255 to the storage chamber 203 in the balloon 204. Specifically, the channel forming unit 256 has the channel 256a formed therein, and is connected to the proximal end of the injection needle 255 so that the channel 256a and the channel 255a communicate with each other. On the other hand, the tube 259 is inserted into a discharge port (opening) of the balloon 204, to form the channel 259a connecting to the storage chamber 203 in the balloon 204. The communicated state between the channel 256a in the channel forming unit 256 and the channel 259a in the tube 259 is adjusted by the communication adjusting mechanism 258.

The communication adjusting mechanism 258 functions so as to perform the communication adjusting operation for adjusting the storage chamber 203 and the channel 256a in the channel forming unit 256 (that is, the channel 255a in the injection needle 255) to the communicated state or the cutoff adjusting operation for adjusting the storage chamber 203 and the channel 256a to the cutoff state, based on the control of the control circuit 213. Further, the communication adjusting mechanism 258 projects the injection needle 255 from the casing 202 synchronously with the communication adjusting operation, and stores the injection needle 255 in the casing 202 synchronously with the cutoff adjusting operation. The communication adjusting mechanism 258 includes a pressing member 258a that presses an open end of the tube 259 to close the opening, a cylinder 258b that forms an internal space connecting the channels 256a and 259a with each other, a holding board 258c that holds the injection needle 255, and the spring 208h and the shape memory members 208j and 208k similar to those of the communication adjusting mechanism 253 in the seventh embodiment.

The pressing member 258a is formed by a soft member or an elastic member such as silicone resin, presses the open end of the tube 259 by the elastic force (pressing force) of the spring 208h, and adheres to the open end. The pressing member 258a closes the channel 259a in the tube 259 due to the adhesion state between the pressing member 258a and the open end of the tube 9. In this case, the communicated state between the channels 256a and 259a, that is, the communicated state between the channel 255a in the injection needle 255 and the storage chamber 203 in the balloon 204 is cut off. The O-ring 257a is provided on the side near the open end of the tube 259 where the pressing member 258a adheres. Since the O-ring 257b and the pressing member 258a adhere to each other, leakage of the medical fluid from the tube 259 into the cylinder 258a is prevented.

On the other hand, when the pressing member 258a decreases the pressing force against the open end of the tube 259 due to the operation of the shape memory members 208j and 208k, the adhesion state thereof to the open end of the tube 259 is released, and the channel 259a in the tube 259 and the channel 256a in the channel forming unit 256 is adjusted to the communicated state. In such a communicated state, the balloon 204 starts the medical-fluid discharge operation. The medical fluid discharged by the balloon 204 sequentially circulates through the channel 259a, the internal space in the cylinder 258b, and the channel 256a and reaches the channel 255a in the injection needle 255, circulates in the channel 255a, and is injected to the outside of the casing (for example, the desired region in the subject).

The cylinder 258b forms the internal space for connecting the channel 256a in the channel forming unit 256 and the channel 259a in the tube 259 with each other, and accommodates the proximal end area of the injection needle 255, the channel forming unit 256, and the pressing member 258a in the internal space. In this case, the cylinder 258b slidably supports the proximal end area of the injection needle 255. When the adhesion state between the pressing member 258a and the open end of the tube 259 is released, the cylinder 258b connects the channel 256a in the channel forming unit 256 and the channel 29a in the tube 259 with each other via the internal space.

The channel forming unit 256 accommodated in the internal space of the cylinder 258b is provided at the proximal end of the injection needle 255, and the proximal end of the injection needle 255 where the channel forming unit 256 is provided is slidably inserted into the opening of the cylinder 258b. On the other hand, the pressing member 258a is provided on an external wall of the channel forming unit 256 and opposite to the tube 259. The O-ring 257a is provided in the proximal end area of the injection needle 255 and on the external wall of the channel forming unit 256. The O-ring 257a has an inner diameter larger than the diameter of the opening of the cylinder 258b for inserting the injection needle 255, and when the injection needle 255 projects from the casing 202, the O-ring 257a adheres to near the opening of the cylinder 258b.

The holding board 258c holds the injection needle 255, and projects the injection needle 255 to the outside of the casing 202, synchronously with the communication adjusting operation, and returns (stores) the injection needle 255 in the casing 202 synchronously with the cutoff adjusting operation. Specifically, the holding board 258c is fixed to the side of the injection needle 255 (for example, to the distal end side rather than the proximal end area of the injection needle 255), and the spring 208h and the shape memory members 208j and 208k are connected thereto. In this case, the spring 208h is fixed to the holding board 258c at one end and to the guide 202a at the other end. Each of the shape memory members 208j and 208k is fixed to the holding board 258c at one end and to the inner wall of the casing 202 at the other end. The holding board 258c projects the injection needle 255 toward the outside of the casing 202 due to the operation of the shape memory members 208j and 208k, and releases the adhesion state between the pressing member 158a and the open end of the tube 259 to adjust the channel 255a in the injection needle 255 and the storage chamber 203 to the communicated state. In this case, the balloon 204 discharges the medical fluid in the storage chamber 203. On the other hand, the holding board 258c stores the injection needle 255 in the casing 202 due to the operation of the spring 208h, and presses the pressing member 258a to the open end of the tube 259 so that the pressing member 258 adheres to the open end of the tube 259, thereby adjusting the channel 255a in the injection needle 255 and the storage chamber 203 to the cutoff state. In this case, the balloon 204 suspends the medical-fluid discharge operation.

In the body-insertable apparatus 250a having such a configuration, the control circuit 213 controls expansion and contraction of the shape memory members 208j and 208k.

Figure 32:
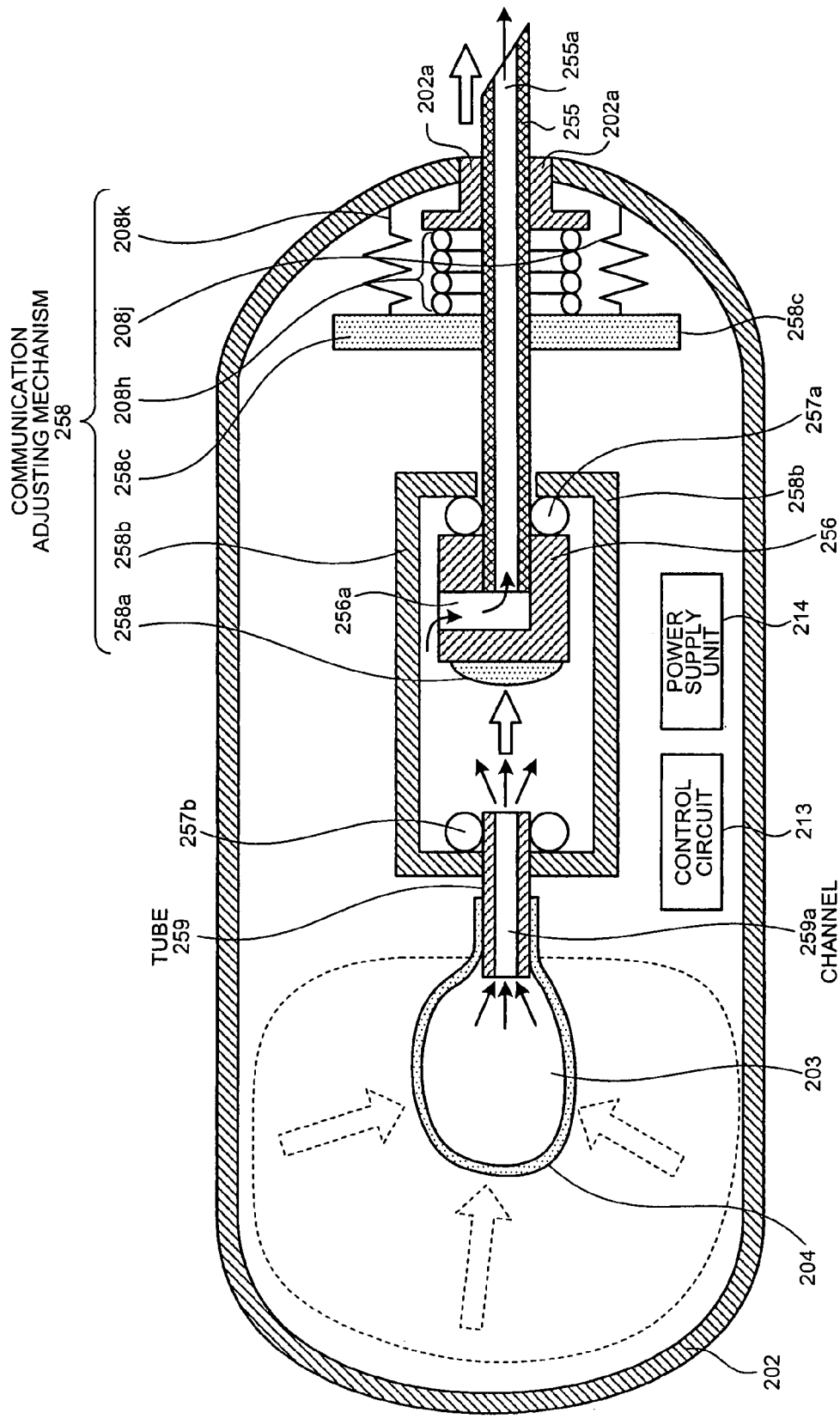
FIG. 32 is a schematic sectional view schematically exemplifying a state where the injection needle of the body-insertable apparatus, which is the modification of the seventh embodiment, is projected.

An operation of the body-insertable apparatus 250a is explained next. FIG. 32 is a schematic sectional view schematically exemplifying a state where the injection needle 255 of the body-insertable apparatus 250a is projected. The projection operation of the injection needle 255 and the medical-fluid discharge operation are explained with reference to FIG. 32.

The control circuit 213 controls the drive of the communication adjusting mechanism 258 so that the balloon 204 starts the medical-fluid discharge operation. Specifically, the control circuit 213 supplies predetermined current to the shape memory members 208j and 208k, which are the drive source of the communication adjusting mechanism 258, to control the shape change thereof (contraction deformation). The shape memory members 208j and 208k generate a driving force due to the shape change, and pull the holding member 258c using the driving force. In this case, the holding member 258c projects the injection needle 255 toward the outside of the casing 202 and moves the pressing member 258a in a direction away from the open end of the tube 259 due to the driving force of the shape memory members 208j and 208k. The pressing member 258a moves together with the injection needle 255 and the channel forming unit 256, to release the adhesion state thereof to the open end of the tube 259.

Substantially simultaneously, the holding board 258c presses the O-ring 257a against near the opening of the cylinder 258b (that is, the opening where the injection needle 255 is inserted). In this case, the O-ring 257a moves together with the injection needle 255 and the channel forming unit 256, and is pressed against near the opening of the cylinder 258*b* by the channel forming unit 256 and put between the channel forming unit 256 and the cylinder 258*b*. The O-ring 257*a* in this state prevents the medical fluid from leaking from the opening of the cylinder 258*b* to the inside of the casing 202.

On the other hand, the channel 256*a* in the channel forming unit 256 and the channel 259*a* in the tube 259 are adjusted to the communicated state via the internal space of the cylinder 258*b* upon release of the adhesion state between the pressing member 258*a* and the open end of the tube 259. In this case, the channel 255*a* in the injection needle 255 and the storage chamber 203 are adjusted to the communicated state, and the balloon 204 starts to discharge the medical fluid stored in the storage chamber 203.

The communication adjusting mechanism 258 having such a configuration functions as the discharge starting unit that performs the communication adjusting operation for starting the medical-fluid discharge operation of the balloon 204 and the projection operation of the injection needle 255 synchronously, using the driving force generated by the shape memory members 208*j* and 208*k*. When the channel 255*a* in the injection needle 255 and the storage chamber 203 are adjusted to the communicated state according to the communication adjusting operation of the communication adjusting mechanism 258, the medical fluid in the storage chamber 203 circulates through the channel 259*a* in the tube 259, the internal space of the cylinder 258*b*, the channel 256*a* in the channel forming unit 256, and the channel 255*a* in the injection needle 255 sequentially, and is discharged from the distal end of the injection needle 255. The injection needle 255 projected upon start of the medical-fluid discharge operation injects the medical fluid to the desired region in the subject such as the affected part. In this case, the balloon 204 can inject a desired amount of medical fluid to the desired region in the subject via the injection needle 255 by using its contraction force to perform the medical-fluid discharge operation.

Thereafter, when the control circuit 213 stops current supply to the shape memory members 208*j* and 208*k*, the shape memory members 208*j* and 208*k* stop the contraction deformation and lose the driving force. In this case, the holding board 258*c* uses the elastic force of the spring 208*h* to pull the injection needle 255 back into the casing 202, and presses the pressing member 258*d* against the open end of the tube 259. In this case, the injection needle 255 is stored in the casing 202, the pressing member 258*a* adheres to the open end of the tube 259, and the channels 256*a* and 259*b* are adjusted to the cutoff state due to the adhesion state between the pressing member 258*d* and the open end of the tube 259.

If the balloon 204 has not discharged the medical fluid in an amount equal to or more than the predetermined amount, when the channels 256*a* and 259*b* are adjusted to the cutoff state, the balloon 204 stops (suspends) the medical-fluid discharge operation. Thereafter, when the pressing member 258*a* moves away from the open end of the tube 259 again and projects the injection needle 255, the channels 256*a* and 259*b* are again adjusted to the communicated state, and the balloon 204 resumes the medical-fluid discharge operation. Thus, since the communication adjusting mechanism 258 repeats the communication adjusting operation and the cutoff adjusting operation, the balloon 204 can intermittently repeat the medical-fluid discharge operation until the desired amount of medical fluid has been discharged.

The body-insertable apparatus 250*a* adopting such a configuration has substantially the same function as that of the body-insertable apparatus 250 according to the seventh embodiment, and hence the body-insertable apparatus 250*a* can obtain the operations and effects of the body-insertable apparatus 250.

In the modification of the seventh embodiment, a channel folded back via the sheet member 208*b* (folded channel) is not formed as exemplified by the channels 254*a* and 254*b* formed in the sheet holder 253*a*, but a channel for connecting the storage chamber 203 of the medical fluid to the channel 255*a* in the injection needle 255 is formed. Accordingly, the channel for circulating the medical fluid from the storage chamber 203 of the medical fluid to the channel 255*a* in the injection needle 255 can be easily formed, as compared to an instance in which such a folded channel is formed.

Eighth Embodiment

An eighth embodiment of the present invention is explained next. In the eighth embodiment, a part of the tube for connecting the storage chamber that stores the medical fluid to the channel in the injection needle is pressed to adjust to the cutoff state, and the injection needle is projected from the casing synchronously with the operation for releasing the cutoff state (that is, operation for starting the medical-fluid discharge operation).

Figure 33:
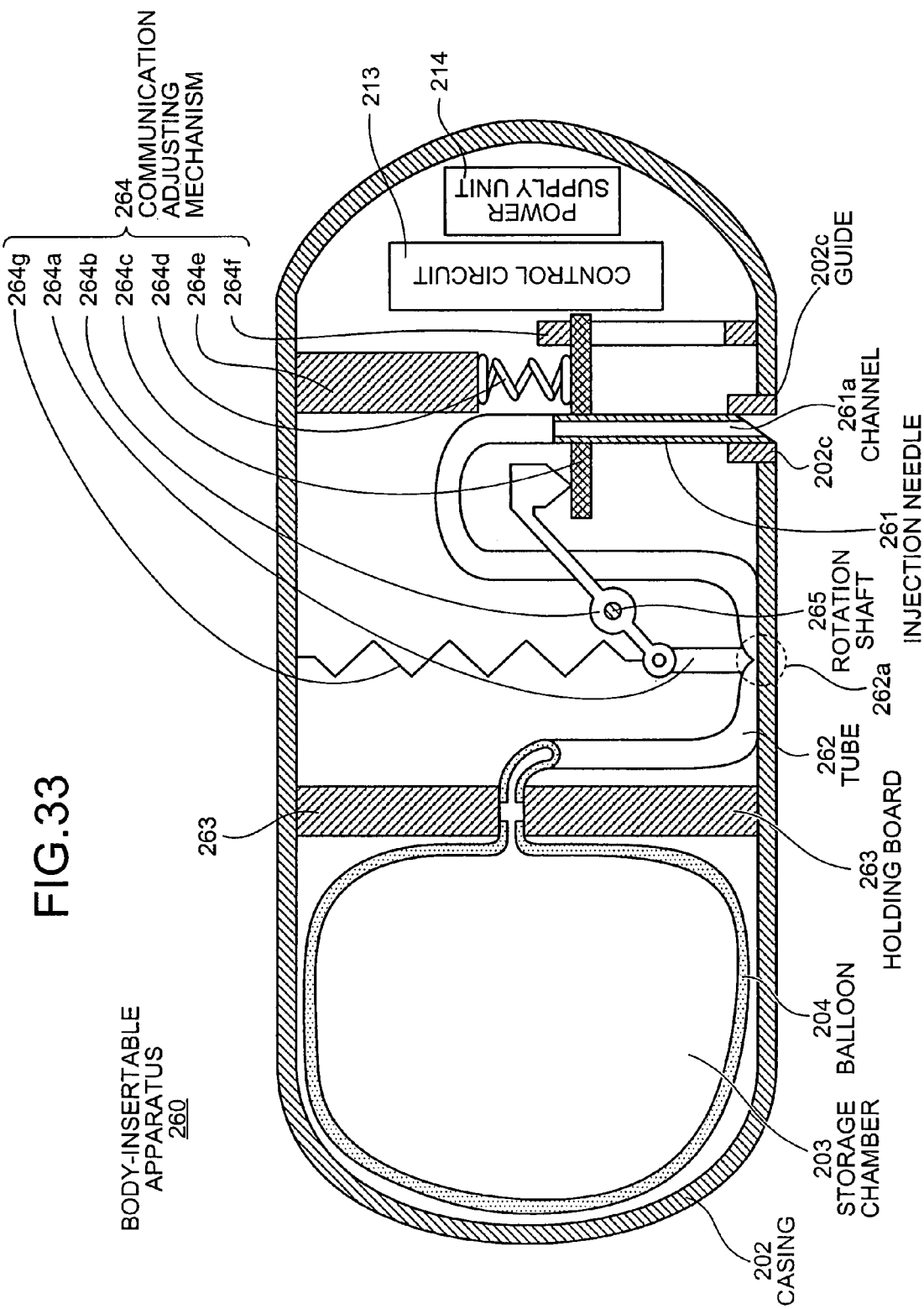
FIG. 33 is a schematic sectional view schematically showing one configuration example of a body-insertable apparatus according to an eighth embodiment of the present invention.

FIG. 33 is a schematic sectional view schematically showing one configuration example of the body-insertable apparatus according to the eighth embodiment of the present invention. As shown in FIG. 33, a body-insertable apparatus 260 includes, in the casing 202, the balloon 204 as the medical-fluid discharger that forms the storage chamber 203, an injection needle 261 for injecting the medical fluid to the desired region in the subject, a tube 262 for circulating the medical fluid in the storage chamber 203 to the injection needle 261, and a holding board 263 that holds the balloon 204 and the tube 262 so as to communicate with each other. The body-insertable apparatus 260 further includes, in the casing 202, a communication adjusting mechanism 264 that adjusts the tube 262 in a communicated state and projects the injection needle 261 from the casing 202, the control circuit 213 that controls the driving state of the communication adjusting mechanism 264, and the power supply unit 214 that supplies driving power to the control circuit 213.

The injection needle 261 projects from the casing 202 by using the drive source for the discharge of the medical fluid to inject the medical fluid to the desired region in the subject. Specifically, the injection needle 261 has a channel 261*a* formed therein for connecting a distal end side (a side forming a sharp point) for puncturing the subject and a rear end. In the injection needle 261, the distal end side is slidably inserted in a guide 202*c* of the casing 202, and the rear end is fixed to the communication adjusting mechanism 264. The guide 202*c* has a cylindrical structure, and provided at an entrance of the injection needle in the casing 202. The guide 202*c* regulates the moving direction of the injection needle 261 so as to be able to project or store the injection needle 261 smoothly.

The tube 262 forms the medical fluid channel that circulates the medical fluid in the storage chamber 203 to the channel 261*a* of the injection needle 261. Specifically, the tube 262 is connected to the holding board 263 with one end thereof communicating with the storage chamber 203, and also connected to the injection needle 261 with the other end communicating with the channel 261*a*. As shown in FIG. 33, a part of the tube 262 is fixed to the casing 202. The tube 262 includes a variable area 262*a* that can be easily squashed by applying predetermined pressing force to the part thereof. In the tube 262, the circulation of the medical fluid between the storage chamber 203 and the channel 261*a* is cut off (cutoff state) due to the variable area 262a being squashed. Further, the tube 262 connects the storage chamber 203 to the channel 261a (communicated state) by decreasing the pressing force applied to the variable area 262a to release the cutoff state.

The communication adjusting mechanism 264 functions so as to perform the communication adjusting operation for adjusting the tube 262 to the communicated state or the cutoff adjusting operation for adjusting the tube 262 to the cutoff state based on the control of the control circuit 213. The communication adjusting mechanism 264 projects the injection needle 261 from the casing synchronously with the communication adjusting operation, and stores the injection needle 261 in the casing 202 synchronously with the cutoff adjusting operation. The communication adjusting mechanism 264 includes a pressing member 264a that applies predetermined pressing force to the variable area 262a of the tube 262, a associating member 264b that associates the movement of the pressing member 264a with the movement of the injection needle 261, and a holding board 264c that holds the injection needle 261. The communication adjusting mechanism 264 further includes a spring 264f that generates the pressing force applied by the pressing member 264a, a spring board 264e that holds the spring 264d, a guide 264f that regulates the moving direction of the holding board 264c, and a shape memory member 264g that changes the position of the pressing member 264a relative to the variable area 262a.

The pressing member 264a applies the pressing force generated by the spring 264d to the variable area 262a of the tube 262 to adjust the tube 262 to the cutoff state. Specifically, the end of the pressing member 264a is rotatably fitted to the associating member 264b, and the pressing member 264a applies the elastic force, that is, the pressing force of the spring 264d transmitted by the associating member 264b to the variable area 262a.

The associating member 264b associates the movement of the pressing member 264a with the movement of the injection needle 261. Specifically, the pressing member 264a is rotatably provided at one end of the associating member 264b, and the holding board 64 is pressed against the other end of the associating member 264b. A rotation shaft 265 is provided at a predetermined position between the opposite ends thereof, and the associating member 264b rotates centering on the rotation shaft 265. The rotation shaft 265 is provided at a position near the end of the pressing member 264a side rather than the end of the holding board 264c side. By providing the rotation shaft 265 in this manner, the associating member 264b moves the pressing member 264a away from the variable area 262a, and can give a shift sufficient for projecting the injection needle 261 from the casing 202, to the holding board 264c.

The holding board 264c holds the injection needle 261 in a manner penetrated by the injection needle 261, and moves the injection needle 261 synchronously with the movement of the pressing member 264a. Specifically, the holding board 264c is supported by the end of the associating member 264b and the spring 264d, and one end of the holding board 264c is slidably inserted into a through hole in the guide 264f. The holding board 264c is pushed in a direction approaching the guide 202c due to the rotation of the associating member 264b, thereby projecting the injection needle 261 from the casing 202. The holding board 264c is pulled in a direction away from the guide 202c due to the elastic force of the spring 264d, thereby storing the injection needle 261 in the casing 202. The holding board 264c moves along the through hole in the guide 264f.

The spring 264d generates the pressing force to be applied to the variable area 262a by the pressing member 264a and the driving force for the storage operation for storing the injection needle 261. Specifically, one end of the spring 264d is connected to the holding board 264c, and the other end is fixed to the spring board 264e, with the spring length being maintained longer than a natural length. The thus arranged spring 264d functions so as to energize the elastic force (contraction force) in a direction of moving the holding board 264c away from the guide 202c. In this case, the elastic force of the spring 264d is transmitted to the pressing member 264a as the pressing force by the associating member 264b, and transmitted to the holding board 264c as the driving force for the contraction operation of the injection needle 261.

The spring board 264e holds the spring 264d. Specifically, the spring board 264e is fixed to the casing 202, and one end of the spring 264d is fixed thereto, and thus, the spring 264d is held by the spring board 264e. The guide 264f is a frame member in which the through hole, into which the holding board 264c can be slidably inserted, is formed and regulates the moving direction of the holding board 264c. The holding board 264c can reliably perform the projection operation or the storage operation of the injection needle 261 since the moving direction thereof is regulated by the guide 264f.

The shape memory member 264g is a drive source of the communication adjusting mechanism 264 that synchronously performs the communication adjusting operation of the tube 262 and the projection operation of the injection needle 261, and generates a driving force for performing the projection operation and the communication adjusting operation of the injection needle 261 synchronously. Specifically, the shape memory member 264g has substantially the same function and structure as those of the shape memory members 208j and 208k in the sixth embodiment. The shape memory member 264g is fixed to the end of the pressing member 264a of the associating member 264b at one end, and to the casing 202 at the other end, and has a length sufficient for the pressing member 264a to squash the variable area 262a of the tube 262 under a temperature condition, for example, same as the temperature in the subject. On the other hand, the shape memory member 264g changes its shape at a predetermined temperature, for example, under a temperature condition sufficiently higher than the temperature in the subject, to generate a predetermined driving force with the shape change (specifically, contraction deformation). The driving force is a physical force stronger than the elastic force of the spring 264d, and sufficient for the associating member 264a to move the holding board 264c away from the variable area 262a and push the holding board 264c so as to inject the injection needle 261.

When the pressing member 264a moves away from the variable area 262a, the balloon 204 and the injection needle 261 are adjusted to the communicated state via the tube 262. In this case, the balloon 204 discharges the medical fluid to the outside of the casing 202 (for example, to a desired region in the subject) via the tube 262 and the channel 261a of the injection needle 261. Therefore, the driving force generated by the shape memory member 264g is used for performing the projection operation of the injection needle 261, and for the communication adjusting operation for starting the medical-fluid discharge operation by the balloon 204 (that is, an example of the physical force for the discharge the medical fluid). The shape memory member 264g that generates the physical force for the discharge the medical fluid is a driving force for the discharge the medical fluid.

In the body-insertable apparatus 260 according to the eighth embodiment, the control circuit 213 functions so as to control the shape change of the shape memory member 264g according to the presence of the current supply to the shape memory member 264g, and control the projection operation of the injection needle 261 and the medical-fluid discharge operation by the balloon 204 through the control of the shape change, substantially in the same manner as the shape memory members 208j and 208k.

Figure 34:
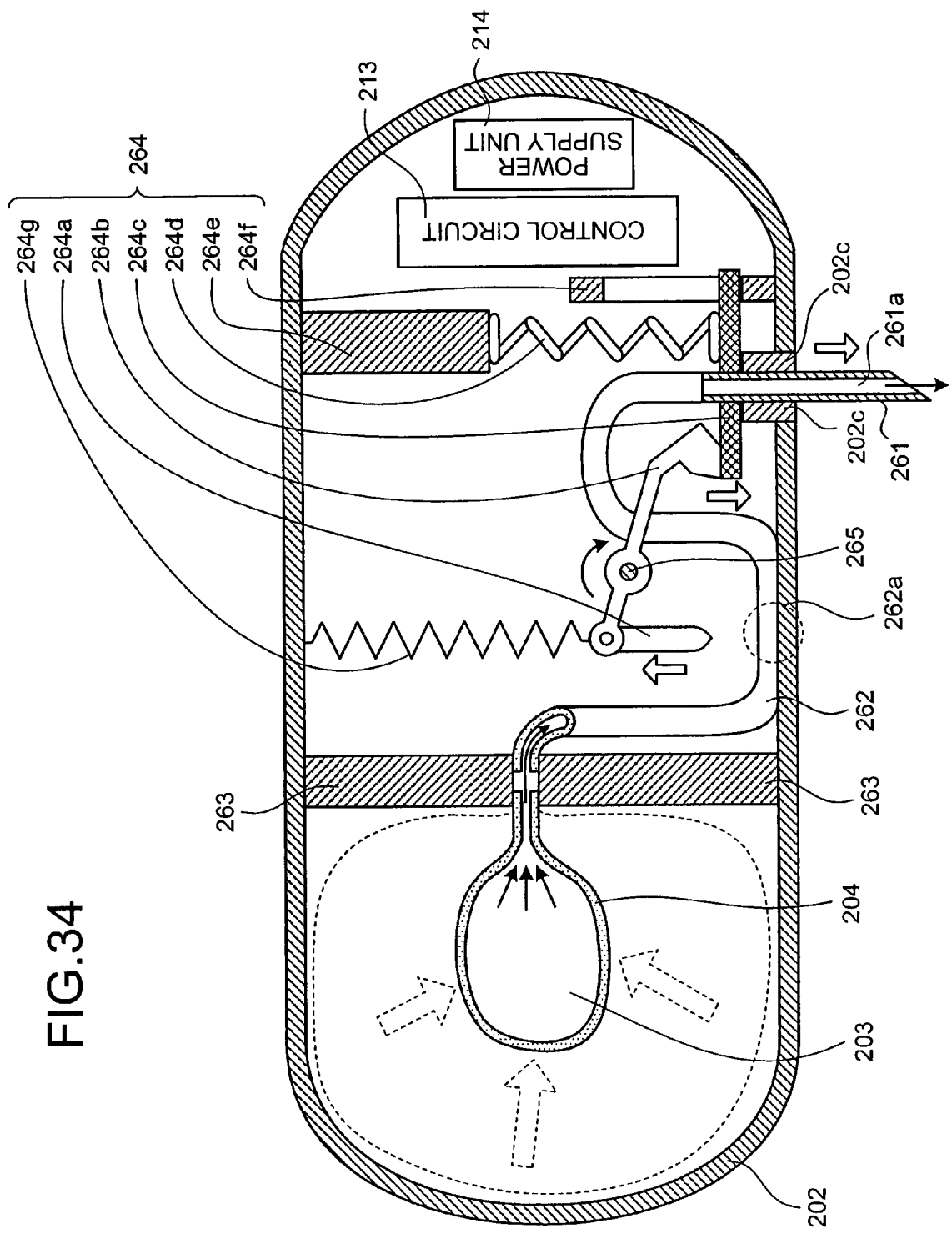
FIG. 34 is a schematic sectional view schematically exemplifying a state where the injection needle of the body-insertable apparatus according to the eighth embodiment is projected.

An operation of the body-insertable apparatus 260 is explained next. FIG. 34 is a schematic showing sectional view schematically exemplifying the projected state of the injection needle 261 of the body-insertable apparatus 260. The projection operation of the injection needle 261 and the medical-fluid discharge operation are explained with reference to FIG. 34.

The control circuit 213 performs driving control of the communication adjusting mechanism 264 so that the balloon 204 starts the medical-fluid discharge operation. Specifically, the control circuit 213 supplies the predetermined current to the shape memory member 264g, which is the drive source for the communication adjusting mechanism 264, to change the shape (contraction deformation). The shape memory member 264g generates the predetermined driving force by the shape change, and pulls the end of the associating member 264b on the pressing member 264a side by using the driving force. In this case, the pressing member 264a moves in a direction away from the variable area 262a of the tube 262 by the driving force to decrease the pressing force against the variable area 262a. As a result, the pressing member 264a adjusts the tube 262 to the communicated state and the balloon 204 starts the medical-fluid discharge operation.

The associating member 264b moves the pressing member 264a away from the variable area 262a due to an operation of the shape memory member 264g, and pushes the holding board 264c in a direction approaching the guide 202c. The holding board 264c projects the injection needle 261 from the casing 202 synchronously with the communication adjusting operation of the tube 262, due to the operation of the associating member 264b.

In the state where the injection needle 261 projects in this manner, the storage chamber 203 and the channel 261a of the injection needle 261 communicates with each other via the tube 262, and the balloon 204 continues the medical-fluid discharge operation. According to the medical-fluid discharge operation, the medical fluid in the storage chamber 203 is discharged from the distal end of the injection needle 261, sequentially passing through the tube 262 and the channel 261a.

The communication adjusting mechanism 264 having such a configuration functions as the discharge starting unit that synchronously performs the projection operation of the injection needle 261 and the communication adjusting operation of the tube 262 by using the driving force generated by the shape memory member 264g, to project the injection needle 261 from the casing 202 and start the medical-fluid discharge operation of the balloon 204. The injection needle 261 punctures a desired region in the subject such as the affected part, and the balloon 204 can inject a desired amount of medical fluid to the desired region in the subject via the injection needle 261 by using its contraction force to perform the medical-fluid discharge operation.

Thereafter, when the control circuit 213 stops the current supply to the shape memory member 264g, the shape memory member 264g stops the contraction deformation and loses the driving force. In this case, the holding board 264c moves in the direction away from the guide 202c due to the elastic force of the spring 264d, and stores the injection needle 261 in the casing 202. At the same time, the holding board 264c pushes the end of the associating member 264b by the elastic force of the spring 264b. The associating member 264b rotates due to the operation of the holding board 264c, and moves the pressing member 264a in a direction approaching the variable area 262a of the tube 262. The pressing member 264a applies the elastic force of the spring 264d transmitted by the associating member 264b as the pressing force to the variable area 262a again, to squash the variable area 262a. As a result, the tube 262 is adjusted again to the cutoff state.

If the balloon 204 has not discharged the medical fluid in an amount equal to or more than the predetermined amount, when the tube 262 is adjusted to the cutoff state, the balloon 204 stops (suspends) the medical-fluid discharge operation. Thereafter, when the pressing member 264a moves away from the variable area 262a again, the tube 262 is re-adjusted to the communicated state, so that the balloon 204 resumes the medical-fluid discharge operation. Since the communication adjusting mechanism 264 repeats the communication adjusting operation and the cutoff adjusting operation in this manner, the balloon 204 can intermittently repeat the medical-fluid discharge operation until the desired amount of medical fluid has been discharged.

The body-insertable apparatus 260 adopting such a configuration has substantially the same function as that of the body-insertable apparatus 201 according to the sixth embodiment, and the communication adjusting mechanism that starts the medical-fluid discharge operation synchronously with the projection operation of the injection needle can be simplified. Therefore, the body-insertable apparatus 260 can obtain the same operations and effects as those of the body-insertable apparatus 201, thereby promoting space saving inside the casing 202, and downsizing of the apparatus.

Ninth Embodiment

A ninth embodiment of the present invention is explained. In the ninth embodiment, a piston mechanism that performs the medical-fluid discharge operation is provided, and driving energy of the piston mechanism is chemically generated to start the medical-fluid discharge operation, while projecting the injection needle.

Figure 35:
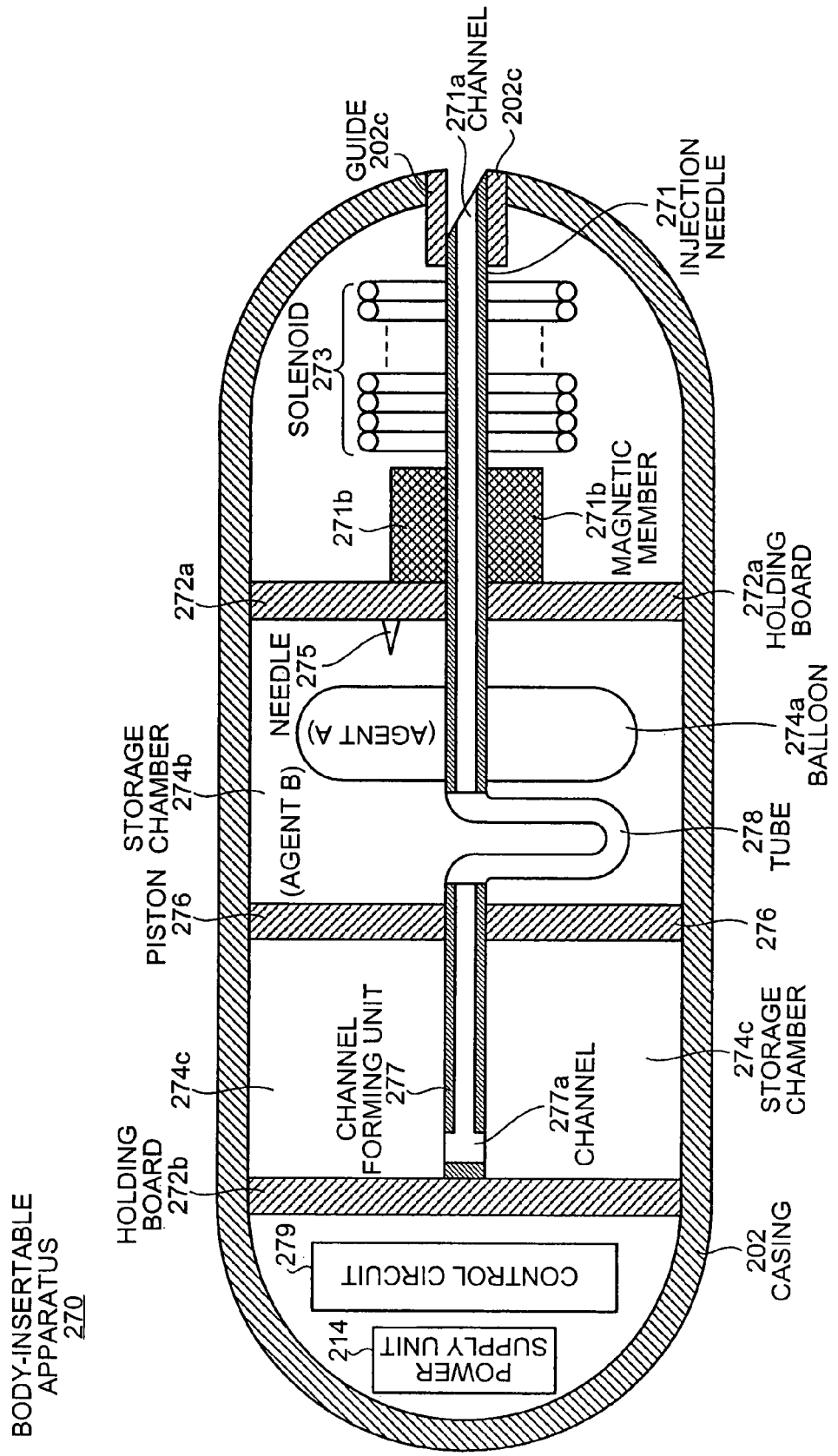
FIG. 35 is a schematic sectional view schematically showing one configuration example of a body-insertable apparatus according to a ninth embodiment of the present invention.

FIG. 35 is a schematic sectional view schematically showing one configuration example of the body-insertable apparatus according to the ninth embodiment of the present invention. As shown in FIG. 35, a body-insertable apparatus 270 includes, in the casing 202, an injection needle 271 for injecting the medical fluid to the desired region in the subject, a holding board 272a that slidably holds the injection needle 271, a solenoid 273 for generating a magnetic field near the injection needle 271, and a magnetic member 271b that projects the injection needle 271 from the casing 202 by the magnetic field. The body-insertable apparatus 270 also includes, in the casing 202, a balloon 274a and a storage chamber 274b for respectively storing agents A and B for generating the driving energy for the medical fluid discharging operation, and a needle 275 that bursts the balloon 274a upon projection of the injection needle 271. The body-insertable apparatus 270 also includes, in the casing 202, a storage chamber 274c that pre-stores the medical fluid, a piston 276 for discharging the medical fluid by compressing the storage chamber 274c, a channel forming unit 277 that forms a channel for circulating the medical fluid, a holding board 272b that holds the channel forming unit 277, a tube 278 that connects the channel forming unit 277 and the injection needle 271, a control circuit 279 that controls generation of the magnetic field by the solenoid 273, and a power supply unit 214 that supplies driving power to the control circuit 279.

The injection needle 271 projects from the casing 202 by using the drive source for the discharge of the medical fluid to inject the medical fluid to the desired region in the subject. Specifically, the injection needle 271 has a channel 271*a* formed therein for connecting a distal end side (a side forming a sharp point) for puncturing the subject and a rear end side with each other. The injection needle 271 is arranged so that the distal portion is positioned in the guide 202*c*. The guide 202*c* is a member having a cylindrical structure, and is provided at the entrance of the injection needle 271 in the casing 202. The guide 202*c* regulates the moving direction of the injection needle 271 so that the injection needle 271 can be smoothly projected or stored.

The holding board 272*a* slidably holds the injection needle 271. Specifically, the holding board 272*a* is fixed to the casing 202, and slidably holds the injection needle 271, in a manner penetrated by the injection needle 271.

The magnetic member 271*b* functions as a projecting unit that projects the injection needle 271 from the casing 202 by the magnetic field generated by the solenoid 273. Specifically, the magnetic member 271*b* is realized by using a ferromagnet such as iron, nickel, or cobalt, or a magnet, and fixed in such a manner that the magnetic member 271*b* is penetrated by the injection needle 271. The magnetic member 271*b* is provided so as to be positioned between the holding board 272*a* and the guide 202*c*, and projects the injection needle from the casing 202 or stores the injection needle 271 in the casing 202 by moving between the holding member 272*a* and the guide 202*c* due to the magnetic field generated by the solenoid 273.

The solenoid 273 generates the magnetic field near the injection needle 271 based on the control of the control circuit 279, and functions as the drive source for the magnetic member 271*b* that projects the injection needle 271. Specifically, the solenoid 273 has a coil diameter capable of inserting the injection needle 271 and the magnetic member 271*b* inside thereof, and is arranged near the guide 202*c*. The solenoid 273 generates a magnetic field for attracting the magnetic member 271*b* toward the guide 202*c* (magnetic field in a projecting direction) or a magnetic field for keeping the magnetic member 271*b* away from the guide 202*c* (magnetic field in a storing direction). The winding number of the solenoid 273 needs only to be sufficient for generating the magnetic field having strength sufficient for moving the injection needle 271 and the magnetic member 271*b*.

The balloon 274*a* stores therein the agent A of the agents A and B for chemically generating the driving energy for sliding the piston 276. The balloon 274*a* is arranged at a position on the injection needle 271 opposite to the magnetic member 271*b*, designating the holding board 272*a* as a boundary. In this case, the balloon 274*a* is arranged so as to come in contact with the holding board 272*a* when the injection needle 271 projects from the casing 202.

The needle 275 bursts the balloon 274*a* upon projection of the injection needle 271. Specifically, the needle 275 is provided in an area on the holding board 272*a* with which the balloon 274*a* comes in contact when the injection needle 271 projects. The needle 275 bursts the balloon 274*a*, upon projection of the injection needle 271 from the casing 202.

The needle 275 can be provided at the rear end of the injection needle 271 instead of the balloon 274*a*. In this case, the balloon 274*a* is provided on the holding board 272*a* so that it is burst by the needle 275 with projection of the injection needle 271.

The storage chamber 274*b* pre-stores the agent B. Specifically, the storage chamber 274*b* is formed in an area surrounded by the holding board 272*a*, the piston 276, and a part of the casing 202 (that is, a part positioned between the holding board 272*a* and the piston 276). The agent B stored in the storage chamber 274*b* is mixed with the agent A upon burst of the balloon 274*a*. The agents A and B mixed in this manner foam due to a predetermined chemical reaction to increase the pressure in the storage chamber 274*b*, thereby generating dynamic energy to be applied to the piston 276.

The storage chamber 274*c* pre-stores the medical fluid to be injected to the desired region in the subject. Specifically, the storage chamber 274*c* is formed in an area surrounded by the holding board 272*b*, the piston 276, and a part of the casing 202 (that is, a part positioned between the holding board 272*b* and the piston 276).

The piston 276 compresses the storage chamber 274*c* that pre-stores the medical fluid to discharge the medical fluid. Specifically, the piston 276 is arranged between the holding boards 272*a* and 272*b* so as to separate the storage chambers 274*b* and 274*c*. The piston 276 is slidably penetrated by the channel forming unit 277. The piston 276 slides toward the holding board 272*b* due to the dynamic energy chemically generated by mixing the agents A and B, compresses the storage chamber 274*c*, and pressurizes the medical fluid.

The channel forming unit 277 circulates the medical fluid pressurized by the piston 276. Specifically, the channel forming unit 277 has a channel 277*a* connecting to the storage chamber 274*c* formed therein. The channel forming unit 277 is fixed to the holding board 272*b* at one end opening to the storage chamber 274*c*, and the other end thereof penetrates the piston 276. An opening of the channel 277*a* is formed at the other end of the channel forming unit 277. The holding board 272*b* is provided near the end of the casing 202 opposite to the holding board 272*a*, designating the piston 276 as a boundary.

The tube 278 is a soft tube member having flexibility, and one end thereof is connected to the opening of the channel 277*a*, and the other end is connected to an opening of the channel 271*a* in the injection needle 271. The tube 278 connects the storage chamber 274*c* and the channel 271*a* with each other via the channel 277*a*. In this case, the channel forming unit 277 can circulate the medical fluid pressurized by the piston 276 to the channel 271*a* in the injection needle 271 via the tube 278.

The holding boards 272*a*, 272*b*, the piston 276, and a part of the casing 202 (that is, a part positioned between the holding boards 272*a* and 272*b*) form a piston mechanism of the body-insertable apparatus 270. The channel forming unit 277 and the tube 278 form a medical fluid channel for circulating the medical fluid to the channel 271*a* in the injection needle 271. The piston mechanism discharges the medical fluid by compressing the storage chamber 274*c* due to the dynamic energy chemically generated by mixing the agents A and B. The medical fluid is circulated to the channel 271*a* via the medical fluid channel, that is, the channel 277*a* and the tube 278. The balloon 274*a* and the needle 275 function as an energy generator that chemically generates the dynamic energy by mixing the agents A and B. The driving force generated by the solenoid 273 moves the injection needle 271 together with the magnetic member 271*b*, and is also used for generating the dynamic energy (driving energy used for the medical-fluid discharge operation) by mixing the agents A and B. Therefore, the driving force generated by the solenoid 273 is an example of the physical force for the discharge of the medical fluid. The solenoid 273 that generates the physical force for the discharge of the medical fluid is the drive source for the discharge of the medical fluid.

The control circuit 279 functions so as to supply the current to the solenoid 273 to perform control for generating the magnetic field for driving the magnetic member 271*b*, and to control the projection operation of the injection needle 271 and the medical-fluid discharge operation through the control for generating the magnetic field. Specifically, the control circuit 279 functions to supply forward current to the solenoid 273 when the body-insertable apparatus 270 introduced in the subject reaches the desired region in the subject. Since the forward current flows to the solenoid 273, a magnetic field in the projecting direction is generated near the magnetic member 271b and the magnetic member 271b is attracted to the guide 202c. The magnetic member 271b projects the injection needle 271 from the casing 202. Upon the drive of the magnetic member, the balloon 274a comes in contact with the needle 275 to burst, thereby mixing the agents A and B, and the dynamic energy for driving the piston 276 is generated. The medical-fluid discharge operation is started by the dynamic energy. On the other hand, the control circuit 279 generates a magnetic field in the storing direction by supplying reverse current to the solenoid 273. The magnetic member 271b drives in the direction away from the guide 202c due to the magnetic field in the storing direction, thereby storing the injection needle 271 in the casing 202.

As the configuration for specifying the current supply timing by the control circuit 279, for example, a timer mechanism can be provided, or a radio reception mechanism is incorporated therein and a control signal can be supplied from the outside, as in the control circuit 213.

Figure 37:
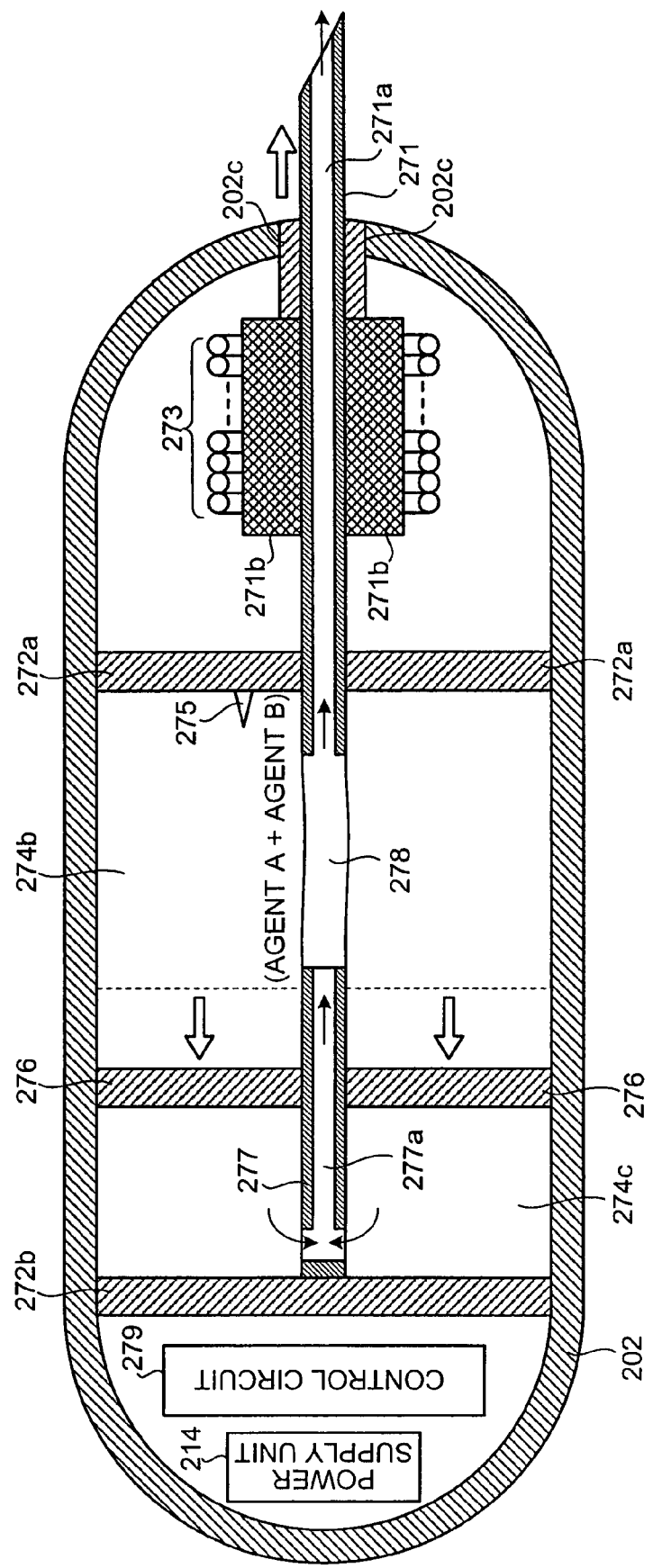
FIG. 37 is a schematic sectional view schematically exemplifying a state where the injection needle of the body-insertable apparatus according to the ninth embodiment is projected.

An operation of the body-insertable apparatus 270 is explained next. FIG. 36 is a schematic diagram schematically exemplifying a state where the injection needle 271 is projected, and agents A and B are mixed, to chemically generate the dynamic energy. FIG. 37 is a schematic sectional view schematically exemplifying a state where the injection needle 271 of the body-insertable apparatus 270 is projected. The projection operation of the injection needle 271 and the medical-fluid discharge operation are explained with reference to FIGS. 36 and 37.

The control circuit 279 supplies the forward current to the solenoid 273, to generate the magnetic field in the projecting direction near the magnetic member 271b. The magnetic member 271b moves in the direction approaching the guide 202c due to the magnetic field in the projecting direction, and slides the injection needle 271 in the projecting direction. In this case, as shown in FIG. 36, the balloon 274a moves with the slide of the injection needle 271, and comes in contact with the needle 275 upon projection of the injection needle 271 from the casing. The needle 275 bursts the balloon 274a to mix the agent A in the balloon 274a with the agent B in the storage chamber 274b. The thus mixed agents A and B foam due to the chemical reaction, and increase the pressure in the storage chamber 274b. In this case, the dynamic energy generated by the chemical reaction is applied to the piston 276 as the pressing force for pressing the piston 276.

The piston 276 slides in the direction approaching the holding board 272b by the generated dynamic energy, that is, the pressing force, and compresses the storage chamber 274c and pressurizes the medical fluid. The medical fluid sequentially circulates in the channel 277a, the tube 278, and the channel 271a, and is discharged from the distal end of the projected injection needle 271. The medical-fluid discharge operation is started in this manner. Thereafter, the piston 276 continuously compresses the storage chamber 274c until the medical fluid in an amount equal to or more than the desired amount has been discharged by the dynamic energy. Accordingly, the projected injection needle 271 punctures the desired region in the subject such as the affected part, to inject the desired amount of medical fluid discharged by the operation of the piston 276 to the desired region.

Thereafter, the control circuit 279 supplies the reverse current to the solenoid 273 to generate the magnetic field in the storing direction. The magnetic member 271b drives in the direction away from the guide 202c due to the magnetic field in the storing direction, and pulls the injection needle 271 back into the casing 202. The injection needle 271 is stored in the casing 202 by the operation of the magnetic member 271b.

The body-insertable apparatus 270 adopting such a configuration generates the magnetic field in the projecting direction by supplying the current to the solenoid 273, projects the injection needle 271 due to the magnetic field in the projecting direction, and applies the dynamic energy to the piston 276 so that the medical-fluid discharge operation can be started. Therefore, the body-insertable apparatus 270 can perform the projection operation of the injection needle and the medical-fluid discharge operation simultaneously by supplying the predetermined current to the solenoid 273, and hence the projection operation of the injection needle can be executed in a power saving manner, without consuming additional driving power for executing the projection operation of the injection needle.

Further, the energy generator is formed by forming the projecting unit of the injection needle 271 by the magnetic member 271b directly fixed to the injection needle 271 and the solenoid 273 that generates the magnetic field in the projecting direction, and using the storage chamber 274b that stores the agent B, the balloon 74b and the needle 275 that mix the agents A and B synchronously with the projection operation of the injection needle 271, to generate the driving energy for the piston 276. The body-insertable apparatus 270 adopting such a configuration can simplify the mechanism that performs the projection operation of the injection needle and the medical-fluid discharge operation synchronously, and can downsize the apparatus easily. Further, since the body-insertable apparatus 270 stores the projected injection needle 271 in the casing 202, the injection needle can puncture only a necessary portion in the subject.

Further, the body-insertable apparatus 270 uses the dynamic energy chemically generated by mixing predetermined agents, to perform the medical-fluid discharge operation. As a result, the medical-fluid discharge operation can be executed in a power saving manner, without consuming additional driving power for executing the medical-fluid discharge operation.

Tenth Embodiment

A tenth embodiment of the present invention is explained next. In the tenth embodiment, the piston mechanism that uses the shape memory member as the drive source is provided as the medical-fluid discharger, predetermined thermal energy is transmitted to the shape memory member to start the medical-fluid discharge operation, and the projection operation of the injection needle is performed.

Figure 38:
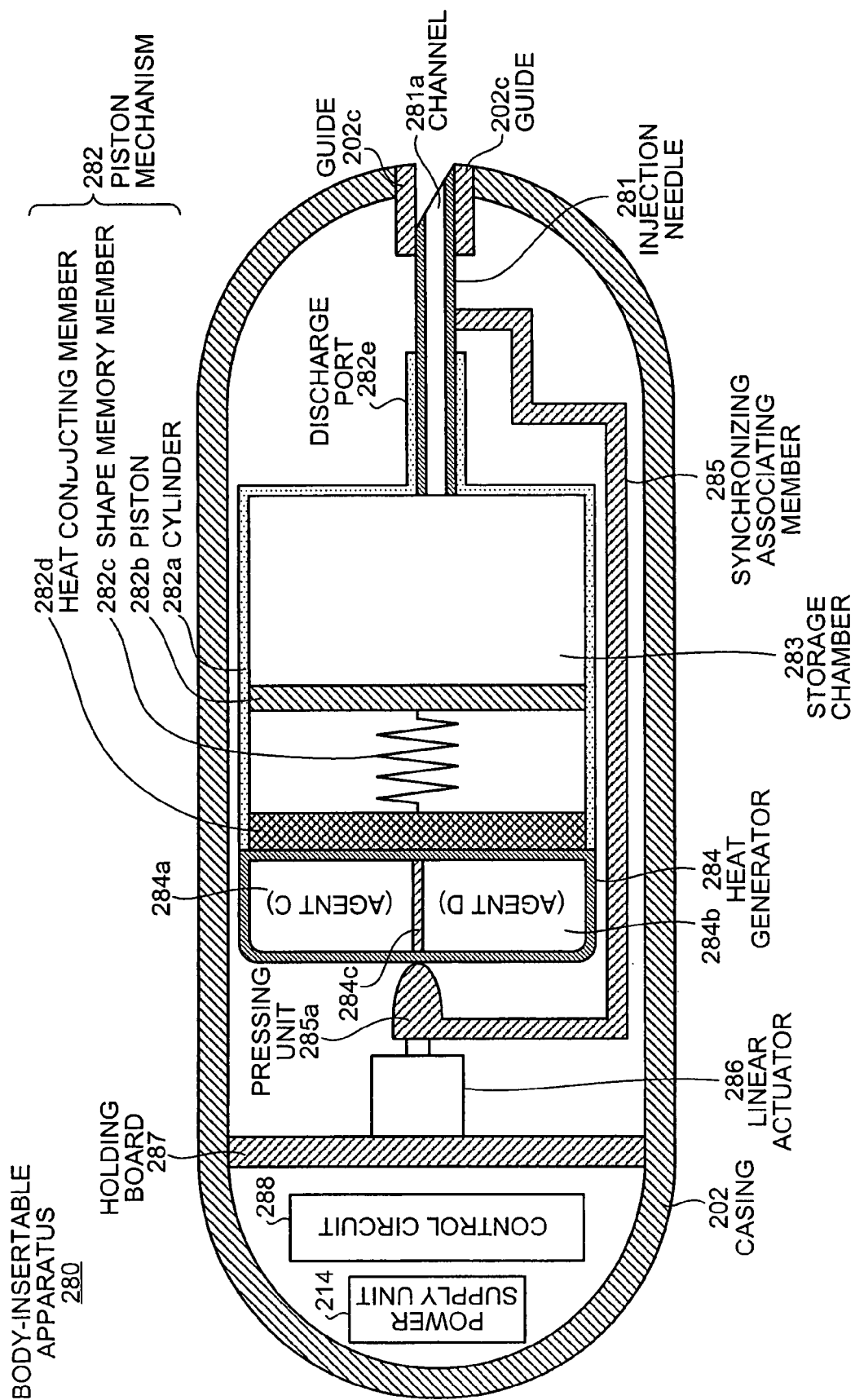
FIG. 38 is a schematic sectional view schematically showing one configuration example of a body-insertable apparatus according to a tenth embodiment of the present invention.

FIG. 38 is a schematic sectional view schematically showing one configuration example of the body-insertable apparatus according to the tenth embodiment of the present invention. As shown in FIG. 38, this body-insertable apparatus 280 includes, in the casing 202, an injection needle 281 for injecting the medical fluid to the desired region in the subject, a piston mechanism 282 that discharges the medical fluid, a heat generator 284 that generates the thermal energy as the driving energy for the piston mechanism 282, and a associating member 285 that applies predetermined pressing force to the heat generator 284 and projects the injection needle 281 from the casing 202. The body-insertable apparatus 280 also includes, in the casing 202, a linear actuator 286, which is the drive source for the associating member 285, a holding board 287 that holds the linear actuator 286, a control circuit 288 that controls the driving state of the linear actuator 286, and a power supply unit 214 that supplies driving power to the control circuit 288.

The injection needle 281 projects from the casing 202 by using the drive source for the discharge of the medical fluid to inject the medical fluid to the desired region in the subject. Specifically, the injection needle 281 has a channel 281a formed therein for connecting a distal end side (a side forming a sharp point) for puncturing the subject to a rear end side. An area from the rear end to a predetermined position on the side of the injection needle 281 is slidably inserted into a discharge port 282e of the medical fluid in the piston mechanism 282, and the distal end is slidably inserted into the guide 202c. The guide 202c is a member having a cylindrical structure, and is provided at an entrance of the injection needle 281 in the casing 202. The guide 202c regulates the moving direction of the injection needle 281 so that the injection needle 281 can be smoothly projected or stored.

The piston mechanism 282 functions as the medical-fluid discharger that discharges the medical fluid pre-stored in the storage chamber 283. Specifically, the piston mechanism 282 includes a cylinder 282a in which a discharge port 282e of the medical fluid is formed, a piston 282b that slides in the cylinder 282a, a shape memory member 282c that functions as the drive source for sliding the piston 282b, and a heat conducting member 282d that forms the bottom of the piston mechanism 282. The storage chamber 283 is formed in an area surrounded by the cylinder 282a and the piston 282b.

The cylinder 282a is a cylindrical member that forms the most part of an external wall of the piston mechanism 282, and the discharge port 282e of the medical fluid is formed at one end thereof and the heat conducting member 282d is provided so as to close an opening at the other end. The discharge port 282e forms the opening of the cylinder 82 that communicates to the storage chamber 283. The discharge port 282e is formed in a cylindrical shape at a predetermined position of the cylinder 82, and slidably supports the injection needle 281.

The piston 282b discharges the medical fluid stored in the storage chamber 283. Specifically, the piston 282b is slidably provided in the cylinder 282a, and slides in the cylinder 282a due to an operation of the shape memory member 282c to compress the storage chamber 283. The piston 282b functions so as to pressurize the medical fluid in the storage chamber 283 and discharge the medical fluid from the discharge port 282e.

The shape memory member 282c functions as the drive source for generating the driving force for sliding the piston 282b in the cylinder 282a. Specifically, the shape memory member 282c has a cylindrical or coiled (for example, SMA coil) structure, and is formed of a shape memory alloy having a predetermined shape memory characteristic. The shape memory member 282c is fixed to the piston 282b at one end, and to the heat conducting member 282d at the other end, and does not apply the driving force to the piston 282b under a temperature condition, for example, same as the temperature in the subject. In this case, the shape memory member 282c is in a loose or curled state, for example, between the piston 282b and the heat conducting member 282d, and does not generate the driving force for sliding the piston 282b.

On the other hand, the shape memory member 282c changes its shape at a predetermined temperature, for example, under a temperature condition sufficiently higher than the temperature in the subject. In this case, the shape memory member 282c has a length sufficient for the piston 282b to slide in the cylinder 282a until the piston 282b has discharged the medical fluid in an amount equal to or more than the desired amount. The shape memory member 282c generates predetermined driving force with the shape change (specifically, extension deformation), and applies the driving force to the piston 282b.

The heat conducting member 282d conducts the thermal energy generated by the heat generator 284 to the shape memory member 282c. Specifically, the heat conducting member 282d has high heat conductivity such as metal, and closes the opening at the end of the cylinder 282a to form the bottom of the piston mechanism 282. An inner face of the heat conducting member 282d (a face opposite to the piston 282b) is connected to the shape memory member 282c, and an outer face thereof (the other side opposite to the inner face) adheres to the heat generator 284 over the whole face. The heat conducting member 282d arranged in this manner efficiently conducts the thermal energy generated by the heat generator 284 to the shape memory member 282c.

The heat generator 284 generates the thermal energy sufficient for causing a shape change of the shape memory member 282c. Specifically, the heat generator 284 has storage chambers 284a and 284b formed by dividing a space inside thereof by a partition 284c, and stores agents C and D respectively in the storage chambers 284a and 284b. The partition 284c is a film member, and is easily destroyed by applying predetermined pressing force from outside. The storage chambers 284a and 284b communicate with each other, upon destruction of the partition 284c. In this case, the agents C and D are mixed together to cause chemical reaction, thereby generating thermal energy sufficient for causing a shape change of the shape memory member 282c. The heat generator 284 conducts the thermal energy generated by the chemical reaction to the heat conducting member 282d, and then to the shape memory member 282c.

The heat generator 284 is externally attached to the heat conducting member 282d as a separate body, however, the heat conducting member 282d and the heat generator 284 can be integrally formed, so that the heat conducting member 282d forms a part of the external wall of respective storage chambers 284a and 284b for the agents C and D.

The associating member 285 starts the medical-fluid discharge operation by the piston mechanism 282 and projecting the injection needle 281 from the casing 202. Specifically, a pressing unit 285a that applies the pressing force to the partition 284c of the heat generator 284 is formed at one end of the associating member 285. The pressing unit 285a of the associating member 285 is connected to a driving shaft of the linear actuator 286, and the other end thereof is connected to the side of the injection needle 281. The associating member 285 presses the pressing unit 285a against the heat generator 284 due to the operation of the linear actuator 286 to apply the pressing force to the partition 284c, and projects the injection needle 281 from the casing 202. In this case, since the partition 284c is destroyed by the pressing force of the pressing unit 285a, the heat generator 284 generates the thermal energy. The thermal energy is conducted to the shape memory member 282c via the heat conducting member 282d. The shape memory member 282c changes the shape due to the thermal energy to slide the piston 82. Accordingly, the medical-fluid discharge operation by the piston mechanism 282 is started. In other words, the associating member 285 functions as the discharge starting unit that projects the injection needle 281 using the linear actuator 286 as the drive source and starts the medical-fluid discharge operation.

The linear actuator 286 functions as the drive source for driving the associating member 285 based on the control by the control circuit 288. Specifically, the linear actuator 286 is held by the holding board 287, and the driving shaft is connected to the pressing unit 285a of the associating member 285. When predetermined driving power is supplied by the control circuit 288 to the linear actuator 286, the linear actuator 286 consumes the driving power to thrust the driving shaft, and transmits predetermined driving force to the associating member 285. The driving force has sufficient strength for enabling the pressing unit 285a to destroy the partition 284c and the associating member 285 to project the injection needle 281. On the other hand, the linear actuator 286 drives the driving shaft so as to bring the associating member 285 back to the original position based on the control by the control circuit 288. In this case, the associating member 285 moves in the direction for storing the injection needle 281 in the casing 202 due to an operation of the driving shaft. The associating member 285 moves the pressing unit 285a away from the heat generator 284 due to an operation of the linear actuator 286, and stores the injection needle 281 in the casing 202. The driving force generated by the linear actuator 286 performs the projection operation of the injection needle 281, and mixes the agents C and D by destroying the partition 284c to start the medical-fluid discharge operation (that is, an example of the physical force for the discharge of the medical fluid). The linear actuator 286 that generates the physical force for the discharge of the medical fluid is the drive source for the discharge of the medical fluid.

The control circuit 288 functions so as to control the driving state of the linear actuator 286 and control the projection operation of the injection needle 281 and the medical-fluid discharge operation by the piston mechanism 282 through the driving control. Specifically, the control circuit 288 functions so as to supply the driving power to the linear actuator 286 when the body-insertable apparatus 280 introduced in the subject reaches the desired region in the subject. Since the driving power is supplied to the linear actuator 286, the linear actuator 286 pushes the associating member 285 in a direction of pushing the pressing unit 285a against the heat generator 284. In this manner, the control circuit 288 controls the driving state of the linear actuator 286 so that the piston mechanism 282 starts the medical-fluid discharge operation and projects the injection needle 281 by using the thermal energy generated by the heat generator 284. The control circuit 288 further controls the drive of the linear actuator 286, and the pressing unit 285a moves the associating member 285 in the direction moving away from the heat generator 284. As a result, the injection needle 281 is stored in the casing 202.

As the configuration for specifying the supply timing of the driving power by the control circuit 288, for example, a timer mechanism can be provided, or a radio reception mechanism is incorporated therein and a control signal can be supplied from the outside, as in the control circuit 213.

Figure 39:
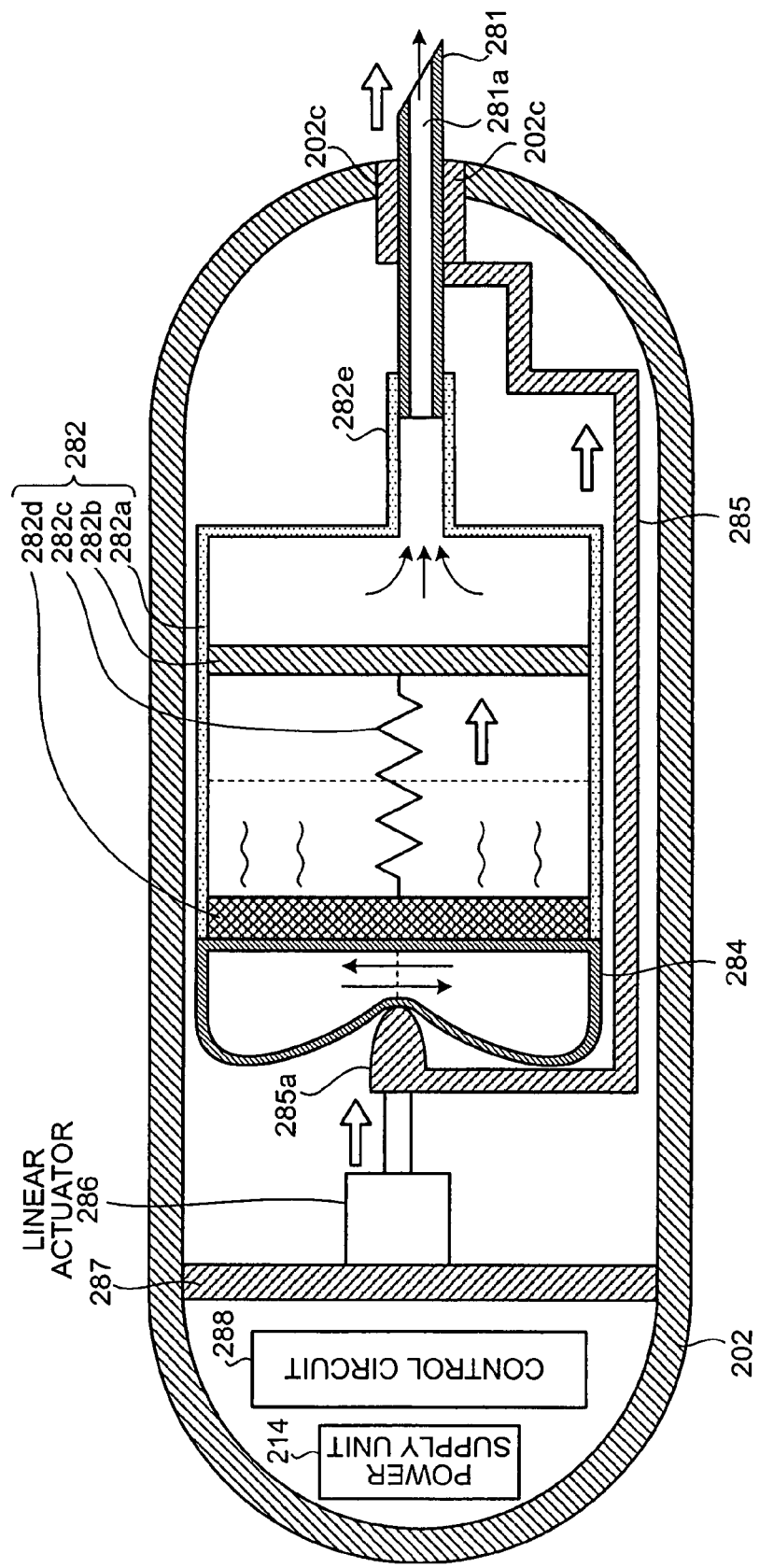
FIG. 39 is a schematic sectional view schematically exemplifying a state where the injection needle of the body-insertable apparatus in the tenth embodiment is projected.

An operation of the body-insertable apparatus 280 is explained next. FIG. 39 is a schematic sectional view schematically exemplifying a state where the injection needle 281 of the body-insertable apparatus 280 is projected. The projection operation of the injection needle 281 and the medical-fluid discharge operation are explained with reference to FIG. 39.

The control circuit 288 supplies the driving power to the linear actuator 286, and drives the linear actuator 286 so as to transmit the predetermined driving force to the associating member 285. The associating member 285 moves in the direction of pressing the heat generator 284 using the driving force. In this case, the associating member 285 projects the injection needle 281 from the casing 202, and presses the pressing unit 285a against the heat generator 284. The pressing unit 285a applies the predetermined pressing force to the partition 284c to destroy the partition 284c.

When the partition 284c is destroyed, the heat generator 284 adjusts the storage chambers 284a and 284b to the communicated state, and generates the thermal energy sufficient for causing extension deformation of the shape memory member 282c by mixing the agents C and D. The thermal energy is conducted to the shape memory member 282c via the heat conducting member 282d. The shape memory member 282c extends and deforms using the thermal energy supplied from the heat generator 284, to push the piston 282b. In this case, the shape memory member 282c generates the driving force for the piston 282b, and the piston 282b slides in the cylinder 84a using the driving force generated by the shape memory member 282c to compress the storage chamber 283. The piston 282b pressurizes the medical fluid in the storage chamber 283, to discharge the medical fluid via the discharge port 8e. In this case, the medical fluid sequentially passes through the discharge port 8e and the channel 281a, and is discharged from the distal end of the injection needle 281. The piston mechanism 282 starts the medical-fluid discharge operation synchronously with the projection operation of the injection needle 281.

Thereafter, the piston 85 continuously compresses the storage chamber 283 until the medical fluid in an amount equal to or more than the desired amount has been discharged by using the driving force by the shape memory member 282c. Accordingly, the projected injection needle 281 punctures the desired region in the subject such as the affected part, to inject the desired amount of medical fluid discharged by the operation of the piston 276 to the desired region.

On the other hand, the control circuit 288 controls the linear actuator 286 so as to pull the associating member 285 back to the original position. The linear actuator 286 pulls the pressing unit 285a in the direction moving away from the heat generator 284 based on the control of the control circuit 288. The associating member 285 stores the injection needle 281 in the casing 202 due to the operation of the linear actuator 286.

In the body-insertable apparatus 280 adopting such a configuration, the linear actuator 286 drives so as to apply predetermined pressing force to the heat generator 284 via the pressing unit 285a, the associating member 285 projects the injection needle 285 based on the drive of the linear actuator, and synchronously therewith, the heat generator 284 supplies the thermal energy to the shape memory member 282c, thereby enabling to start the medical-fluid discharge operation by the piston mechanism 282. Accordingly, the body-insertable apparatus 280 can perform the projection operation of the injection needle and the medical-fluid discharge operation simultaneously by supplying the predetermined driving power to the linear actuator 286. Accordingly, the projection operation of the injection needle can be executed in a power saving manner, without consuming additional driving power for executing the projection operation of the injection needle.

Further, the projecting unit is formed by using the associating member 285 that projects the injection needle 281 and applies the predetermined pressing force to the heat generator 284, and the linear actuator 286 as the drive source, and the energy generator that generates the driving energy for the piston mechanism 282 is formed y the heat generator 284 that generates the thermal energy synchronously with the operation of the associating member 285. The body-insertable apparatus 280 adopting such a configuration can form the discharge starting unit that starts the medical-fluid discharge operation as well as projecting the injection needle with a more simplified mechanism, thereby enabling downsizing of the apparatus easily. Further, since the body-insertable apparatus 280 can store the projected injection needle 281 in the casing 202, the injection needle can puncture only the necessary spot in the subject.

Further, since the body-insertable apparatus 280 performs the medical-fluid discharge operation by using the thermal energy chemically generated by mixing the predetermined agents, the medical-fluid discharge operation can be executed in a power saving manner, without consuming additional driving power for executing the medical-fluid discharge operation.

Eleventh Embodiment

An eleventh embodiment of the present invention is explained next. In the eleventh embodiment, a piston mechanism and an injection needle-projecting mechanism are provided, which respectively use the shape memory member as the drive source, and predetermined thermal energy is supplied to the piston mechanism and the projecting mechanism simultaneously, to perform the projection operation of the injection needle and the medical-fluid discharge operation synchronously.

Figure 40:
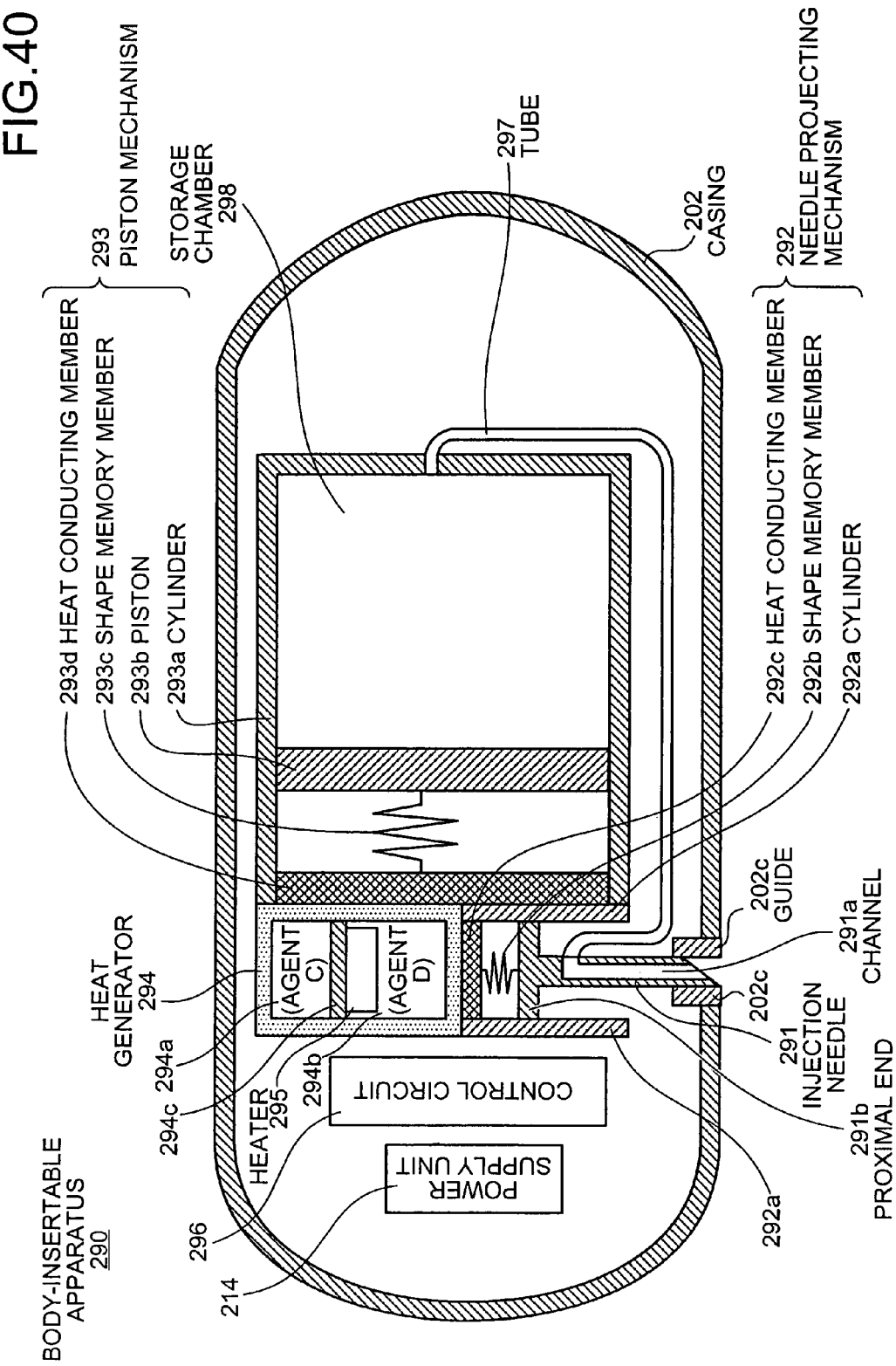
FIG. 40 is a schematic sectional view schematically showing one configuration example of a body-insertable apparatus according to an eleventh embodiment of the present invention.

FIG. 40 is a schematic sectional view schematically showing one configuration example of the body-insertable apparatus according to the eleventh embodiment of the present invention. As shown in FIG. 40, this body-insertable apparatus 290 includes, in the casing 202, an injection needle 291 for injecting the medical fluid to the desired region in the subject, a needle projecting mechanism that projects the injection needle 291 from the casing 202, and a piston mechanism 293 that discharges the medical fluid. The body-insertable apparatus 290 further includes, in the casing 202, a tube 297 for connecting the injection needle 291 and the piston mechanism 92 with each other, a heat generator 294 that generates the driving energy for the piston mechanism 293, a heater 295 for starting generation of the thermal energy by the heat generator 294, a control circuit 296 that controls the driving state of the heater 295, and the power supply unit 214 that supplies driving power to the control circuit 296.

The injection needle 291 projects from the casing 202 by using the drive source for the discharge of the medical fluid to inject the medical fluid to the desired region in the subject. Specifically, the injection needle 291 has a channel 291a formed therein for connecting a distal end side (a side forming a sharp point) for puncturing the subject to a side near a rear end. The channel 291a is connected to the tube 297 at an opening on the side of the injection needle 291, and connects to a storage chamber 298 for the medical fluid via the tube 297. The injection needle 291 has a brim-like proximal end 291b formed at a rear end. The proximal end 291b functions as a piston that slides in a cylinder 292a in the needle projecting mechanism 292.

The distal end of the injection needle 291 is slidably inserted into the guide 202c. The guide 202c is a member having a cylindrical structure, and is provided at an entrance of the injection needle 291 in the casing 202. The guide 202c regulates the moving direction of the injection needle 291 so that the injection needle 291 can be smoothly projected or stored.

The needle projecting mechanism 292 functions as the projecting unit that projects the injection needle 291 from the casing 202 by using the thermal energy. Specifically, the needle projecting mechanism 292 has the cylinder 292a that slidably supports the proximal end 291b of the injection needle 291, a shape memory member 292b as the drive source for the projection operation of the injection needle 291, and a heat conducting member 292c that conducts the thermal energy to the shape memory member 292b.

The cylinder 292a is a member having a cylindrical structure, and slidably supports the injection needle 291 therein. Specifically, the cylinder 292a supports the injection needle 291 such that an inner wall thereof comes in contact with the side of the proximal end 291b of the injection needle 291. Further, one end of the cylinder 292a is open, and the other end is closed by the heat conducting member 292c. In the cylinder 292a, the opening at one end is arranged so as to face the guide 202c, to slidably support the injection needle 291, and also functions as a guide for regulating the sliding direction of the injection needle 291.

The shape memory member 292b functions as a drive source that generates the driving force for sliding the injection needle 291 in the cylinder 292a. Specifically, the shape memory member 292b has a cylindrical or coiled (for example, SMA coil) structure, and is formed of a shape memory alloy having a predetermined shape memory characteristic. The shape memory member 292b is fixed to the proximal end 291b of the injection needle 291 at one end, and to the heat conducting member 292c at the other end, and does not apply the driving force to the injection needle 291 under a temperature condition, for example, same as the temperature in the subject. In this case, the shape memory member 292b is in a loose or curled state, for example, between the proximal end 291b and the heat conducting member 292c, and does not generate the driving force for sliding the injection needle 291.

On the other hand, the shape memory member 292b changes its shape at a predetermined temperature, for example, under a temperature condition sufficiently higher than the temperature in the subject. In this case, the shape memory member 292b has a length sufficient for projecting the injection needle 291 from the casing 202. The shape memory member 292b generates predetermined driving force with the shape change (specifically, extension deformation), and applies the driving force to the proximal end 291b of the injection needle 291.

The heat conducting member 292c conducts the thermal energy generated by the heat generator 294 to the shape memory member 292b. Specifically, the heat conducting member 292c has high heat conductivity such as metal, and forms the bottom of the cylinder 292a. An inner face of the heat conducting member 292c (a face opposite to the proximal end 291b) is connected to the shape memory member 292b, and an outer face thereof (the other side opposite to the inner face) adheres to the heat generator 294 over the whole face. The heat conducting member 292c arranged in this manner efficiently conducts the thermal energy generated by the heat generator 294 to the shape memory member 292b.

The piston mechanism 293 functions as the medical-fluid discharger that discharges the medical fluid pre-stored in the storage chamber 298. Specifically, the piston mechanism 293 includes a cylinder 293a that forms the most part of an outer circumference of the storage chamber 298, a piston 293b that slides in the cylinder 293a, a shape memory member 293c that functions as the drive source for sliding the piston 293b, and a heat conducting member 293d that forms the bottom of the piston mechanism 293. The storage chamber 298 is formed in an area surrounded by the cylinder 293a and the piston 293b.

The cylinder 293a is a cylindrical member that forms the most part of an external wall of the piston mechanism 293, and the tube 297 is connected to one end thereof and the heat conducting member 293d is provided so as to close an opening at the other end. The tube 297 is connected to the cylinder 293a so as to communicate to the storage chamber 283.

The piston 293b discharges the medical fluid stored in the storage chamber 298. Specifically, the piston 293b is slidably provided in the cylinder 293a, and slides in the cylinder 293a due to the later described operation of the shape memory member 293c to compress the storage chamber 298. The piston 293b functions so as to pressurize the medical fluid in the storage chamber 298 and circulate the medical fluid to the tube 297.

The shape memory member 293c functions as the drive source for generating the driving force for sliding the piston 293b in the cylinder 282a. Specifically, the shape memory member 293c has a cylindrical or coiled (for example, SMA coil) structure, and is formed of a shape memory alloy having a predetermined shape memory characteristic. The shape memory member 293c is fixed to the piston 293b at one end, and to the heat conducting member 293d at the other end, and does not apply the driving force to the piston 293b under a temperature condition, for example, same as the temperature in the subject. In this case, the shape memory member 293c is in a loose or curled state, for example, between the piston 293b and the heat conducting member 293d, and does not generate the driving force for sliding the piston 293b.

On the other hand, the shape memory member 293c changes its shape at a predetermined temperature, for example, under a temperature condition sufficiently higher than the temperature in the subject. In this case, the shape memory member 293c has a length sufficient for the piston 293b to slide in the cylinder 293a until the piston 293b has discharged the medical fluid in an amount equal to or more than the desired amount. The shape memory member 293c generates predetermined driving force with the shape change (specifically, extension deformation), and applies the driving force to the piston 293b.

The heat conducting member 293d conducts the thermal energy generated by the heat generator 294 to the shape memory member 293c. Specifically, the heat conducting member 293d has high heat conductivity such as metal, and closes the opening at the end of the cylinder 293a to form the bottom of the piston mechanism 293. An inner face of the heat conducting member 282d (a face opposite to the piston 293b) is connected to the shape memory member 293c, and an outer face thereof (the other side opposite to the inner face) adheres to the heat generator 294 over the whole face. The heat conducting member 293d arranged in this manner efficiently conducts the thermal energy generated by the heat generator 294 to the shape memory member 293c.

The heat generator 294 generates the thermal energy sufficient for causing a shape change of the shape memory members 292b and 293c simultaneously. Specifically, the heat generator 294 has storage chambers 294a and 294b formed by dividing a space inside thereof by a partition 294c, and stores agents C and D respectively in the storage chambers 294a and 294b. The partition 284c is a polymer membrane that dissolves upon heating to a predetermined temperature or higher. The storage chambers 294a and 294b communicate with each other, upon dissolution or destruction of the partition 294c. In this case, the agents C and D are mixed together to cause chemical reaction, thereby generating thermal energy sufficient for causing a shape change of the shape memory members 292b and 293c. The heat generator 294 conducts the thermal energy generated by the chemical reaction to the heat conducting members 292c and 293d. Thereafter, the thermal energy is conducted to the shape memory members 292b and 293c. The heat generator 294 is a drive source that generates the driving energy used for the projection operation of the injection needle 291 (thermal energy transmitted to the shape memory member 292b), and a drive source that generates the driving energy used for the medical-fluid discharge operation (thermal energy transmitted to the shape memory member 293c), that is, a drive source for the discharge of the medical fluid.

The heat generator 294 is externally attached to the heat conducting members 292c and 293d as a separate body, however, the heat conducting members 292c and 293d and the heat generator 294 can be integrally formed, so that the heat conducting members 292c and 293d form a part of the external wall of the heat generator 294.

The heater 295 heats the partition 294c to a temperature equal to or higher than a predetermined temperature based on the control of the control circuit 296. Specifically, the heater 295 is attached to the partition 294c, and generates heat upon supply of predetermined current by the control circuit 296. The heater 295 heats the partition 294c to a predetermined temperature or higher due to the heat generation, to dissolve the partition 294c. In other words, the heater 295 functions as a drive source for generating the driving energy (thermal energy) for starting generation of the thermal energy by the heat generator 294.

By combining the needle projecting mechanism 292 and the heat generator 294, the heater 295 is used as the drive source, thereby forming the discharge starting unit that generates thermal energy for projecting the injection needle 291 and starting the medical-fluid discharge operation by the piston mechanism 293. In this case, the needle projecting mechanism 292 is the projecting unit of the injection needle in the discharge starting unit, and the heat generator 294 is the energy generator in the discharge starting unit.

The control circuit 296 functions so as to start the thermal energy generation processing according to the presence of current supply to the heater 295, and control the projection operation of the injection needle 291 and the medical-fluid discharge operation by the piston mechanism 293 through the control for starting the generation processing. Specifically, the control circuit 296 functions so as to supply the current to the heater 295 when the body-insertable apparatus 290 introduced in the subject reaches the desired region in the subject. Thus, by supplying the current to the heater 295, the control circuit 296 controls start of the thermal energy generation processing by the heat generator 294, thereby enabling control of simultaneous execution of the projection operation of the injection needle 291 and the medical-fluid discharge operation by the piston mechanism 293.

As the configuration for specifying the supply timing of the current supply by the control circuit 296, for example, a timer mechanism can be provided, or a radio reception mechanism is incorporated therein and a control signal can be supplied from the outside, as in the control circuit 213.

Figure 41:
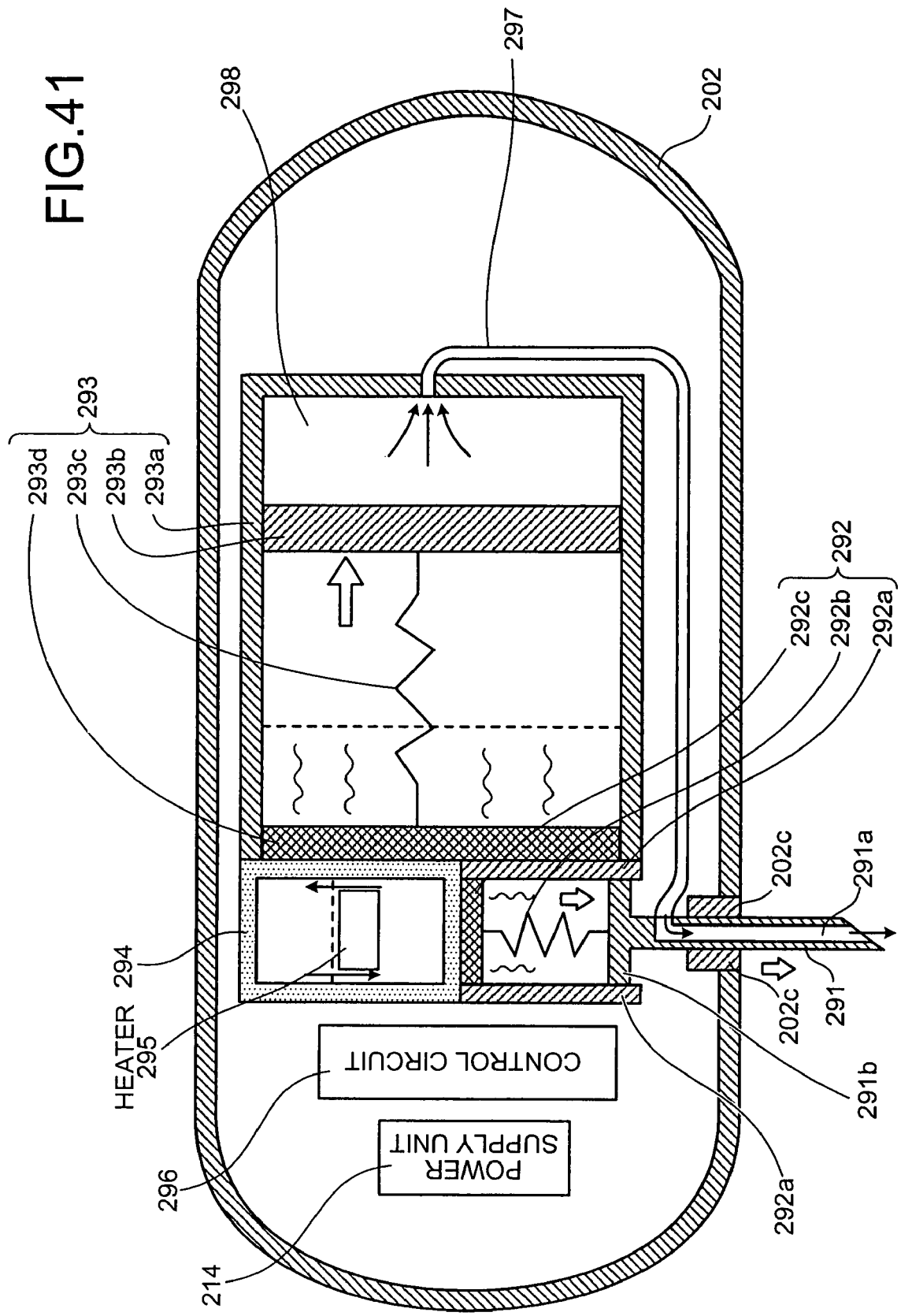
FIG. 41 is a schematic sectional view schematically exemplifying a state where the injection needle of the body-insertable apparatus according to the eleventh embodiment is projected.

An operation of the body-insertable apparatus 290 is explained next. FIG. 41 is a schematic sectional view schematically exemplifying a projected state of the injection needle 291 of the body-insertable apparatus 290. The projection operation of the injection needle 291 and the medical-fluid discharge operation are explained with reference to FIG. 41.

The control circuit 296 supplies the current to the heater 295, so that the heater 295 generates heat for heating the partition 294c to a temperature equal to or higher than the predetermined temperature. The partition 294c dissolves or tears due to heating by the heater 295. In this case, the storage chambers 294a and 294b are adjusted to the communicated state, and the agents C and D mix with each other, to generate the thermal energy sufficient for causing extension deformation of the shape memory members 292b and 293c. The thermal energy is conducted to the shape memory member 292b via the heat conducting member 292c, and conducted to the shape memory member 293c via the heat conducting member 293d.

The shape memory member 292b extends and deforms using the thermal energy supplied from the heat generator 294 to push the injection needle 291. In this case, the shape memory member 292b generates the driving force for the injection needle 291, and the injection needle 291 slides in the cylinder 292a using the driving force by the shape memory member 292b to project from the casing 202.

Simultaneously, the shape memory member 293c extends and deforms using the thermal energy supplied from the heat generator 294 to push the piston 293b. In this case, the shape memory member 293c generates the driving force for the piston 293b, and the piston 293b slides in the cylinder 293a using the driving force by the shape memory member 293c to compresses the storage chamber 298. The piston 293b pressurizes the medical fluid in the storage chamber 298, to discharge the medical fluid into the channel 291a via the tube 297. In this case, the medical fluid passes through the channel 291a, and is discharged from the distal end of the injection needle 291. The piston mechanism 293 starts the medical-fluid discharge operation synchronously with the projection operation of the injection needle 291.

Thereafter, the piston 293b continuously compresses the storage chamber 298 until the medical fluid in an amount equal to or more than the desired amount has been discharged by using the driving force by the shape memory member 293c. Accordingly, the projected injection needle 291 punctures the desired region in the subject such as the affected part, to inject the desired amount of medical fluid discharged by the operation of the piston 293b to the desired region.

In the body-insertable apparatus 290 adopting such a configuration, the predetermined thermal energy is chemically generated by supplying the current to the heater 295, and the injection needle 291 is projected by using the thermal energy, thereby enabling to start the medical-fluid discharge operation. Accordingly, the body-insertable apparatus 290 can perform the projection operation of the injection needle and the medical-fluid discharge operation simultaneously by supplying the predetermined current to the heater 295. Accordingly, the projection operation of the injection needle can be executed in a power saving manner, without consuming additional driving power for executing the projection operation of the injection needle.

The discharge starting unit that uses the heater 295 as the drive source to generate the thermal energy for projecting the injection needle 291 and starting the medical-fluid discharge operation by the piston mechanism 293 can be formed by combining the needle projection mechanism 292 and the heat generator 294. The body-insertable apparatus 290 adopting such a configuration can form the discharge starting unit that starts the medical-fluid discharge operation as well as projecting the injection needle with a more simplified mechanism, thereby enabling downsizing of the apparatus easily.

Further, since the body-insertable apparatus 290 performs the projection operation of the injection needle and the medical-fluid discharge operation by using the thermal energy chemically generated by mixing the predetermined agents, the projection operation of the injection needle and the medical-fluid discharge operation can be executed in a power saving manner, without consuming additional driving power for executing the discharge operation of the injection needle and the medical-fluid discharge operation.

Figure 42:
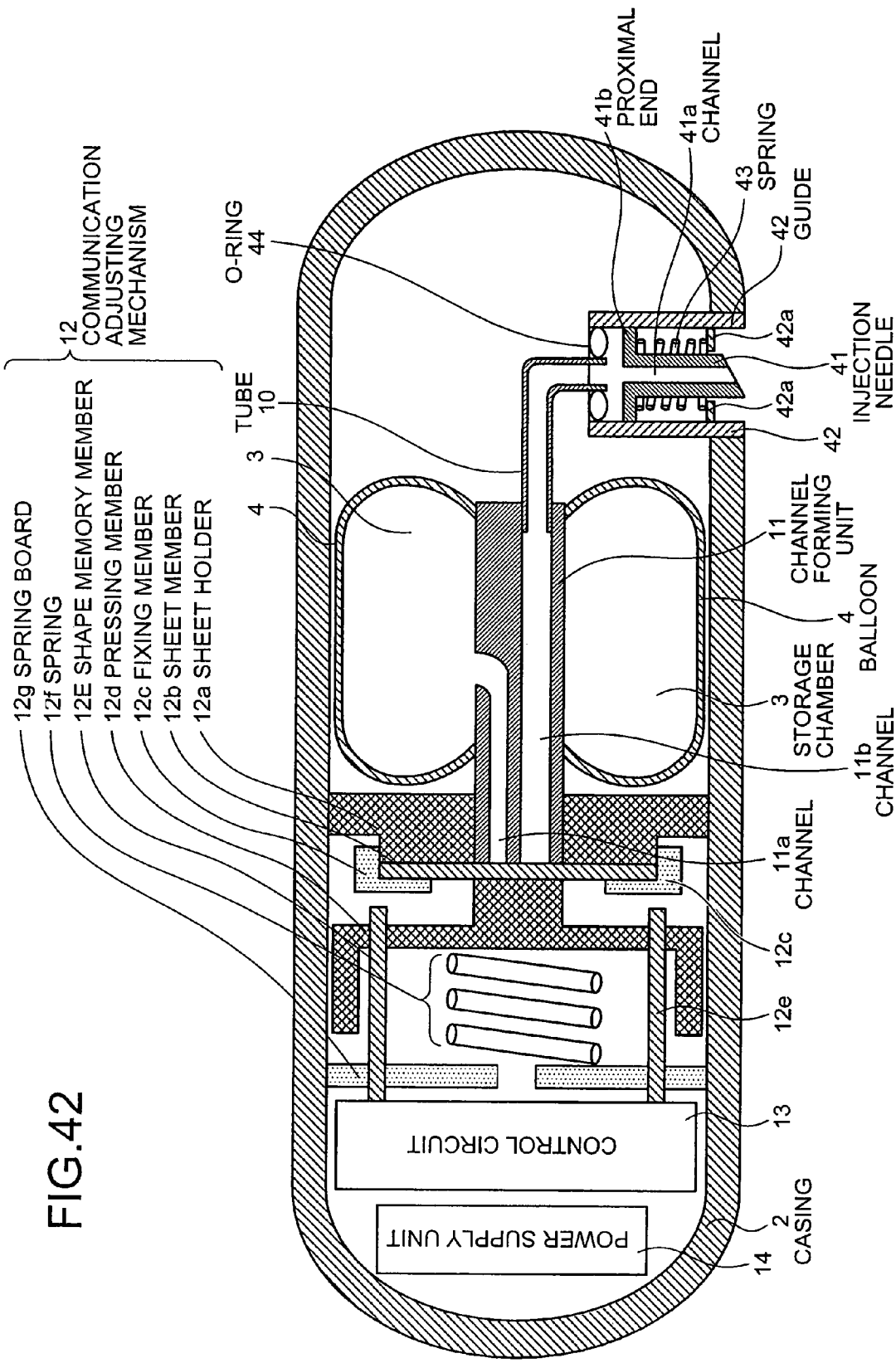
FIG. 42 is a schematic sectional view schematically showing one configuration example of the body-insertable apparatus in which a projecting direction of the injection needle is changed.

In the embodiments and modifications of the present invention, the injection needle is projected to a predetermined direction. However, the present invention is not limited thereto, and the projecting direction can be optional, for example, the injection needle can be projected to a direction forming a desired angle relative to the longitudinal central axis of the casing. For example, in the body-insertable apparatus 40 according to the second embodiment, the projecting direction of the injection needle 41 is not limited to the same direction as the longitudinal direction of the casing 2, and as shown in FIG. 42, the injection needle 41 can be projected to the side of the casing 2, for example, to a direction forming an angle of approximately 90 degrees relative to the longitudinal central axis of the casing 2. In this case, a tube for circulating the medical fluid to the injection needle (for example, the tube 10) can be provided so as to be deformed corresponding to the projecting direction of the injection needle. This applies to other embodiments and modifications.

In the first modification of the second embodiment, the medical fluid is discharged by using the contraction force of the balloon 4. However, the present invention is not limited thereto, and the medical fluid can be discharged by using the piston mechanism as in the second modification of the second embodiment. In this case, the driving force of the piston mechanism can be the elastic force of the spring, or can be based on the shape change of the shape memory member as in the second modification of the second embodiment.

In the third embodiment of the present invention, the balloon 4 and the injection needle 71 are linked via the linking members 77 and 78, and the contraction operation of the balloon 4 is changed to the projection operation of the injection needle 71 by the linking members 77 and 78. However, the present invention is not limited thereto, and the piston mechanism can be provided instead of the balloon 4 as in the first modification of the second embodiment, and the injection needle can be projected by using the sliding operation of the piston by the piston mechanism. In this case, the piston and the injection needle are linked via a linking member, and sliding of the piston can be changed to the projection operation of the injection needle by the linking member.

In the modification of the fourth embodiment of the present invention, the linear actuator is used as the drive source of the piston mechanism. However, the present invention is not limited thereto, and an ultrasonic actuator or a solenoid can be used as the drive source of the piston mechanism, or the shape memory member can be used as in the second modification of the first embodiment.

Further, in the sixth embodiment and the first and second modifications thereof, the communication adjusting operation by the communication adjusting mechanism 208 and the projection operation of the injection needle are performed substantially simultaneously by using the associating members 208f and 208g. However, the present invention is not limited thereto, and the communication adjusting operation by the communication adjusting mechanism 208 and the projection operation of the injection needle can be performed with time difference by forming slack in the associating members 208f and 208g. By adopting such a configuration, the medical-fluid discharge operation can be started after the injection needle is projected, thereby preventing that while the injection needle punctures the desired region in the subject, the medical fluid leaks uselessly to other regions in the subject.

Further, in the seventh and the eighth embodiments of the present invention, the balloon is used as the medical-fluid discharger that performs the medical-fluid discharge operation. However, the present invention is not limited thereto, and as exemplified in the second modification of the sixth embodiment, the piston mechanism that performs the medical-fluid discharge operation can be provided instead of the balloon. Further, a medical-fluid discharger that discharges the medical fluid by reducing the volume of the medical-fluid storage chamber using s suction pump or the like can be provided, instead of the medical-fluid discharger that discharges the medical fluid by compressing the medical-fluid storage chamber, such as the balloon and the piston mechanism. In this case, the discharge starting unit that starts the discharge operation of the medical-fluid discharger needs only to perform the projection operation of the injection needle and start suction operation of the suction pump in the medical-fluid discharger to start the medical-fluid discharge operation.

(Note 1) A body-insertable apparatus having a storage chamber for storing a medical fluid in a capsule-like casing and an injection needle, and introduced into a subject to inject the medical fluid into a desired region in the subject, comprising:
 a medical-fluid discharger that discharges the medical fluid by reducing the volume of the storage chamber and projects the injection needle from the casing by using a physical force for the discharge of the medical fluid; and
 a discharge controller that controls the start of volume reduction of the storage chamber by the medical-fluid discharger to start the discharge of the medical fluid.

(Note 2) The body-insertable apparatus according to note 1, wherein the physical force for the discharge of the medical fluid is a discharge pressure of the medical fluid.

(Note 3) The body-insertable apparatus according to note 1, wherein the physical force for the discharge of the medical fluid is a pressurizing force for pressurizing the medical fluid by reducing the volume of the storage chamber.

(Note 4) The body-insertable apparatus according to note 2, wherein the medical-fluid discharger comprises:
 a medical fluid pressurizing unit that pressurizes the medical fluid by reducing the volume of the storage chamber;
 an elastic membrane that holds the injection needle; and
 a medical fluid channel for allowing the medical fluid pressurized by the medical fluid pressurizing unit to flow toward the elastic membrane side, wherein
 the elastic membrane expands by using the discharge pressure of the medical fluid flowing via the medical fluid channel, and the injection needle is projected from the casing due to the expansion.

(Note 5) The body-insertable apparatus according to note 4, wherein the elastic membrane uses the discharge pressure of the medical fluid to expand and generate an elastic force, and when the discharge pressure of the medical fluid decreases to equal to or less than the elastic force, the injection needle is returned into the casing by using the elastic force.

(Note 6) The body-insertable apparatus according to note 2, wherein the medical-fluid discharger comprises:
 a medical fluid pressurizing unit that pressurizes the medical fluid by reducing the volume of the storage chamber; and
 a medical fluid channel for allowing the medical fluid pressurized by the medical fluid pressurizing unit to flow to an end of the injection needle, wherein
 the medical fluid pressurizing unit pushes out the injection needle by applying the discharge pressure of the medical fluid to the end of the injection needle.

(Note 7) The body-insertable apparatus according to note 6, wherein one end of the medical fluid channel is connected to the end of the injection needle, and the vicinity of the one end of the medical fluid channel can freely extend in a projecting direction of the injection needle.

(Note 8) The body-insertable apparatus according to note 6 or 7, further comprising an elastic member that projects the injection needle by the medical-fluid discharger and generates the elastic force, and when the discharge pressure of the medical fluid decreases to equal to or less than the elastic force, uses the elastic force to return the injection needle into the casing.

(Note 9) The body-insertable apparatus according to note 3, wherein the medical-fluid discharger comprises:
 a medical fluid pressurizing unit that pressurizes the medical fluid by reducing the volume of the storage chamber;
 a medical fluid channel for allowing the medical fluid pressurized by the medical fluid pressurizing unit to flow to the injection needle; and
 a linking unit that links the medical fluid pressurizing unit to the injection needle and uses the pressurizing force by the medical fluid pressurizing unit to project the injection needle, in conjunction with the volume reduction of the storage chamber.

(Note 10) The body-insertable apparatus according to note 9, further comprising:
 an elastic member that generates an elastic force in a direction returning the injection needle into the casing, upon projection of the injection needle; and
 a cutting unit that cuts the linking unit when the injection needle projects to a predetermined position, wherein
 the elastic member uses the elastic force to return the injection needle into the casing, when the cutting unit cuts the linking unit.

(Note 11) The body-insertable apparatus according to note 3, wherein the medical-fluid discharger comprises:
a medical fluid pressurizing unit including the injection needle, which pressurizes the medical fluid by reducing the volume of the storage chamber and projects the injection needle from the casing; and
a medical fluid channel for allowing the medical fluid pressurized by the medical fluid pressurizing unit to flow to the injection needle.

(Note 12) The body-insertable apparatus according to note 11, wherein the medical fluid pressurizing unit comprises:
 a pressurizing force source that generates the pressuring force; and
 a piston including the injection needle, which uses the pressurizing force of the pressurizing force source to slide in the storage chamber, pressurizes the medical fluid, and projects the injection needle from the casing.

(Note 13) The body-insertable apparatus according to note 11, wherein the storage chamber is formed of a deformable medical fluid bag including the medical fluid channel, and the medical fluid pressurizing unit comprises:
 a belt wound around the medical fluid bag;
 a shape memory member that deforms to generate the pressurizing force, upon reaching predetermined temperature; and
 an associating unit fitted with one end of the belt, the injection needle, and the shape memory member, which uses the pressurizing force by the shape memory member to shift one end of the belt in a direction fastening the medical fluid bag and projects the injection needle from the casing.

(Note 14) The body-insertable apparatus according to note 13, wherein the shape memory member returns to an original shape to lose the pressurizing force when the temperature thereof decreases to lower than the predetermined temperature, and returns the injection needle into the casing.

(Note 15) The body-insertable apparatus according to note 14, wherein the discharge controller controls to raise the temperature of the shape memory member to higher than the predetermined temperature to start discharge of the medical fluid, or to drop the temperature of the shape memory member to lower than the predetermined temperature to stop the discharge of the medical fluid.

(Note 16) The body-insertable apparatus according to any one of notes 1 to 12, wherein the discharge controller controls so as to stop volume reduction of the storage chamber by the medical-fluid discharger, to stop the discharge of the medical fluid.

(Note 17) The body-insertable apparatus according to note 16, wherein the medical fluid channel comprises:
 a first channel connecting to the storage chamber; and
 a second channel connecting to the injection needle side,
 the discharge controller controls the connection state of the first channel and the second channel, and
 the medical-fluid discharger starts volume reduction of the storage chamber when the first channel and the second channel are connected to each other, and stops volume reduction of the storage chamber when the first channel and the second channel are closed.

(Note 18) A body-insertable apparatus having a medical fluid and an injection needle in a capsule-like casing, and introduced into a subject to inject the medical fluid to a desired region in the subject, wherein the body-insertable apparatus comprises:
 a medical-fluid discharger that pressurizes and discharges the medical fluid, and projects the injection needle from the casing; and
 an elastic member that generates an elastic force in a direction returning the injection needle into the casing, upon projection of the injection needle, and when a physical force for projecting the injection needle decreases to equal to or less than the elastic force, uses the elastic force to return the injection needle into the casing.

(Note 19) The body-insertable apparatus according to note 18, wherein the physical force for projecting the injection needle is a discharge pressure of the medical fluid, and decreases to equal to or less than the elastic force when the medical-fluid discharger finishes discharge of a desired amount of the medical fluid.

(Note 20) The body-insertable apparatus according to note 18 or 19, further comprising a discharge controller that performs controls to stop discharge of the medical fluid, so that the physical force for projecting the injection needle decreases to equal to or less than the elastic force.

(Note 21) The body-insertable apparatus according to note 18, wherein the physical force for projecting the injection needle is a pressurizing force for pressurizing the medical fluid, and the medical-fluid discharger comprises:
 a linking unit that links the injection needle to the medical-fluid discharger and uses the pressurizing force to project the injection needle; and
 a cutting unit that cuts the linking unit when the injection needle projects to a predetermined position, to reduce the physical force for projecting the injection needle to equal to or less than the elastic force.

(Note 22) A body-insertable apparatus having a storage chamber for storing a medical fluid and an injection needle in a capsule-like casing, and introduced into a subject to inject the medical fluid to a desired region in the subject, wherein the body-insertable apparatus comprises:
 a medical-fluid discharger that discharges the medical fluid by changing the volume of the storage chamber; and
 a discharge starting unit that projects the injection needle from the casing by using a predetermined drive source and starts a discharge operation of the medical-fluid discharger.

(Note 23) The body-insertable apparatus according to note 22, wherein the medical-fluid discharger discharges the medical fluid by compressing the storage chamber.

(Note 24) The body-insertable apparatus according to note 22 or 23, wherein the medical-fluid discharger comprises a medical fluid channel for connecting the storage chamber to the injection needle, and
 the discharge starting unit is a communication adjusting unit that applies a pressing force to a part of the medical fluid channel to cut off the communicated state of the medical fluid channel, projects the injection needle by using the predetermined drive source, and reduces the pressing force to adjust the medical fluid channel to the communicated state, thereby starting the discharge operation of the medical-fluid discharger.

(Note 25) The body-insertable apparatus according to note 24, wherein the communication adjusting unit comprises:
 a pressing unit that applies a pressing force to a part of the medical fluid channel to cut off the communicated state of the medical fluid channel;
 a projecting unit that holds the injection needle and uses the predetermined drive source to project the injection needle from the casing; and
 an associating unit that associates the projection operation by the projecting unit to project the injection needle with the communication adjusting operation by the pressing unit to reduce the pressing force to adjust the medical fluid channel to the communicated state.

(Note 26) The body-insertable apparatus according to note 24 or 25, wherein the medical fluid channel comprises:
 a first channel connecting to the storage chamber; and
 a second channel connecting to the injection needle, and
 the communication adjusting unit applies a pressing force to a region between the first channel and the second channel to cut off the communicated state of the medical fluid channel, projects the injection needle by using the predetermined drive source, and adjusts the medical fluid channel to the communicated state by reducing the pressing force, thereby starting the discharge operation of the medical-fluid discharger.

(Note 27) The body-insertable apparatus according to any one of notes 24 to 26, wherein the predetermined drive source is a shape memory member, and
 the communication adjusting unit uses a driving force generated by a shape change of the shape memory member to project the injection needle, and adjusts the medical fluid channel to the communicated state.

(Note 28) The body-insertable apparatus according to note 27, wherein the communication adjusting unit comprises an elastic member that generates the pressing force, and when the shape memory member loses the driving force, uses the pressing force to store at least the injection needle in the casing.

(Note 29) The body-insertable apparatus according to note 22 or 23, wherein the discharge starting unit comprises:
 a projecting unit that projects the injection needle by using the predetermined drive source; and
 an energy generator that contains a first agent and a second medicine, mixes the first agent and the second medicine, in conjunction with the projection operation of the projecting unit to project the injection needle, and chemically generates a driving energy to transmit the driving energy to the medical-fluid discharger, and the medical-fluid discharger discharges the medical fluid by using the driving energy.

(Note 30) The body-insertable apparatus according to note 22 or 23, wherein the discharge starting unit comprises:
  an energy generator that contains a first agent and a second medicine, mixes the first agent and the second agent By using the predetermined drive source, and chemically generates a driving energy to transmit the driving energy to the medical-fluid discharger, and
  a projecting unit that projects the injection needle by using the driving energy.

(Note 31) The body-insertable apparatus according to note 30, wherein the driving energy is thermal energy, and the projecting unit comprises a shape memory member that extends by using the thermal energy to generate a driving force for projecting the injection needle.

(Note 32) The body-insertable apparatus according to any one of notes 29 to 31, wherein the driving energy is thermal energy, and
  the medical-fluid discharger comprises a shape memory member that extends by using the thermal energy to generate a pressurizing force for compressing the storage chamber.

(Note 33) A body-insertable apparatus having a storage chamber for storing a medical fluid in a capsule-like casing and an injection needle, introduced into a subject to inject the medical fluid into a desired region in the subject, comprising:
  a shape memory member that changes its shape under a predetermined temperature condition to generate a driving force;
  an elastic member that generates an elastic force against the driving force and less than the driving force; and
  a storing unit that projects the injection needle from the casing by using the driving force, and when the shape memory member loses the driving force, stores the injection needle in the casing by using the elastic force.

(Note 34) The body-insertable apparatus according to note 33, comprising a medical-fluid discharger that has a medical fluid channel connecting the storage chamber and the injection needle, and discharges the medical fluid via the medical fluid channel, wherein
  the storing unit applies the elastic force to a part of the medical fluid channel to cut off the communicated state of the medical fluid channel, thereby stopping the discharge operation of the medical-fluid discharger.

INDUSTRIAL APPLICABILITY

As described above, the body-insertable apparatus according to the present invention is useful for downsizing a capsule medical device introduced into a subject such as a patient and for reducing power consumption, and is particularly suitable for the capsule medical device including a local injection function for injecting a medical fluid to a desired region in the subject.

The invention claimed is:

1. A body-insertable apparatus having a storage chamber for storing a medical fluid in a capsule-like casing, the capsule-like casing being configured to be wholly introduced into a subject to discharge the medical fluid to a desired region in the subject, comprising:
  a medical-fluid discharger forming the storage chamber that has, in a state where it stores the medical fluid therein, a contraction force for reducing the volume of itself to discharge the medical fluid; wherein the medical-fluid discharger is provided in the casing and discharges the medical fluid using the contraction force;
  a medical-fluid discharger that is provided in the casing and discharges the medical fluid by causing the volume of the storage chamber to be reduced using the contraction force; and
  an injection needle that projects from the casing by using a physical force generated by the medical-fluid discharger for discharge of the medical fluid, to inject the medical fluid in the storage chamber into the desired region in the subject.

2. The body-insertable apparatus according to claim 1, further comprising a discharge controller that controls the start of volume change of the storage chamber by the medical-fluid discharger to start the discharge of the medical fluid.

3. The body-insertable apparatus according to claim 2, wherein the discharge controller controls so as to stop volume reduction of the storage chamber by the medical-fluid discharger, to stop the discharge of the medical fluid.

4. The body-insertable apparatus according to claim 1, wherein the physical force for the discharge of the medical fluid is a discharge pressure of the medical fluid.

5. The body-insertable apparatus according to claim 4, wherein the medical-fluid discharger includes
  a medical fluid pressurizing unit that pressurizes the medical fluid by reducing the volume of the storage chamber,
  an elastic membrane that holds the injection needle, and
  a medical fluid channel for allowing the medical fluid pressurized by the medical fluid pressurizing unit to flow toward the elastic membrane side, wherein
  the elastic membrane expands by using the discharge pressure of the medical fluid flowing via the medical fluid channel, and the injection needle is projected from the casing due to the expansion.

6. The body-insertable apparatus according to claim 5, wherein the elastic membrane uses the discharge pressure of the medical fluid to expand and generate an elastic force, and when the discharge pressure of the medical fluid decreases to equal to or less than the elastic force, the elastic membrane brings the injection needle back to the casing by using the elastic force.

7. The body-insertable apparatus according to claim 4, wherein the medical-fluid discharger includes
  a medical fluid pressurizing unit that pressurizes the medical fluid by reducing the volume of the storage chamber, and
  a medical fluid channel for allowing the medical fluid pressurized by the medical fluid pressurizing unit to flow to an end of the injection needle, wherein
  the medical fluid pressurizing unit pushes out the injection needle by applying the discharge pressure of the medical fluid to the end of the injection needle.

8. The body-insertable apparatus according to claim 7, wherein one end of the medical fluid channel is connected to the end of the injection needle, and the vicinity of the one end of the medical fluid channel can freely extend in a projecting direction of the injection needle.

9. The body-insertable apparatus according to claim 7, further comprising an elastic member that projects the injection needle by the medical-fluid discharger and generates an elastic force, and when the discharge pressure of the medical fluid decreases to equal to or less than the elastic force, uses the elastic force to bring the injection needle back to the casing.

10. The body-insertable apparatus according to claim 1, wherein the physical force for the discharge of the medical fluid is a pressurizing force for pressurizing the medical fluid by reducing the volume of the storage chamber.

11. The body-insertable apparatus according to claim 10, wherein the medical-fluid discharger includes
a medical fluid pressurizing unit that pressurizes the medical fluid by reducing the volume of the storage chamber,
a medical fluid channel for allowing the medical fluid pressurized by the medical fluid pressurizing unit to flow to the injection needle, and
a linking unit that links the medical fluid pressurizing unit to the injection needle and uses the pressurizing force by the medical fluid pressurizing unit to project the injection needle, in conjunction with the volume reduction of the storage chamber.

12. The body-insertable apparatus according to claim 11, further comprising:
an elastic member that generates an elastic force in a direction returning the injection needle into the casing, upon projection of the injection needle; and
a cutting unit that cuts the linking unit when the injection needle projects to a predetermined position, wherein
the elastic member uses the elastic force to bring the injection needle back to the casing, when the cutting unit cuts the linking unit.

13. The body-insertable apparatus according to claim 10, wherein the medical-fluid discharger includes
a medical fluid pressurizing unit which includes the injection needle, pressurizes the medical fluid by reducing the volume of the storage chamber, and projects the injection needle from the casing; and
a medical fluid channel for allowing the medical fluid pressurized by the medical fluid pressurizing unit to flow to the injection needle.

14. The body-insertable apparatus according to claim 1, wherein the medical-fluid discharger is a balloon.

15. The body-insertable apparatus according to claim 1, further comprising
a medical fluid channel which conveys the medical fluid discharged from the storage chamber into a channel of the injection needle,
wherein the medical fluid channel communicates with the channel of the injection needle only when the injection needle is projected from the casing.

16. A body-insertable apparatus having a storage chamber for storing a medical fluid in a capsule-like casing, the capsule-like casing being configured to be wholly introduced into a subject to discharge the medical fluid to a desired region in the subject, comprising:
a medical-fluid discharger forming the storage chamber that has, in a state where it stores the medical fluid therein, a contraction force for reducing the volume of itself to discharge the medical fluid; wherein the medical-fluid discharger is provided in the casing and discharges the medical fluid using the contraction force;
an injection needle that projects from the casing by using a physical force generated by the medical-fluid discharger for discharge of the medical fluid, to inject the medical fluid in the storage chamber into the desired region in the subject; and
a discharge controller that controls the start of volume change of the storage chamber by the medical-fluid discharger to start the discharge of the medical fluid;
wherein the discharge controller controls so as to stop volume reduction of the storage chamber by the medical-fluid discharger, to stop the discharge of the medical fluid and the medical fluid channel includes;
a first channel connecting to the storage chamber, and
a second channel connecting to the injection needle,
the discharge controller controls a connection state of the first channel and the second channel, and
the medical-fluid discharger starts volume reduction of the storage chamber when the first channel and the second channel are connected to each other, and stops volume reduction of the storage chamber when the first channel and the second channel are closed.

17. A body-insertable apparatus having a storage chamber for storing a medical fluid in a capsule-like casing, the capsule-like casing being configured to be wholly introduced into a subject to discharge the medical fluid to a desired region in the subject, comprising:
a medical-fluid discharger forming the storage chamber that has, in a state where it stores the medical fluid therein, a contraction force for reducing the volume of itself to discharge the medical fluid; wherein the medical-fluid discharger is provided in the casing and discharges the medical fluid using the contraction force;
an injection needle that projects from the casing to inject the medical fluid in the storage chamber into the desired region of the subject; and
a discharge starting unit that is provided in the casing, projects the injection needle from the casing, and starts a discharge operation of the medical-fluid discharger;
wherein the medical-fluid discharger has a medical fluid channel that connects the storage chamber to the injection needle, and
the discharge starting unit includes a communication adjusting unit that causes a state, in which a pressing force is applied to a part of the medical fluid channel to cut off a communicated state of the medical fluid channel, to be changed to a state, in which the pressing force is reduced to obtain the communicated state, thereby releasing the contraction force and starting the discharge operation of the medical-fluid discharger.

18. The body-insertable apparatus according to claim 17, wherein the medical-fluid discharger discharges the medical fluid by compressing the storage chamber.

19. The body-insertable apparatus according to claim 17, wherein the communication adjusting unit includes
a pressing unit that applies the pressing force to the part of the medical fluid channel to cut off the communicated state of the medical fluid channel,
a projecting unit that holds the injection needle and uses a predetermined drive source to project the injection needle from the casing, and
an associating unit that associates the projection operation by the projecting unit to project the injection needle with the communication adjusting operation by the pressing unit to reduce the pressing force to adjust the medical fluid channel to the communicated state.

20. The body-insertable apparatus according to claim 17, wherein the medical fluid channel includes
a first channel connecting to the storage chamber, and
a second channel connecting to the injection needle, and
the communication adjusting unit applies the pressing force to a region between the first channel and the second channel to cut off the communicated state of the medical fluid channel, projects the injection needle by using a predetermined drive source, and adjusts the medical fluid channel to the communicated state by reducing the pressing force, thereby starting the discharge operation of the medical-fluid discharger.

21. The body-insertable apparatus according to claim 17, wherein a predetermined drive source is a shape memory member, and the communication adjusting unit uses a driving force generated by a shape change of the shape memory member to project the injection needle, and adjusts the medical fluid channel to the communicated state.

22. The body-insertable apparatus according to claim 21, wherein the communication adjusting unit includes an elastic member that generates the pressing force, and when the shape memory member loses the driving force, uses the pressing force to store at least the injection needle in the casing.

23. A body-insertable apparatus having a medical fluid and an injection needle in a capsule-like casing, the capsule-like casing being configured to be wholly introduced into a subject to inject the medical fluid to a desired region in the subject, the body-insertable apparatus comprising:
- a medical-fluid discharger forming a storage chamber that has, in a state where it stores the medical fluid therein, a contraction force for reducing the volume of itself to discharge the medical fluid; wherein the medical-fluid discharger is provided in the casing and discharges the medical fluid using the contraction force, and projects the injection needle from the casing by using a physical force generated by the medical-fluid discharger; and
- an elastic member that generates an elastic force in a direction returning the injection needle into the casing, upon projection of the injection needle, and when the physical force for projecting the injection needle decreases to equal to or less than the elastic force, uses the elastic force to bring the injection needle back to the casing.

24. The body-insertable apparatus according to claim 23, wherein the physical force for projecting the injection needle is a discharge pressure of the medical fluid, and decreases to equal to or less than the elastic force when the medical-fluid discharger finishes discharge of a desired amount of the medical fluid.

25. The body-insertable apparatus according to claim 23, further comprising a discharge controller that controls to stop discharge of the medical fluid, so that the physical force for projecting the injection needle decreases to equal to or less than the elastic force.

26. The body-insertable apparatus according to claim 23, wherein the physical force for projecting the injection needle is a pressurizing force for pressurizing the medical fluid, and the medical-fluid discharger includes
- a linking unit that links the injection needle to the medical-fluid discharger and uses the pressurizing force to project the injection needle, and
- a cutting unit that cuts the linking unit when the injection needle projects to a predetermined position, to reduce the physical force for projecting the injection needle to equal to or less than the elastic force.

* * * * *